US010624899B2

(12) United States Patent
Krause et al.

(10) Patent No.: US 10,624,899 B2
(45) Date of Patent: Apr. 21, 2020

(54) COMBINATION PRODUCTS FOR THE TREATMENT OF BACTERIAL INFECTIONS AND METHODS OF PRODUCING OR DOSING OF SAME

(71) Applicant: ACHAOGEN, INC., South San Francisco, CA (US)

(72) Inventors: Kevin Michael Krause, San Francisco, CA (US); Daniel John Cloutier, San Francisco, CA (US); Allison Seiko Komirenko, Newark, CA (US); Ian Friedland, Brisbane, CA (US); Ryan Cirz, San Mateo, CA (US); Adrian Jubb, San Carlos, CA (US); Logan Andrews, San Francisco, CA (US)

(73) Assignee: ACHAOGEN, INC., South San Francisco, CA (US)

( * ) Notice: Subject to any disclaimer, the term of this patent is extended or adjusted under 35 U.S.C. 154(b) by 16 days.

(21) Appl. No.: 15/649,585

(22) Filed: Jul. 13, 2017

(65) Prior Publication Data
US 2018/0015100 A1 Jan. 18, 2018

Related U.S. Application Data

(60) Provisional application No. 62/465,051, filed on Feb. 28, 2017, provisional application No. 62/362,293, filed on Jul. 14, 2016.

(51) Int. Cl.
| | | |
|---|---|---|
| A61K 31/546 | (2006.01) | |
| A61K 31/397 | (2006.01) | |
| A61K 45/06 | (2006.01) | |
| A61K 9/00 | (2006.01) | |
| A61K 31/424 | (2006.01) | |

(52) U.S. Cl.
CPC .......... *A61K 31/546* (2013.01); *A61K 9/0053* (2013.01); *A61K 31/424* (2013.01); *A61K 45/06* (2013.01); *Y02A 50/473* (2018.01)

(58) Field of Classification Search
CPC ............................. A61K 31/397; A61K 31/546
See application file for complete search history.

(56) References Cited

U.S. PATENT DOCUMENTS

| | | | |
|---|---|---|---|
| 4,110,165 A | 8/1978 | Cole et al. | |
| 4,223,006 A | 9/1980 | Taskis | |
| 4,529,720 A | 7/1985 | Cole et al. | |
| 4,560,552 A | 12/1985 | Cole et al. | |
| 5,679,789 A | 10/1997 | Clark et al. | |
| 5,910,322 A | 6/1999 | Rivett et al. | |
| 5,965,728 A | 10/1999 | Cook et al. | |
| 6,048,977 A | 4/2000 | Cole et al. | |
| 6,172,221 B1 | 1/2001 | Ruddick | |
| 6,177,421 B1 | 1/2001 | Moir et al. | |
| 6,962,717 B1 | 11/2005 | Huber et al. | |
| 7,666,860 B2 | 2/2010 | Ziegler et al. | |
| 7,767,823 B2 | 8/2010 | McKnight et al. | |
| 7,815,936 B2 | 10/2010 | Hasenzahl et al. | |
| 8,216,613 B2 | 7/2012 | Gryczke | |
| 8,263,125 B2 | 9/2012 | Vaya et al. | |
| 8,377,994 B2 | 2/2013 | Gray et al. | |
| 8,734,850 B2 | 5/2014 | Castan et al. | |
| 9,149,439 B2 | 10/2015 | Patel et al. | |
| 9,198,862 B2 | 12/2015 | Pilgaonkar et al. | |
| 2003/0109503 A1 | 6/2003 | Smith et al. | |
| 2004/0022844 A1 | 2/2004 | Hasenzahl et al. | |
| 2005/0013836 A1 | 1/2005 | Raad | |
| 2006/0024365 A1 | 2/2006 | Vaya et al. | |
| 2006/0051412 A1 | 3/2006 | Petereit et al. | |
| 2006/0222692 A1 | 10/2006 | Lane | |
| 2007/0116729 A1 | 5/2007 | Palepu | |
| 2008/0026056 A1 | 1/2008 | Guimberteau et al. | |
| 2008/0085301 A1 | 4/2008 | Lane | |
| 2008/0085302 A1 | 4/2008 | Lane | |
| 2008/0305160 A1 | 12/2008 | Guimberteau et al. | |
| 2008/0312168 A1 | 12/2008 | Pilgaonkar et al. | |
| 2009/0155387 A1 | 6/2009 | Zhang | |
| 2009/0156518 A1 | 6/2009 | Zhang | |
| 2009/0220611 A1 | 9/2009 | Dargelas et al. | |
| 2009/0275552 A1* | 11/2009 | Patel .................... | A61K 9/0019 514/210.05 |
| 2009/0306224 A1 | 12/2009 | Gray et al. | |
| 2013/0059774 A1 | 3/2013 | Patel et al. | |
| 2013/0065790 A1 | 3/2013 | Vos | |
| 2013/0071475 A1 | 3/2013 | Petereit et al. | |
| 2013/0129791 A1 | 5/2013 | Bilgic | |
| 2013/0296228 A1 | 11/2013 | Patel et al. | |
| 2015/0140111 A1 | 5/2015 | Bilgic | |
| 2016/0051476 A1 | 2/2016 | Pilgaonkar et al. | |
| 2016/0058750 A1 | 3/2016 | Duffy | |

FOREIGN PATENT DOCUMENTS

| | | |
|---|---|---|
| WO | WO-1994/016696 | 8/1994 |
| WO | WO-2002/005850 | 1/2003 |
| WO | WO-2003/037379 | 5/2003 |
| WO | WO-2004/108091 | 5/2005 |
| WO | WO-2006/010868 | 2/2006 |

(Continued)

OTHER PUBLICATIONS

Flores-Mireles et al. ("Urinary tract infections: epidemiology, mechanisms of infection and treatment options." Nat Rev Microbiol. (Apr. 8, 2015); 13(5):269-284). (Year: 2015)*

(Continued)

*Primary Examiner* — Jeffrey S Lundgren
*Assistant Examiner* — Chris E Simmons
(74) *Attorney, Agent, or Firm* — Morrison & Foerster LLP

(57) ABSTRACT

Provided herein are methods of treating a bacterial infection, wherein the methods comprise administering (a) ceftibuten or a pharmaceutically acceptable salt thereof, or a hydrate of the foregoing; and (b) clavulanic acid, or a pharmaceutically acceptable salt thereof. Also provided are pharmaceutical compositions, articles of manufacture, and kits comprising a) ceftibuten or a pharmaceutically acceptable salt thereof, or a hydrate of the foregoing; and (b) clavulanic acid, or a pharmaceutically acceptable salt thereof, and uses thereof.

30 Claims, 12 Drawing Sheets

(56) References Cited

FOREIGN PATENT DOCUMENTS

| | | |
|---|---|---|
| WO | WO-2006/056711 | 8/2006 |
| WO | WO-2006/104763 | 10/2006 |
| WO | WO-2007/061529 | 5/2007 |
| WO | WO-2007/128349 | 11/2007 |
| WO | WO-2010/009335 | 1/2010 |
| WO | WO-2011/078820 | 6/2011 |
| WO | WO-2011/101710 | 8/2011 |
| WO | WO-2011/152806 | 8/2011 |
| WO | WO-2011/142731 | 11/2011 |
| WO | WO-2011/139253 | 5/2012 |
| WO | WO-2012/060785 | 5/2012 |
| WO | WO-2012/060788 | 5/2012 |
| WO | WO-2013/109225 | 7/2013 |
| WO | WO-2013/109227 | 7/2013 |
| WO | WO-2014/152332 | 9/2014 |
| WO | WO-2015/079389 | * 6/2015 |
| WO | WO-2016/116892 | 7/2016 |

OTHER PUBLICATIONS

Hashimoto et al. (Jpn J Antibiot. Feb. 1990;43(2):355-61. Abstract only). (Year: 1990).*

Hashimoto et al., Jpn J Antibiot. Feb. 1990;43(2):355-61. (Year: 1990).*

Bergogne-Berezin, "Mechanisms and clinical relevance of antagonism between beta-lactam antibiotics," Chemioterapia. Feb. 1985;4(1):47-52.

Food and Drug Administration. Ceftibuten Summary Basis of Approval. NDA 50-685 (capsules). Jan. 22, 1993 . Medical Officer Review 050685; 1993.

Furukawa et al., "Three-Month Subacute Toxicity Test of Intragastrically Administered Oral Cephem Antibiotics 7432-S in Rats," Chemotherapy. (1989) 37(suppl 1):858-882 (English translation only).

Hasegawa et al., "Reproduction Studies on 7432-S 3. Teratology Study in Rabbits," Chemotherapy. (1989) 37(suppl 1):1026-1039 (English translation only).

Hunter et al., "In vitro synergistic properties of clavulanic acid, with ampicillin, amoxycillin and ticarcillin," J Antimicrob Chemother. (1980) 6(4):455-70.

Klein et al., "Third-generation cephalosporins," Med Clin North Am. (1995) 79(4):705-19.

Kobayashi et al., "A one-month subacute toxicity study of 7432-s in dogs," Chemotherapy (1989) 37:833-857 (Including English translation).

Kobayashi et al., "Acute toxicity study of 7432-s and 7432-s-trans in rats and dogs," Chemotherapy. (1989) 37(suppl 1):804-815 (Including English translation).

Kobayashi et al., "One month subacute toxicity study of 7432-s (ceftibuten), an oral cephem antibiotic, in rats," Chemotherapy. (1989) 37(suppl 1):816-832 (Including English translation).

Kumazawa et al., "A double-blind study to compare 7432-S and cefaclor for the treatment of complicated urinary tract infections," Chemotherapy. (1989) 37(suppl 1):644-666 (Including English translation).

Leissa, Ceftibuten—Medical Officer's Review of NDA 50-685 (ceftibuten capsules): Integrated Safety Summary. Dates of Review: Jan. 2, 1992-Feb. 2, 1993.

Mashimo, "New antibiotics series XIII]: BRL 25000 (clavulanic acid/amoxicillin)," Jpn J Antibiot. (1985) 38(8):2011-25 (English translation only).

McAdoo et al., "Comparison of ceftibuten once daily and amoxicillin-clavulanate three times daily in the treatment of acute exacerbations of chronic bronchitis," Clin Ther. (1998) 20(1):88-100.

Nakashima et al., "Phase I Study of 7432-S, a New Oral Cephem Antibiotic," Chemotherapy (1989) 37:78-109 (Including English translation).

Nakashimizu et al., "Pharmacokinetics of 7432-S, A New Oral Cephalosporin," In Experimental Animals. Chemotherapy (1989) 37(suppl 1):756-773 (Including English translation).

Nara et al., "3 months subacute toxicity study of oral cephem antibiotic 7432-s in dogs," Chemotherapy (1989) 37(suppl 1):883-918 (Including English translation).

Nara et al., "Six-Month Chronic Toxicity Test of 7432-S (Ceftibuten), an Oral Cephem Antibiotic, by Use of Dogs," Chemotherapy (1989) 37(suppl 1):945-971 (Including English translation).

O'Neill, "Tackling drug-resistant infections globally: Final report and recommendations," The Review on Antimicrobial Resistance, Published May 19, 2016, available online at: https://amr-review.org/sites/default/files/160525_Final%20paper_with%20cover.pdf.

Penchovsky et al., "Designing drugs that overcome antibacterial resistance: where do we stand and what should we do?," Expert Opin Drug Discov. (2015) 10(6):631-50.

Ventola, "The antibiotic resistance crisis: part 1: causes and threats," P T. (2015) 40(4):277-83.

Yahara et al., "6 months chronic toxicity study of 7432-s (ceftibuten), an oral cephem antibiotic, in rats," Chemotherapy. (1989) 37(suppl 1):919-944 (Including English translation).

Yamamoto et al., "General pharmacological study of the oral cephem-group antibiotic 7432-s and its metabolite 7432-s-trans," Chemotherapy (1989) 37(suppl 1):1093-1126 (Including English translation).

Adam et al., "Pharmacokinetics of amoxicillin and clavulanic acid administered alone and in combination," Antimicrob Agents Chemother. (1982) 22(3):353-7.

Alqahtani et al., "Identification and Characterization of Cefazolin-Induced Liver Injury," Clin Gastroenterol Hepatol. (2015) 13(7):1328-1336.e2.

Augmentin® [Package Insert]. Bridgewater, NJ: Dr. Reddy's Laboratories Inc; 2013.

Augmentin ES-600® [Package Insert]. Bristol, TN: Dr. Reddy's Laboratories Tennessee LLC; 2015.

Augmentin IV [Package Leaflet]. Worthing, West Sussex: SmithKline Beecham; 2015.

Augmentin XR® [Package Insert]. Bristol, TN: Dr. Reddy's Laboratories Tennessee LLC; 2014.

Babic et al., "What's new in antibiotic resistance? Focus on beta-lactamases," Drug Resist Updat. (2006) 9(3):142-56.

Ball et al., "Clavulanic acid and amoxycillin: a clinical, bacteriological, and pharmacological study," Lancet (1980) 1(8169):620-3.

Barr et al., "The pharmacokinetics of ceftibuten in humans," Diagn Microbiol Infect Dis. (1991) 14(1):93-100.

Bauernfeind et al., "Characterization of beta-lactamase gene blaPER-2, which encodes an extended-spectrum class a beta-lactamase," Antimicrob Agents Chemother (1996) 40(3):616-20.

Bedenic et al., "Sensitivity and specificity of various beta-lactam antibiotics and phenotypical methods for detection of TEM, SHV and CTX-M extended-spectrum beta-lactamases," J Chemother. (2007) 19(2):127-39.

Bolton et al., "The disposition of clavulanic acid in man," Xenobiotica. (1986) 16(9):853-63.

Bressolle et al., "Multiple-dose pharmacokinetics of ceftibuten after oral administration to healthy volunteers," J Pharm Sci. (1994) 83(9):1236-40.

Brown et al., "Acute pyelonephritis among adults: cost of illness and considerations for the economic evaluation of therapy," Pharmacoeconomics. (2005) 23(11):1123-42.

Burkhardt et al., "Single- and multiple-dose pharmacokinetics of linezolid and co-amoxiclav in healthy human volunteers," J Antimicrob Chemother. (2002) 50(5):707-12.

Bush et al., "Updated functional classification of beta-lactamases," Antimicrob Agents Chemother. (2010) 54(3):969-76.

Bush et al., "Epidemiological expansion, structural studies, and clinical challenges of new β-lactamases from gram-negative bacteria," Annu Rev Microbiol. (2011) 65:455-78.

Carattoli, "Resistance plasmid families in Enterobacteriaceae," Antimicrob Agents Chemother. (2009) 53(6):2227-38.

(56) References Cited

OTHER PUBLICATIONS

Castanheira et al., "Changes in the Frequencies of β-Lactamase Genes among Enterobacteriaceae Isolates in U.S. Hospitals, 2012 to 2014: Activity of Ceftazidime-Avibactam Tested against β-Lactamase-Producing Isolates," Antimicrob Agents Chemother. (2016) 60(8):4770-7.
Cedax® [Package Insert]. Gonzales, LA: Pernix Therapeutics, LLC; 2010.
Centers for Disease Control and Prevention Office of Infectious Disease. Antibiotic resistance threats in the United States, 2013. Apr. 2013. Retrieved from https://web.archive.org/web/20150228153934/http://www.cdc.gov/drugresistance/threat-report-2013/.
Chopra et al., "Impact of cefepime therapy on mortality among patients with bloodstream infections caused by extended-spectrum-β-lactamase-producing Klebsiella pneumoniae and *Escherichia coli*," Antimicrob Agents Chemother. (2012) 56(7):3936-42.
Clavulin® [Product Monograph]. Mississauga, Ontario: GlaxoSmithKlein Inc; 2014.
Craig et al., "Pharmacokinetic/pharmacodynamic parameters: rationale for antibacterial dosing of mice and men," Clin Infect Dis. (1998) 26(1):1-10; quiz 11-2.
Cronberg et al., "Fewer bacterial relapses after oral treatment with norfloxacin than with ceftibuten in acute pyelonephritis initially treated with intravenous cefuroxime," Scand J Infect Dis. (2001) 33(5):339-43.
Cuevas et al., "Comparative in vitro activity of cefditoren and other antimicrobials against Enterobacteriaceae causing community-acquired uncomplicated urinary tract infections in women: a Spanish nationwide multicenter study," Diagn Microbiol Infect Dis. (2010) 67(3):251-60.
Czaja et al., "Population-based epidemiologic analysis of acute pyelonephritis," Clin Infect Dis. (2007) 45(3):273-80.
Davies et al., "Bioavailability and pharmacokinetics of clavulanic acid in healthy subjects," Int J Clin Pharmacol Ther Toxicol. (1985) 23(2):70-3.
Delemos et al., "Amoxicillin-Clavulanate-Induced Liver Injury," Dig Dis Sci. (2016) 61(8): 2406-2416.
Doi et al., "Community-associated extended-spectrum β-lactamase-producing *Escherichia coli* infection in the United States," Clin Infect Dis. (2013) 56(5):641-8.
Esteve-Palau et al., "Clinical and economic impact of urinary tract infections caused by ESBL-producing *Escherichia coli* requiring hospitalization: A matched cohort study," J Infect. (2015) 71(6):667-74.
Faulkner et al., "Pharmacokinetic profile of cefixime in man," Pediatr Infect Dis J. (1987) 6(10):963-70.
Fontana, "Pathogenesis of idiosyncratic drug-induced liver injury and clinical perspectives," Gastroenterology. (2014) 146(4):914-28.
Foxman et al., "Antibiotic resistance and pyelonephritis," Clin Infect Dis. (2007) 45(3):281-3.
Foxman et al., "Urinary tract infection: self-reported incidence and associated costs," Ann Epidemiol. (2000) 10(8):509-15.
French et al., "Bactericidal agents in the treatment of MRSA infections—the potential role of daptomycin," J Antimicrob Chemother. (2006) 58(6):1107-17.
Frickmann et al., "Emerging rapid resistance testing methods for clinical microbiology laboratories and their potential impact on patient management," Biomed Res Int. (2014) 2014:375681.
Ganapathy et al., "Interaction of anionic cephalosporins with the intestinal and renal peptide transporters PEPT 1 and PEPT 2," Biochim Biophys Acta. (1997) 1324(2):296-308.
Gupta et al., "International clinical practice guidelines for the treatment of acute uncomplicated cystitis and pyelonephritis in women: A 2010 update by the Infectious Diseases Society of America and the European Society for Microbiology and Infectious Diseases," Clin Infect Dis. (2011) 52(5):e103-20.
Gutiérrez-Gutiérrez et al., "A Multinational, Preregistered Cohort Study of β-Lactam/β-Lactamase Inhibitor Combinations for Treatment of Bloodstream Infections Due to Extended-Spectrum-β-Lactamase-Producing Enterobacteriaceae," Antimicrob Agents Chemother. (2016) 60(7):4159-69.
Hamacher et al., "Changes in fecal flora and comparative multiple-dose pharmacokinetics of ceftibuten, cefpodoxime proxetil and amoxycillin/clavulanate," Clin Microbiol Infect. (1999) 5(6):339-354.
Harris et al., "Comparable outcomes for β-lactam/β-lactamase inhibitor combinations and carbapenems in definitive treatment of bloodstream infections caused by cefotaxime-resistant *Escherichia coli* or Klebsiella pneumoniae," Antimicrob Resist Infect Control. (2015) 4:14.
Hatzaki et al., "Cefditoren: Comparative efficacy with other antimicrobials and risk factors for resistance in clinical isolates causing UTIs in outpatients," BMC Infect Dis. (2012) 12:228.
Ho et al., "Comparative study of ceftibuten and cefixime in the treatment of complicated urinary tract infections," J Microbiol Immunol Infect. (2001) 34(3):185-9.
Horber et al., "Differential effect of impaired renal function on the kinetics of clavulanic acid and amoxicillin," Antimicrob Agents Chemother. (1986) 29(4):614-9.
Jackson et al., "Pharmacokinetic, toxicological, and metabolic studies with Augmentin," In: Rolinson GN and Watson A, eds. Augmentin: Clavulanate-potentiated Amoxycillin: Proceedings of the First Symposium: Excerpta Medica and Beecham Research Laboratories (1980) pp. 87-105.
Kammer et al., "Randomized comparative study of ceftibuten versus cefaclor in the treatment of acute lower respiratory tract infections," Diagn Microbiol Infect Dis. (1991) 14(1):101-5.
Keepers et al., "Bactericidal activity, absence of serum effect, and time-kill kinetics of ceftazidime-avibactam against β-lactamase-producing Enterobacteriaceae and Pseudomonas aeruginosa," Antimicrob Agents Chemother. (2014) 58(9):5297-305.
Kuehn et al., "Reported rates of diarrhea following oral penicillin therapy in pediatric clinical trials," J Pediatr Pharmacol Ther. (2015) 20(2):90-104.
Lakshminarayana et al., "Comprehensive physicochemical, pharmacokinetic and activity profiling of anti-TB agents," J Antimicrob Chemother. (2015) 70(3):857-67.
Lavigne et al., "Post-antibiotic and post-beta-lactamase inhibitor effects of ceftazidime plus sulbactam on extended-spectrum beta-lactamase-producing Gram-negative bacteria," J Antimicrob Chemother. (2004) 53(4):616-9.
Lee et al., "Cefepime therapy for monomicrobial bacteremia caused by cefepime-susceptible extended-spectrum beta-lactamase-producing Enterobacteriaceae: MIC matters," Clin Infect Dis. (2013) 56(4):488-95.
Lin et al., "Multiple-dose pharmacokinetics of ceftibuten in healthy volunteers," Antimicrob Agents Chemother. (1995) 39(2):356-8.
Lin et al., "Pharmacokinetics and dose proportionality of ceftibuten in men," Antimicrob Agents Chemother. (1995) 39(2):359-61.
Livermore et al., "Comparative in vitro activity of sulfametrole/trimethoprim and sulfamethoxazole/trimethoprim and other agents against multiresistant Gram-negative bacteria," J Antimicrob Chemother. (2014) 69(4):1050-6.
Livermore et al., "Strategies to overcome extended-spectrum β-lactamases (ESBLs) and AmpC β-lactamases in shigellae," Int J Antimicrob Agents (2011) 37(5):405-9.
Lob et al., "Susceptibility patterns and ESBL rates of *Escherichia coli* from urinary tract infections in Canada and the United States, SMART 2010-2014," Diagn Microbiol Infect Dis. (2016) 85(4):459-65.
MacKenzie et al., "Comparison of screening methods for TEM- and SHV-derived extended-spectrum beta-lactamase detection," Clin Microbiol Infect. (2002) 8(11):715-24.
MacVane et al., "Impact of extended-spectrum β-lactamase-producing organisms on clinical and economic outcomes in patients with urinary tract infection," J Hosp Med. (2014) 9(4):232-8.
Maki et al., "The risk of bloodstream infection in adults with different intravascular devices: a systematic review of 200 published prospective studies," Mayo Clin Proc. (2006) 81(9):1159-71.
Martinelli et al., "Amoxicillin-clavulanic acid in treatment of urinary tract infection due to gram-negative bacteria resistant to penicillin," Antimicrob Agents Chemother. (1981) 20(6):800-2.

(56) References Cited

OTHER PUBLICATIONS

Maslikowska et al., "Impact of infection with extended-spectrum β-lactamase-producing *Escherichia coli* or *Klebsiella* species on outcome and hospitalization costs," J Hosp Infect. (2016) 92(1):33-41.
Melano et al., "Multiple antibiotic-resistance mechanisms including a novel combination of extended-spectrum β-lactamases in a Klebsiella pneumoniae clinical strain isolated in Argentina," J Antimicrob Chemother (2003) 52 (1): 36-42.
Menon et al., "Comparison of ceftibuten transport across Caco-2 cells and rat jejunum mounted on modified Ussing chambers," Biopharm Drug Dispos. (2003) 24(7):299-308.
Menon et al., "Transporters involved in apical and basolateral uptake of ceftibuten into Caco-2 cells," Biopharm Drug Dispos. (2002) 23(8):317-26.
Mombelli et al., "Oral vs intravenous ciprofloxacin in the initial empirical management of severe pyelonephritis or complicated urinary tract infections: a prospective randomized clinical trial," Arch Intern Med. (1999) 159(1):53-8.
Muranushi et al., "Characteristics of ceftibuten uptake into Caco-2 cells," Pharm Res. (1994) 11(12):1761-5.
Muranushi et al., "Transport characteristics of ceftibuten, a new oral cephem, in rat intestinal brush-border membrane vesicles: relationship to oligopeptide and amino beta-lactam transport," Pharm Res. (1989) 6(4):308-12.
Nilsson-Ehle et al., "Pharmacokinetics of clavulanic acid, given in combination with amoxycillin, in volunteers," J Antimicrob Chemother. (1985) 16(4):491-8.
Normark et al., "Chromosomal beta-lactam resistance in enterobacteria," Scand J Infect Dis Suppl. (1986) 49:38-45.
Oteo et al, "Parallel increase in community use of fosfomycin and resistance to fosfomycin in extended-spectrum β-lactamase (ESBL)-producing *Escherichia coli*," J Antimicrob Chemother (2010) 65 (11): 2459-2463.
Owens et al., "Ceftibuten: an overview," Pharmacotherapy. (1997) 17(4):707-20.
Pallett et al., "Complicated urinary tract infections: practical solutions for the treatment of multiresistant Gram-negative bacteria," J Antimicrob Chemother. (2010) 65 Suppl 3:iii25-33.
Papanicolaou et al., "Novel plasmid-mediated beta-lactamase (MIR-1) conferring resistance to oxyimino- and alpha-methoxy beta-lactams in clinical isolates of Klebsiella pneumoniae," Antimicrob Agents Chemother. (1990) 34(11):2200-9.
Paterson et al., "Epidemiology of ciprofloxacin resistance and its relationship to extended-spectrum beta-lactamase production in Klebsiella pneumoniae isolates causing bacteremia," Clin Infect Dis. (2000) 30(3):473-8.
Paterson et al., "Extended-spectrum beta-lactamases: a clinical update," Clin Microbiol Rev. (2005) 18(4):657-86.
Paterson et al., "Outcome of cephalosporin treatment for serious infections due to apparently susceptible organisms producing extended-spectrum beta-lactamases: implications for the clinical microbiology laboratory," J Clin Microbiol. (2001) 39(6):2206-12.
Peterson et al., "A double-blind, randomized comparison of levofloxacin 750 mg once-daily for five days with ciprofloxacin 400/500 mg twice-daily for 10 days for the treatment of complicated urinary tract infections and acute pyelonephritis," Urology. (2008) 71(1):17-22.
Pillar et al., "The postantibiotic effect and post-β-lactamase-inhibitor effect of ceftazidime, ceftaroline and aztreonam in combination with avibactam against target Gram-negative bacteria," Lett Appl Microbiol. (2016) 63(2):96-102.
Pines et al., "Experience with amoxycillin plus potassium clavulanate in lower respiratory tract infections," Excerpta Medica (1980) 544:277-82.
Pittet et al., "Nosocomial bloodstream infection in critically ill patients. Excess length of stay, extra costs, and attributable mortality," JAMA. (1994) 271(20):1598-601.
Pulcini et al., "Forgotten antibiotics: an inventory in Europe, the United States, Canada, and Australia," Clin Infect Dis. (2012) 54(2):268-74.
Sádaba et al., "Pharmacokinetic/pharmacodynamic serum and urine profile of cefditoren following single-dose and multiple twice- and thrice-daily regimens in healthy volunteers: a phase I study," Rev Esp Quimioter. (2007) 20(1):51-60.
Sader et al., "Antimicrobial activity of ceftolozane/tazobactam tested against Pseudomonas aeruginosa and Enterobacteriaceae with various resistance patterns isolated in European hospitals (Dec. 2011)," J Antimicrob Chemother. (2014) 69(10):2713-22.
Sader et al., "Post-β-lactamase-inhibitor effect of tazobactam in combination with ceftolozane on extended-spectrum-β-lactamase-producing strains," Antimicrob Agents Chemother. (2014) 58(4):2434-7.
Salvo et al., "Adverse drug reactions related to amoxicillin alone and in association with clavulanic acid: data from spontaneous reporting in Italy," J Antimicrob Chemother. (2007) 60(1):121-6.
Sanchez et al., "Short-term effectiveness of ceftriaxone single dose in the initial treatment of acute uncomplicated pyelonephritis in women. A randomised controlled trial," Emerg Med J. (2002) 19(1):19-22.
Shimada et al., "Effects of protein binding on the isomerization of ceftibuten," J Pharm Sci. (1993) 82(5):461-5.
Shin et al., "Fluoroquinolone resistance in uncomplicated acute pyelonephritis: epidemiology and clinical impact," Microb Drug Resist. (2012) 18(2):169-75.
Soon et al., "Combinatorial Pharmacodynamics of Ceftolozane-Tazobactam against Genotypically Defined β-Lactamase-Producing *Escherichia coli*: Insights into the Pharmacokinetics/Pharmacodynamics of β-Lactam-β-Lactamase Inhibitor Combinations," Antimicrob Agents Chemother. (2016) 60(4):1967-73.
Souverein et al., "Clinical sensitivity and specificity of the Check-Points Check-Direct ESBL Screen for BD MAX, a real-time PCR for direct ESBL detection from rectal swabs," J Antimicrob Chemother. (2017) 72: 2512-2518.
Staniforth et al., "Amoxycillin/clavulanic acid: the effect of probenecid," J Antimicrob Chemother. (1983) 12(3):273-5.
Sugawara et al., "H+ coupled transport of orally active cephalosporins lacking an alpha-amino group across brush-border membrane vesicles from rat small intestine," J Pharm Pharmacol. (1991) 43(6):433-5.
Swaminathan et al., "Prevalence and risk factors for acquisition of carbapenem-resistant Enterobacteriaceae in the setting of endemicity," Infect Control Hosp Epidemiol. (2013) 34(8):809-817.
Terada et al., "Recognition of beta-lactam antibiotics by rat peptide transporters, PEPT1 and PEPT2, in LLC-PK1 cells," Am J Physiol. (1997) 273(5 Pt 2):F706-11.
Thorburn et al., "Postantibiotic and post-beta-lactamase inhibitor effects of amoxicillin plus clavulanate," Antimicrob Agents Chemother. (1996) 40(12):2796-801.
Timentin® [Package Insert]. Research Triangel Park, NC: GlaxoSmithKline; 2014.
Tremblay et al., "Pharmacokinetics of cefpodoxime in young and elderly volunteers after single doses," J Antimicrob Chemother. (1990) 26 Suppl E:21-8.
Ueo et al., "Human organic anion transporter hOAT3 is a potent transporter of cephalosporin antibiotics, in comparison with hOAT1," Biochem Pharmacol. (2005) 70(7):1104-13.
Vardakas et al., "Susceptibility of contemporary isolates to fosfomycin: a systematic review of the literature," Int J Antimicrob Agents. (2016) 47(4):269-85.
Wagenlehner et al., "Ceftazidime-avibactam Versus Doripenem for the Treatment of Complicated Urinary Tract Infections, Including Acute Pyelonephritis: RECAPTURE, a Phase 3 Randomized Trial Program," Clin Infect Dis. (2016) 63(6):754-762.
Wagenlehner et al., "Ceftolozane-tazobactam compared with levofloxacin in the treatment of complicated urinary-tract infections, including pyelonephritis: a randomised, double-blind, phase 3 trial (ASPECT-cUTI)," Lancet. (2015) 385(9981):1949-56.
Wagenlehner et al., "Efficacy, pharmacokinetic and pharmacodynamic profile of ceftolozane + tazobactam in the treatment of complicated urinary tract infections," Expert Opin Drug Metab Toxicol. (2016) 12(8):959-66.

(56) References Cited

OTHER PUBLICATIONS

Wiseman et al., "Ceftibuten. A review of its antibacterial activity, pharmacokinetic properties and clinical efficacy," Drugs. (1994) 47(5):784-808.

Witkowski et al., "Pharmacokinetic studies of amoxicillin, potassium clavulanate and their combination," Eur J Clin Microbiol. (1982) 1(4):233-7.

Yoshikawa et al., "Transport characteristics of ceftibuten (7432-S), a new oral cephem, in rat intestinal brush-border membrane vesicles: proton-coupled and stereoselective transport of ceftibuten," Pharm Res. (1989) 6(4):302-7.

Zilberberg et al., "Secular trends in gram-negative resistance among urinary tract infection hospitalizations in the United States, 2000-2009," Infect Control Hosp Epidemiol. (2013) 34(9):940-6.

Allergan, "AVYCAZ highlights of prescribing information," Revised on Feb. 2018. Retrieved on Aug. 10, 2018. Retrieved from https://www.allergan.com/assets/pdf/avycaz_pi.

Bonnefoy et al., "In vitro activity of AVE1330A, an innovative broad-spectrum non-β-lactam β-lactamase inhibitor," Journal of Antimicrobial Chemotherapy (2004) 54(2):410-417.

Cerexa, Inc, "Intravenous Ceftazidime-Avibactam (CAZ-AVI) for treatment in adults with cIAI, cUTI, HABP/VABP, or Bacteremia where there are Limited or No treatment Options," dated Dec. 5, 2014.

European Medicines Agency, "Assessment report—Zavicefta," Published Apr. 28, 2016. Retrieved on Aug. 9, 2018. Retrieved from http://www.ema.europa.eu/docs/en_GB/document_library/EPAR_-_Public_assessment_report/human/004027/WC500210236.pdf.

Stachyra et al., "Mechanistic studies of the inactivation of TEM-1 and P99 by NXL104, a novel non-beta-lactam beta-lactamase inhibitor," Antimicrob Agents Chemother (2010) 54(12):5132-5138.

Tarnberg et al., "In vitro activity of beta-lactam antibiotics against CTX-M-producing *Escherichia coli*," Eur J Clin Microbiol Infect Dis (2011) 30:981-987.

Teligent Pharma, Inc, "FORTAZ prescribing information," Dated Jul. 2017. Retrieved on Aug. 10, 2018. Retrieved form https://www.accessdata.fda.gov/drugsatfda_docs/label/2017/050578s061,050634s028lbl.pdf.

Hashimoto et al., "Clinical studies of ceftibuten in the field of urology," The Japanese Journal of Antibiotics (1990) XLIII-2 355:137-143 (including English translation).

"Achaogen Announces Positive Top-Line Results from First Clinical Trial of Orally-Administered Antibacterial Candidate C-Scape," Published on Jan. 2, 2018. Retrieved from http://investors.achaogen.com/news-releases/news-release-details/achaogen-announces-positive-top-line-results-first-clinical.

* cited by examiner

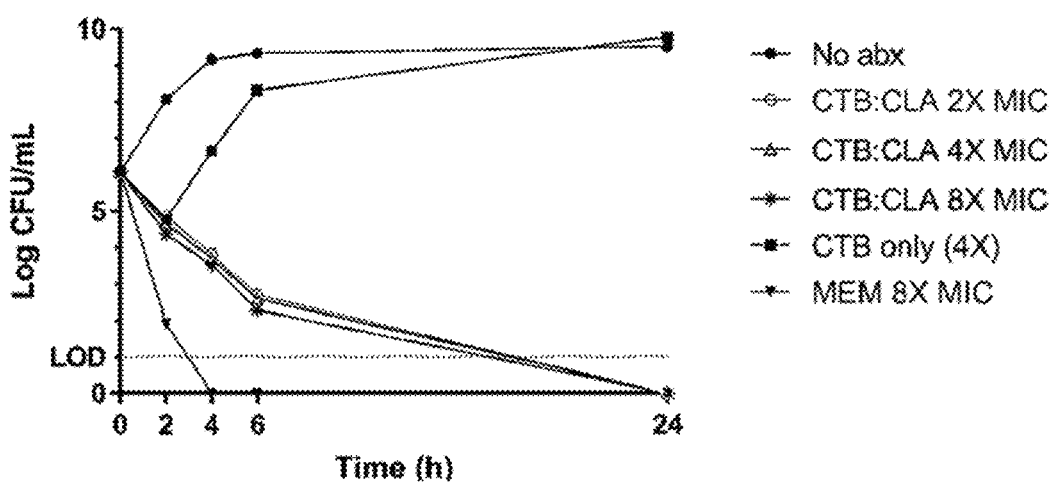
FIG. 1D  *E. coli* AECO1166 (SHV-12)
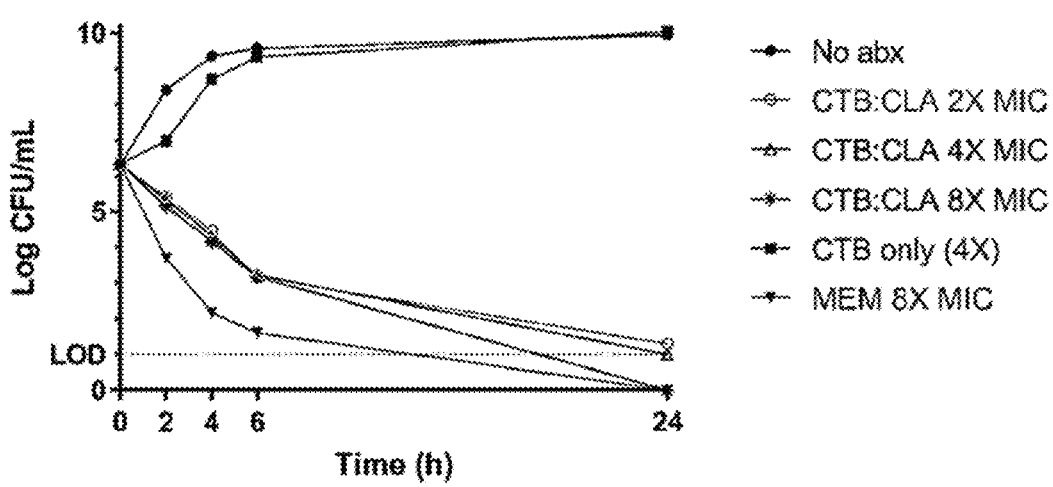
FIG. 1E  *K. pneumoniae* AKPN1159 (SHV-12)
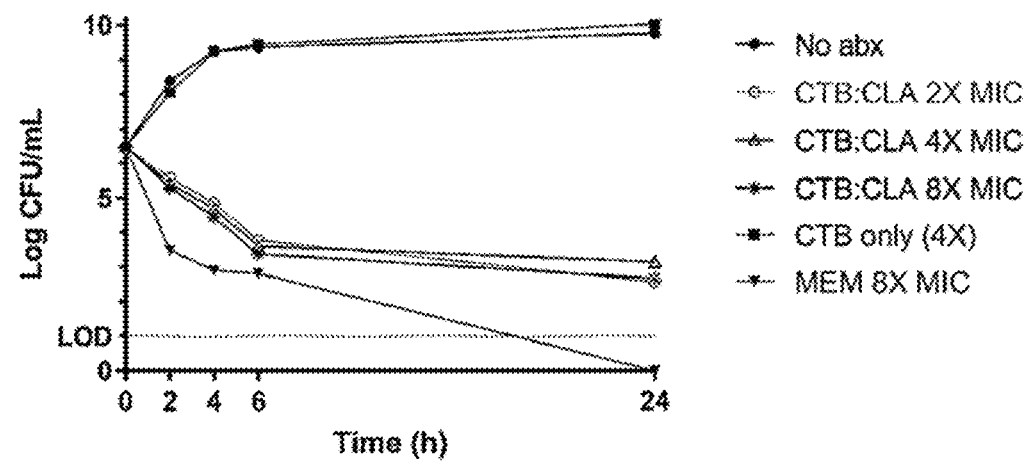
FIG. 1F  *K. pneumoniae* AKPN1162 (CTX-M-15, SHV-12)

COMBINATION PRODUCTS FOR THE TREATMENT OF BACTERIAL INFECTIONS AND METHODS OF PRODUCING OR DOSING OF SAME

CROSS-REFERENCE TO RELATED APPLICATIONS

The application claims the benefit of priority to U.S. provisional patent application 62/362,293, filed Jul. 14, 2016, entitled "COMBINATION PRODUCTS FOR THE TREATMENT OF BACTERIAL INFECTIONS AND METHODS OF PRODUCING OR DOSING OF SAME" and U.S. provisional patent application 62/465,051, filed Feb. 28, 2017, entitled "COMBINATION PRODUCTS FOR THE TREATMENT OF BACTERIAL INFECTIONS AND METHODS OF PRODUCING OR DOSING OF SAME," the contents of which are hereby incorporated by reference in their entirety for all purposes.

FIELD

The present invention provides a treatment of bacterial infections using a combination of a cephalosporin antibiotic and a β-lactamase inhibitor. Specifically, the present invention provides a treatment of urinary tract infections including complicated urinary tract infections, uncomplicated urinary tract infections and acute pyelonephritis caused by, but not limited to, species of the Enterobacteriaceae family.

BACKGROUND

Multidrug resistance is highly prevalent among the Enterobacteriaceae family, members of which are the most dominant uropathogens, including the most frequent causative pathogen in complicated urinary tract infection (cUTI). Many Enterobacteriaceae isolates produce extended-spectrum β-lactamases (ESBLs), rendering them resistant to many available antibiotics, including many oral antibiotics. Presently, no orally administered combination product of a cephalosporin and β-lactamase inhibitor is approved in the US or EU or is in clinical development for the treatment of bacterial infections, including infections involving ESBL-producing Enterobacteriaceae. Drug resistance for pathogenic bacteria is a growing problem. There is a need for new treatments to address this need. It is an object of the present invention to provide compositions, methods, uses and articles of manufacture, including those with desired features described herein, that meet such needs.

SUMMARY

Provided herein is a combination a cephalosporin antibiotic and a β-lactamase inhibitor for use in the treatment of bacterial infections. In some embodiments, the cephalosporin antibiotic is ceftibuten and the β-lactamase inhibitor is clavulanate. In some embodiments, the ceftibuten includes a pharmaceutically acceptable salt or hydrate thereof. In some embodiments, the clavulanate includes clavulanic acid or a pharmaceutically acceptable salt thereof. In some embodiments, the provided combination is effective in the treatment of bacterial infections resulting from Enterobacteriaceae. In some embodiments, the Enterobacteriaceae species is selected from the group consisting of isolates of *Citrobacter freundii, Enterobacter aerogenes, Enterobacter cloacae, Escherichia. coli, Klebsiella pneumoniae* and *Klebsiella oxytoca*. In a further embodiment, the combined composition is effective against Enterobacteriaceae species which are antibiotic resistant. In some embodiments, the Enterobacteriaceae expresses or produces an extended spectrum beta lactamase (ESBL).

In some of any of the provided embodiments, the combination of ceftibuten and clavulanate provided herein are for oral administration. In some embodiments, the combination of ceftibuten and clavulanate provided herein may come in several different dosage forms including, but not limited to, an oral suspension, an immediate release capsule or tablet, an extended release capsule or tablet or as a form for injection. In some embodiments, these various drug product forms may provide equivalent drug exposure.

In some of any of the provided embodiments, there is provided a combination composition wherein the formulation is selected from the group consisting of a suspension, a capsule, a tablet, or any other suitable form. In a preferred embodiment, the formulation is administered orally. In a preferred embodiment, the composition is a single formulation.

In some of any of the provided embodiments, the combination of the two agents described in this invention possesses several advantages over currently available drugs for the treatment of urinary tract infections, including, but not limited to: (1) greater activity and efficacy against β-lactamase producing Enterobacteriaceae, which are considered resistant to ceftibuten alone; (2) greater activity and efficacy against fluoroquinolone-resistant Enterobacteriaceae; (3) the potential for the treatment of recurrent urinary tract infections or urinary tract infections that are not responding to other medications; (4) the potential for treatment of urinary tract infections initially treated with intravenous antibiotics (oral stepdown therapy).

Provided herein are methods of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with or caused by a bacterium that expresses an extended-spectrum-β-lactamase (ESBL), and wherein the bacterial infection is a urinary tract infection (UTI), upper respiratory infection, lower respiratory tract infection, primary or catheter-associated blood infection, neonatal sepsis, intra-abdominal infection, otitis media, or a wound infection. In some embodiments, the infections include at least one infection selected from the group consisting of complicated urinary tract infection, uncomplicated urinary tract infection and acute pyelonephritis.

Provided herein are methods of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with a bacterium that expresses an extended-spectrum-β-lactamase (ESBL) that is or is believed to be CTX-M-14 or CTX-M-15.

Provided herein are methods of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, wherein the bacterial infection is associated with or caused by a bacterium that expresses an extended-spectrum-β-lactamase (ESBL), and wherein the individual was previously administered an antibiotic to treat the bacterial infection. In some of any of the provided embodiments, the method includes orally administering to the individual (a) ceftibuten or a pharmaceutically acceptable salt thereof, or a hydrate of the foregoing; and (b) clavulanic acid, or a pharmaceutically acceptable salt thereof, wherein the bacterial infection is associated with or caused by a bacterium that expresses an extended-spectrum-β-lactamase (ESBL), and wherein the individual was previously administered an antibiotic to treat the bacterial infection.

Provided herein are methods of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, or a hydrate of the foregoing, wherein component (a) is administered separately, simultaneously or sequentially with component (b), and wherein the bacterial infection is associated with or caused by a bacterium that expresses an ESBL, and wherein the method is characterized by one or more of (i)-(iii): (i) component (a) is administered to the individual at a daily dose of 800-1800 mg; (ii) component (b) is administered to the individual at a daily dose of 250-750 mg; (iii) a daily dose is administered in two or more divided doses of one or both of components (a) and (b).

Provided herein are methods of treating or prophylaxis of an Enterobacteriaceae bacterial infection in an individual, the method comprising orally administering to the individual (a) ceftibuten or a pharmaceutically acceptable salt thereof, or a hydrate of the foregoing, wherein: the bacterial infection is associated with or caused by an Enterobacteriaceae that expresses an extended-spectrum beta-lactamase (ESBL); the total daily dose of component (a) is administered in an amount of 800-1800 mg and/or is administered in two or more divided doses, the divided dose of compound (a) is about 300-400 mg; and component (a) is administered with (b) clavulanic acid, or a pharmaceutically acceptable salt thereof, wherein component (b) is orally administered in a total daily dose of about 250-750 mg and/or is administered in two or more divided doses per day, wherein the divided dose of component (b) is about 100-250 mg.

Provided herein are methods of treating or prophylaxis of an Enterobacteriaceae bacterial infection in an individual, the method comprising orally administering to the individual a (b) clavulanic acid, or a pharmaceutically acceptable salt thereof, wherein: the bacterial infection is associated with or caused by an Enterobacteriaceae that expresses an extended-spectrum beta-lactamase (ESBL); the total daily dose of component (b) is administered in an amount of 250-750 mg and/or is administered in two or more divided doses, wherein the divided dose of component (b) is about 100-250 mg; and component (b) is administered with (a) ceftibuten or a pharmaceutically acceptable salt thereof, or a hydrate of the foregoing, wherein component (a) is administered in a total daily dose of about 800-1800 mg and/or is administered in two or more divided doses, wherein the divided dose of component (a) is about 300-400 mg.

Provided herein are methods of treating an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection; and/or the bacterial infection is caused by or associated with an Enterobacteriaceae that expresses an extended spectrum β-lactamase (ESBL).

Provided herein are methods of prophylaxis of an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection; and/or the bacterial infection is caused by or associated with an Enterobacteriaceae that expresses an extended spectrum β-lactamase (ESBL).

Provided herein are methods of treating or prophylaxis of an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein the bacterial infection is a urinary tract infection (UTI), upper respiratory infection, lower respiratory tract infection, primary or catheter-associated blood infection, neonatal sepsis, intra-abdominal infection, otitis media, or a wound infection and/or wherein the bacterial infection is associated with or caused by an Enterobacteriaceae that expresses an extended-spectrum beta lactamase (ESBL); and (i) the component (a) and component (b) are administered in two or three divided doses per day, wherein the divided dose of component (a) is about 300-400 mg and the divided dose of component (b) is about 100-250 mg; and/or (ii) component (a) is administered in a total daily dose of about 900 to 1200 mg and component (b) is administered in a total daily dose of about 375 to 562.5 mg.

In some of any of the provided embodiments, component (a) is ceftibuten dihydrate. In some of any of the provided embodiments, component (b) is potassium clavulanate.

In some of any of the provided embodiments, one or both of components (a) and (b) are administered orally. In some of any of the provided embodiments, component (a) is administered simultaneously or sequentially with component (b). In some of any of the provided embodiments, components (a) and (b) are administered together in the same pharmaceutical composition.

In some of any of the provided embodiments, component (a) is administered to the individual at a ratio to component (b) of between 1:1-7:1. In some of any of the provided embodiments, component (a) is administered to the individual at a ratio to component (b) of between 1:1-3:1. In some of any of the provided embodiments, component (a) is administered to the individual at a ratio to component (b) of or about 1:1-2:1. In some of any of the provided embodiments, component (a) is administered to the individual at a ratio to component (b) of 2:1-4:1. In some of any of the provided embodiments, component (a) is administered to the individual at a ratio to component (b) of 2:1-3:1.

In some of any of the provided embodiments, the method is characterized by one or more of (i)-(iii): (i) component (a) is administered to the individual at a daily dose of 800-1800 mg; (ii) component (b) is administered to the individual at a daily dose of 250-750 mg; (iii) a daily dose is administered in two or more divided doses of one or both of components (a) and (b). In some of any of the provided embodiments, the method is characterized by (i) and the daily dose is administered in two or more divided doses. In some of any of the provided embodiments, the method is characterized by (ii) and the daily dose is administered in two or more divided doses. In some of any of the provided embodiments, the method is characterized by (i), (ii), and (iii).

In some of any of the provided, component (a) is administered in a total daily dose of 900 to 1200 mg. In some of any of the provided embodiments, component (b) is administered in a total daily dose of 375 mg to 562.5 mg. In some of any of the provided embodiments, the total daily dose of component (a) is about 900 to 1200 mg. In some of any of the provided embodiments, the total daily dose of component (b) is about 375 mg to 562.5 mg.

In some of any of the provided embodiments, the daily dose of one or both of components (a) and (b) is administered in 2-5 divided doses. In some of any of the provided embodiments, the divided dose is administered 2-5 times per day. In some of any of the provided embodiments, the daily dose of one or both of components (a) and (b) is administered in 2 or 3 divided doses. In some of any of the provided embodiments, the divided dose is administered 2 or 3 times per day.

In some of any of the provided embodiments, the divided dose of component (a) is about 300-600 mg. In some of any of the provided embodiments, the divided dose of component (a) is about 300-400 mg. In certain embodiments, the divided dose of component (a) is about 300-600 mg o. In some of any of the provided embodiments, the divided dose of component (a) is about 300-400 mg. In some of any of the provided embodiments, the divided dose of component (a) is about 400 mg. In some of any of the provided embodiments, the divided dose of component (a) is about 300 mg. In some of any of the provided embodiments, the divided dose of component (b) is about 100-250 mg of component (b). In some of any of the provided embodiments, the divided dose of component (b) is about 125-187.5 mg of component (b). In some of any of the provided embodiments, the divided dose of component (b) is about 125 mg of component (b). In some of any of the provided embodiments, the divided dose of component (b) is about 187.5 mg of component (b).

In some of any of the provided embodiments, one or both of components (a) and (b) are formulated as a capsule, solutab, sachet, suspension, or tablet. In some of any of the provided embodiments, component (a) and component (b) are combined in a single dosage form. In some of any of the provided embodiments, component (a) and component (b) are provided in separate dosage forms. In some of any of the provided embodiments, components (a) and (b) are formulated together. In some of any of the provided embodiments, one or both of components (a) and (b) are formulated as a capsule, and wherein the capsule is size 0, 1, or 2. In some of any of the provided embodiments, one or both of components (a) and (b) are formulated for modified or extended release.

In some of any of the provided embodiments, component (a) and component (b) are administered with food. In certain embodiments, component (a) and component (b) are administered without food.

In some of any of the provided embodiments, component (a) and component (b) are administered on an outpatient basis and/or are self-administered by the individual.

In some of any of the provided embodiments, component (a) and component (b) are administered for at least about or about 3 days, 4 day, 5 days, 6 days, 7 days, 8 day, 9 days, 10 days, 11 days, 12 days, 13 days, 14 days, 15 days, 16 days, 17 days, 18 days, 19 days, or 20 days. In some of any of the provided embodiments, component (a) and component (b) are administered for about 7 to 10 days.

In some of any of the provided embodiments, the individual is a human.

In some of any of the provided embodiments, the bacterium is an Enterobacteriaceae. In some of any of the provided embodiments, the bacterium is a *Citrobacter freundii, Enterobacter aerogenes, Enterobacter cloacae, Escherichia coli, Klebsiella pneumoniae*, or *Klebsiella oxytoca*.

In some of any of the provided embodiments, the bacterial infection is a urinary tract infection (UTI), upper respiratory infection, lower respiratory tract infection, primary or catheter-associated blood infection, neonatal sepsis, intra-abdominal infection, otitis media, or a wound infection. In some of any of the provided embodiments, the bacterial infection is a recurrent UTI, complicated UTI, uncomplicated UTI, bacteremic UTI, acute pyelonephritis, hospital-acquired pneumonia, ventilator-acquired pneumonia, or bronchitis. In some of any of the provided embodiments, the bacterial infection is a complicated urinary tract infection (cUTI), acute pyelonephritis, uncomplicated UTI (uUTI), complicated intra-abdominal infection (cIAI) or community acquired pneumonia (CAP). In some of any of the provided embodiments, the bacterial infection is a complicated UTI or acute pyelonephritis. In some of any of the provided embodiments, the individual has a renal impairment.

In some of any of the provided embodiments, the ESBL is inhibited by component (b). In some of any of the provided embodiments, the ESBL is a CTX-M, TEM, or SHV beta-lactamase. In some of any of the provided embodiments, the ESBL is CTX-M-14 or CTX-M-15 or is of the same CTX-M group as CTX-M-14 or CTX-M-15. In some of any of the provided embodiments, the ESBL is or is believed to be CTX-M-14 or CTX-M-15. In some of any of the provided embodiments, the bacterium expresses CTX-M-14. In some of any of the provided embodiments, the bacterium expresses CTX-M-15.

In some of any of the provided embodiments, the bacterium further expresses one or more additional beta-lactamase. In certain embodiments, the bacterium further expresses one or more additional ESBL. In some of any of the provided embodiments, the one or more additional beta-lactamase is independently CTX-M, a FEC, a KLUA, a KLUG, a TEM, a TOHO, or a SHV beta-lactamase. In some of any of the provided embodiments, the one or more additional beta-lactamase, such as one or more additional ESBL, is independently CTX-M, CTX-M-1, CTX-M-2, CTX-M-3, CTX-M-4, CTX-M-4L or CTX-M-89, CTX-M-5, CTX-M-6, CTX-M-7, CTX-M-8, CTX-M-9, CTX-M-10, CTX-M-12, CTX-M-13, CTX-M-14, CTX-M-15, CTX-M-16, CTX-M-17, CTX-M-19, CTX-M-20, CTX-M-21, CTX-M-22, CTX-M-23, CTX-M-24, CTX-M-25, CTX-M-26, CTX-M-27, CTX-M-28, FEC-1, KLUA-1, KLUA-5, KLUA-6, KLUA-8, KLUA-9, KLUA-10, KLUA-11, KLUG-1, SHV-2, SHV-7, SHV-12, TEM-1, TEM-OSBL, or TOHO-1. In some of any of the provided embodiments, the one or more additional beta-lactamase, such as one or more additional ESBL, is independently CTX-M-1, CTX-M-3, CTX-M-14, CTX-M-15, SHV-2, SHV-7, SHV-12, TEM-1, or TEM-OSBL.

In some of any of the provided embodiments, the bacterium has an antibiotic resistant phenotype. In some of any of the provided embodiments, the antibiotic resistant phenotype is resistance to a fluoroquinolone, a beta-lactam, or a beta-lactam:beta-lactamase inhibitor combination. In some of any of the provided embodiments, the antibiotic resistant phenotype is resistance to amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, ciprofloxacin, doripenem, gentamicin, imipenem, levofloxacin, loracarbef, meropenem, piperacillin, or tobramycin. In some of any of the provided embodiments, the antibiotic resistant phenotype is ST131.

In some of any of the provided embodiments, the bacterium does not express a protein selected from the group consisting of an AmpC, a KPC, an OXA, an NDM, or an OMP. In some of any of the provided embodiments, the bacterium does not express an AmpC. In some of any of the provided embodiments, the bacterium does not express a KPC. In some of any of the provided embodiments, the bacterium does not express an OXA. In some of any of the provided embodiments, the bacterium does not express an NDM. In some of any of the provided embodiments, the bacterium does not express an OMP.

In some of any of the provided embodiments, the individual was previously administered an antibiotic to treat the bacterial infection. In some of any of the provided embodiments, the previously administered antibiotic was a beta-lactam or a fluoroquinolone.

In some of any of the provided embodiments, the previously administered antibiotic was a beta-lactam which was a penicillin derivative, cephalosporin, monobactam, or carbapenem. In some of any of the provided embodiments, the previously administered antibiotic was a beta-lactam which was amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, doripenem, gentamicin, imipenem, loracarbef, meropenem, piperacillin, or tobramycin. In some of any of the provided embodiments, the previously administered antibiotic was a beta-lactam that was administered with a beta-lactamase inhibitor. In some of any of the provided embodiments, the previously administered beta-lactamase inhibitor was clavulanate, tazobactam, avibactam, or sulbactam.

In some of any of the provided embodiments, the previously administered antibiotic was a fluoroquinolone which was levofloxacin or ciprofloxacin.

In some of any of the provided embodiments, the previously administered antibiotic was not fully effective at treating the bacterial infection. In some of any of the provided embodiments, the previously administered antibiotic was an intravenously administered antibiotic. In some of any of the provided embodiments, administration of components (a) and (b) is a step-down therapy or is the oral portion of an intravenous to oral therapy switch. In some of any of the provided embodiments, components (a) and (b) are administered orally, and wherein the oral administration of components (a) and (b) is a step-down therapy or is the oral portion of an intravenous to oral therapy switch.

In some of any of the provided embodiments, the $IC_{50}$ of component (a) is greater than about 100 µM or 1000 µM for the ESBL. In some of any of the provided embodiments, the $K_M$ of component (a) is greater than about 100 µM for the ESBL.

In some of any of the provided embodiments, administration of components (a) and (b) in accord with the provided methods results in systemic exposure of component (a) of greater than 40% fT>MIC, greater than 50% fT>MIC, or greater than 60% fT>MIC of component (a). In some of any of the provided embodiments, administration of components (a) and (b) in accord with the provided methods results in systemic exposure of component (b) of greater than 20% fT>CT, greater than 25% fT>CT, greater than 30% fT>CT, or greater than 40% fT>CT.

In some of any of the provided embodiments, the administration of component (a) and component (b) results in a peak concentration of component (a) between about 5 µg/mL and 30 µg/mL, 5 µg/mL and 25 µg/mL, 5 µg/mL and 10 µg/mL, 10 µg/mL and about 30 µg/mL, between 10 µg/mL and 25 µg/mL, between 15 µg/mL and about 30 µg/mL, or between 15 µg/mL and about 25 µg/mL. In some of any of the provided embodiments, the peak concentration of component (b) is between about 0.1 µg/mL and 10 µg/mL, 0.1 µg/mL and 5 µg/mL, 0.1 µg/mL and 4 µg/mL, 0.1 µg/mL and 3 µg/mL, 0.1 µg/mL and 3 µg/mL, 0.1 µg/mL and 1 µg/mL, 0.2 µg/mL and 10 µg/mL, 0.2 µg/mL and about 5 µg/mL, between 0.2 µg/mL and 4 µg/mL, between 0.2 µg/mL and about 3 µg/mL, 0.2 µg/mL and 1 µg/mL, between 0.5 µg/mL and about 4 µg/mL, between 1 µg/mL and about 4 µg/mL, between 1 µg/mL and about 3 µg/mL. In some embodiments, the peak concentrations is peak serum concentration.

In some of any of the provided embodiments, the PBLIE of component (b) in combination with component (a) is or is greater than about 1 hour, greater than about 1.5 hours, greater than about 2 hours, or greater than about 2.5 hours. In some of any of the provided embodiments, the MIC of component (a) when used in combination with component (b) is or is less than about 4 µg/mL, is or is less than about 2 µg/mL, is or is less than about 1 µg/mL, or is or is less than about 0.5 µg/mL. In some of any of the provided embodiments, the MIC of component (a) alone is or is greater than about 4 µg/mL. In some of any of the provided embodiments, the MIC of component (a) alone is or is greater than about 4-fold more than the MIC of component (a) for the same microorganism, e.g. bacteria, e.g. ESBL-producing Enterobacteriaceae, when used in combination with component (b). In some of any of the provided embodiments, the MBC of component (a) when used in combination with component (b) is or is less than 4-fold or 2-fold higher than the MIC of component (a) when component (a) is used in combination with component (b), such as for the same microorganism, e.g. bacteria, e.g. ESBL-producing Enterobacteriaceae.

Provided herein are uses of (a) ceftibuten or a pharmaceutically acceptable salt thereof, or a hydrate of the foregoing and (b) clavulanic acid, or a pharmaceutically acceptable salt thereof in the manufacture of a medicament for treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); and the medicament is to be used to orally administer a divided dose of component (a) and a divided dose of component (b) to an individual, wherein component (a) and component (b) are to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are uses of (a) ceftibuten or a pharmaceutically acceptable salt thereof, or a hydrate of the foregoing in the manufacture of a medicament for treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); the medicament is to be used to orally administer a divided dose of component (a) to an individual, wherein component (a) is administered with (b) clavulanic acid, or a pharmaceutically acceptable salt thereof, wherein component (b) is orally administered in a divided dose; and component (a) and component (b) are to be administered in two or more divided doses per day and the divided doses are characterized by one or more of the following: (i) the divided dose of component (a) is for administering a total daily dose of 800-1800 mg; (ii) the divided daily dose of component (a) is at least or about at least 300 mg; (iii) the divided daily dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are uses of (b) clavulanic acid, or a pharmaceutically acceptable salt thereof in the manufacture of a medicament for treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); the medicament is to be used to orally administer a divided dose of component (b) to an individual, wherein component (b) is for administration with (a) ceftibuten or a pharmaceutically acceptable salt thereof, or a hydrate of the foregoing, wherein component (a) is orally administered in a divided dose; and component (a) and component (b) are to be administered in two or more divided doses per day and the divided doses are characterized by one or more of the following: (i) the divided dose of component (a) is for administering a total daily dose of 800-1800 mg; (ii) the divided daily dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are uses of (a) ceftibuten or a pharmaceutically acceptable salt thereof, or a hydrate of the foregoing and (b) clavulanic acid, or a pharmaceutically acceptable salt thereof in the manufacture of a medicament for treating or prophylaxis of an Enterobacteriaceae bacterial infection, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL), and wherein components (a) and (b) are formulated for oral administration. In some embodiments, component (a) is ceftibuten dihydrate. In some embodiments, component (b) is potassium clavulanate.

In some of any of the provided embodiments, the medicament is to be used to orally administer a divided dose of component (a) and/or a divided dose of component (b) to an individual, wherein the component (a) and component (b) are to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, the divided dose of component (a) is administered with a divided dose of component (b).

Provided herein are pharmaceutical compositions comprising (a) ceftibuten or a pharmaceutically acceptable salt thereof, or a hydrate of the foregoing and (b) clavulanic acid, or a pharmaceutically acceptable salt thereof, or a hydrate of the foregoing for use in treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); and the pharmaceutical composition is to be used to orally administer a divided dose of component (a) and a divided dose of component (b) to the individual, wherein component (a) and component (b) are to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are pharmaceutical compositions comprising (a) ceftibuten or a pharmaceutically acceptable salt thereof, or a hydrate of the foregoing for treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); and the pharmaceutical composition is to be used to orally administer a divided dose of component (a) to an individual, component (a) is administered with (b) clavulanic acid, or a pharmaceutically acceptable salt thereof, wherein component (b) is orally administered in a divided dose; and component (a) and component (b) are to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are pharmaceutical compositions comprising (b) clavulanic acid, or a pharmaceutically acceptable salt thereof for use in treating or prophylaxis of an Enterobacteriaceae bacterial infection, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); the pharmaceutical composition is to be used to orally administer a divided dose of component (b) to an individual, wherein component (b) is for administration with (a) ceftibuten or a pharmaceutically acceptable salt thereof, or a hydrate of the foregoing, wherein component (a) is orally administered in a divided dose; and component (a) and component (b) are to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are pharmaceutical compositions comprising (a) ceftibuten or a pharmaceutically acceptable salt thereof, or a hydrate of the foregoing and (b) clavulanic acid, or a pharmaceutically acceptable salt thereof for treating or prophylaxis of an Enterobacteriaceae bacterial infection, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL), and wherein the pharmaceutical composition is formulated for oral administration. In some embodiments, component (a) is ceftibuten dihydrate. In some embodiments, component (b) is potassium clavulanate.

In some of any of the provided embodiments, the composition is to be used to orally administer a divided dose of component (a) and/or a divided dose of component (b) to an individual, wherein component (a) and component (b) is to be administered in two or more divided doses per day and the divided doses are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg.

In some of any of the provided embodiments, component (a) and component (b) are combined in a single dosage form. In some of any of the provided embodiments, component (a) and component (b) are provided in separate dosage forms. In some of any of the provided embodiments, component (a) and component (b) are for administration simultaneously, concurrently or sequentially. In some of any of the provided embodiments, component (a) and component (b) are for administration together. In some of any of the provided embodiments, component (a) and component (b) are for administration separately. In some of any of the provided embodiments, component (a) and component (b) are to be used on an outpatient basis and/or are to be self-administered by the individual.

Provided herein are kits comprising (a) ceftibuten or a pharmaceutically acceptable salt thereof, or a hydrate of the foregoing; (b) clavulanic acid, or a pharmaceutically acceptable salt thereof, or a hydrate of the foregoing, and wherein the bacterial infection is associated with a bacterium that expresses an extended-spectrum-β-lactamase (ESBL); and (c) instructions for performing any method described herein.

Provided herein are kits comprising (a) ceftibuten or a pharmaceutically acceptable salt thereof, or a hydrate of the foregoing; (b) clavulanic acid, or a pharmaceutically acceptable salt thereof, or a hydrate of the foregoing, and wherein the bacterial infection is associated with a bacterium that expresses an extended-spectrum-β-lactamase (ESBL); and (c) instructions for administering an effective amount of components (a) and (b) for treatment of a bacterial infection to an individual in need thereof, wherein the bacterial infection is associated with a bacterium that expresses an extended-spectrum-β-lactamase (ESBL).

Provided herein are kits comprising at least two oral dosage forms comprising (a) ceftibuten or a pharmaceutically acceptable salt thereof, or a hydrate of the foregoing and/or at least two oral dosage forms comprising (b) clavulanic acid, or a pharmaceutically acceptable salt thereof, wherein each dosage form is for oral administration to an individual of a unit dose; the at least two dosage forms of component (a) and/or the at least two dosage forms of component (b) are for oral administration to an individual of a divided dose of component (a) and/or component (b) two or more times per day and are characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

Provided herein are kits for treating or prophylaxis of an Enterobacteriaceae bacterial infection, the kit comprising at least two oral dosage forms comprising (a) ceftibuten or a pharmaceutically acceptable salt thereof, or a hydrate of the foregoing and/or at least two oral dosage forms comprising (b) clavulanic acid, or a pharmaceutically acceptable salt thereof, wherein: the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is associated with or caused by an Enterobacteriaceae that expresses an extended-spectrum beta-lactamase (ESBL); each dosage form is for oral administration to an individual of a unit dose, the at least two oral dosage forms of component (a) and/or the at least two oral dosage forms of component (b) are for administering a divided dose of component (a) and/or component (b) two or more times per day, wherein component (a) is administered with component (b); and the divided dose is characterized by one or more of the following: (i) the divided dose of component (a) is for administering a total daily dose of 800-1800 mg; (ii) the divided dose of component (a) is at least or about at least 300 mg; (iii) the divided dose of component (b) is for administering a total daily dose of 250-750 mg; and/or (iv) the divided dose of component (b) is at least or about at least 100 mg. In some embodiments, component (a) is ceftibuten dihydrate. In some embodiments, component (b) is potassium clavulanate.

In some of any of the provided embodiments, component (a) and component (b) are combined in a single dosage form. In some of any of the provided embodiments, component (a) and component (b) are provided in separate dosage forms.

In some of any of the provided embodiments, the kit further comprises instructions for use of component (a) and component (b). In some of any of the provided embodiments, the kit further comprises instructions for administering component (a) or component (b) to the individual. In some of any of the provided embodiments, the instructions specify the kit is for use in treating or prophylaxis of an Enterobacteriaceae bacterial infection. In some of any of the provided embodiments, the instructions specify the divided dose of component (a) and component (b) is for administration together. In some of any of the provided embodiments, the instructions specify the divided dose of component (a) and component (b) is for administration separately. In some of any of the provided embodiments, the instructions specify the divided dose of component (a) and the divided dose of component (b) is for administration simultaneously, concurrently or sequentially. In some of any of the provided embodiments, the instructions specify the component (a) and component (b) are for administration on an outpatient basis and/or are to be self-administered by the individual. In some of any of the provided embodiments, the instructions specify the divided dose of component (a) and the divided dose of component (b) is to be administered 2-5 times per day. In some of any of the provided embodiments, the instructions specify the divided dose of component (a) and the divided dose of component (b) is to be administered 2 or 3 times per day.

In some of any of the provided embodiments, the divided dose of component (a) is 300-600 mg. In some of any of the provided embodiments, the divided dose of component (a) is 300-400 mg. In some of any of the provided embodiments, the divided dose of component (a) is about 400 mg of component (a). In some of any of the provided embodiments, the divided dose of component (a) is about 300 mg of component (a). In some of any of the provided embodiments, the total daily dose of component (a) is about 900 to 1200 mg. In some of any of the provided embodiments, the divided dose of component (b) is about 100-250 mg of component (b). In some of any of the provided embodiments, the divided dose of component (b) is about 125-187.5 mg of component (b). In some of any of the provided embodiments, the total daily dose of component (b) is about 375 mg to 562.5 mg. In some of any of the provided embodiments, the divided dose of component (b) is about 125 mg of component (b). In some of any of the provided embodiments, the divided dose of component (b) is about 187.5 mg of component (b).

In some of any of the provided embodiments, the oral dosage form comprises a capsule, solutab, sachet, suspension, or tablet. In some of any of the provided embodiments, the oral dosage from is a capsule and the capsule is size 0, 1 or 2. In some of any of the provided embodiments, one or both of the oral dosage form of component (a) and component (b) are formulated for modified or extended release.

In some of any of the provided embodiments, component (a) and component (b) are packaged in the same container. In some of any of the provided embodiments, component (a) and component (b) are packaged in a different container. In some of any of the provided embodiments, the container is a divided container, wherein the at least two oral dosage forms of component (a) are separated from each other in the divided container and/or the at least two oral dosage forms of component (b) are separated from each other in the divided container. In some of any of the provided embodiments, the container is a blister pack. In some of any of the provided embodiments, the kit contains at least one additional antibiotic. In some embodiments, the additional antibiotic is packaged in a container with component (a) and/or component (b). In some embodiments, the additional antibiotic is formulated with component (a). In some embodiments, the additional antibiotic is formulated with component (b).

BRIEF DESCRIPTION OF THE DRAWINGS

FIGS. 1A-1F show time dependent killing of ceftibuten (CTB) and CTB in combination with clavulanate (CLA) at 2-, 4-, and 8-fold above the minimum inhibitory concentration (MIC). For cultures treated with ceftibuten alone, the concentration was equivalent to 4-fold above the MIC of the ceftibuten-clavulanate combination. Meropenem (MEM)

was included as a comparator at 8-fold above its MIC. FIG. 1A shows the results for *E. coli* strain AECO1156 which expresses CTX-M-15 and TEM-OSBL. FIG. 1B shows the results for *E. coli* AECO1157 which expresses CTX-M-15 and TEM-OSBL. FIG. 1C shows the results for *E. coli* AECO1162 which expresses CTX-M-14. FIG. 1D shows the results for *E. coli* AECO1166 which expresses SHV-12. FIG. 1E shows the results for *K. pneumoniae* AKPN1159 which expresses SHV-12. FIG. 1F shows the results for *K. pneumoniae* AKPN1162 which expresses CTX-M-15 and SHV-12.

Figure 1A:
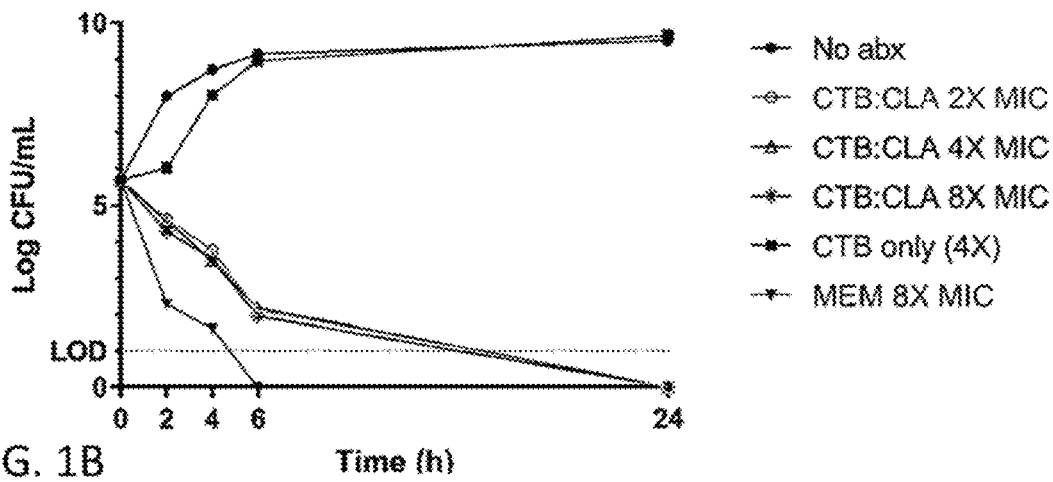
Figure 1B:
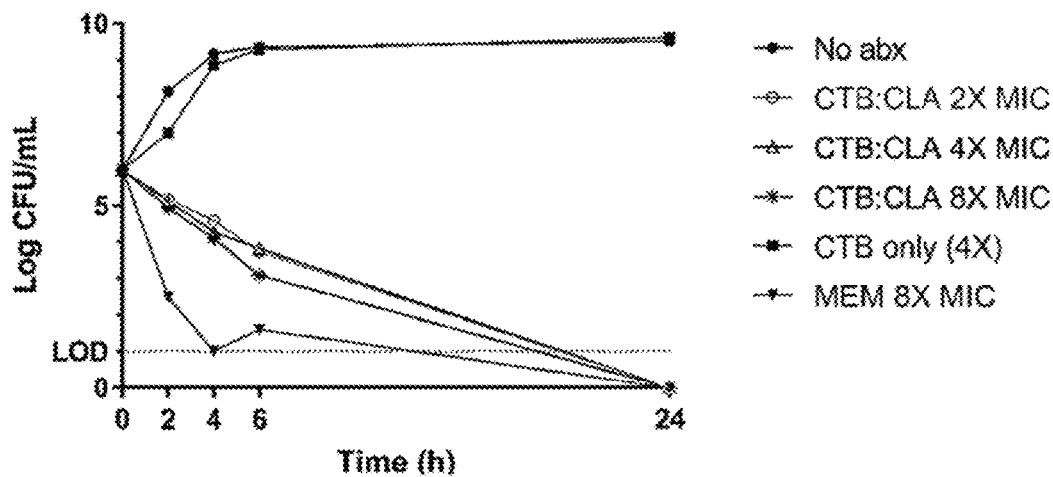
Figure 1C:
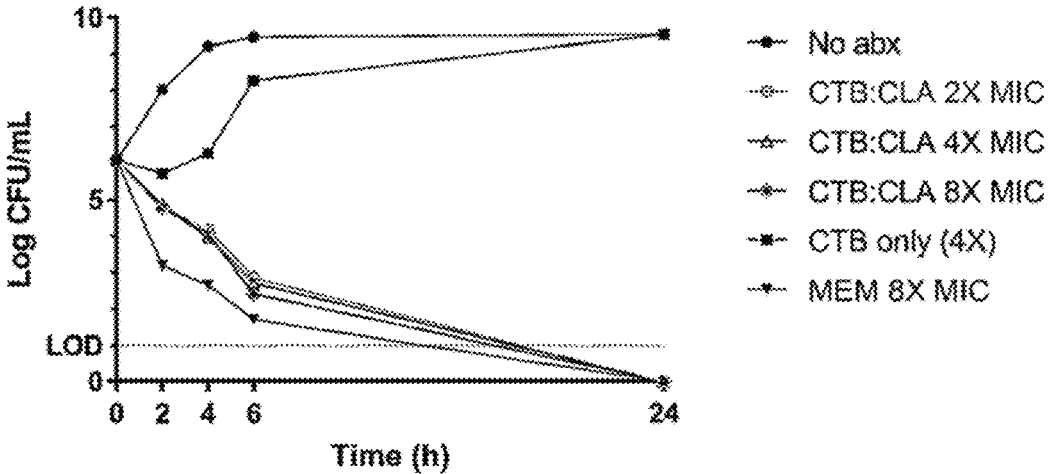

The invention can be better visualized by turning now to the following description. It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

Provided herein are methods of treating a bacterial infection, wherein the methods comprise administering (a) ceftibuten or a pharmaceutically acceptable salt thereof, or a hydrate of the foregoing; and (b) clavulanic acid, or a pharmaceutically acceptable salt thereof. Also provided are pharmaceutical compositions, articles of manufacture, and kits comprising a) ceftibuten or a pharmaceutically acceptable salt thereof, or a hydrate of the foregoing; and (b) clavulanic acid, or a pharmaceutically acceptable salt thereof, and uses thereof.

For clarity of disclosure, and not by way of limitation, the detailed description is divided into the subsections that follow. The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The term MIC as used herein refers to the minimum inhibitory concentration of an antimicrobial agent that will inhibit the visible growth of a microorganism after a certain time of incubation, for example, after overnight incubation. MICs are important in diagnostic laboratories to confirm resistance of microorganisms to an antimicrobial agent and also to monitor the activity of new antimicrobial agents. An MIC is generally regarded as the most basic laboratory measurement of the activity of an antimicrobial agent against an organism and is reported with units of either micrograms per milliliter (μg/mL) or milligrams per liter (mg/L). The $MIC_{90}$ and $MIC_{50}$ are common metrics used to assess the in vitro susceptibility of a cohort of bacterial isolates to a specific drug or combination of drugs using the aforementioned testing method. $MIC_{90}$ and $MIC_{50}$ values refer to the lowest concentration of the antibiotic at which 90 and 50% of the isolates are inhibited, respectively. In some embodiments, the $MIC_{90}$ is defined as the lowest concentration of an antibiotic at which the visible growth of 90% of microorganism isolates are inhibited after overnight incubation. In some embodiments, the $MIC_{50}$ is defined as the lowest concentration of an antibiotic at which the visible growth of 50% of microorganism isolates are inhibited after overnight incubation.

The term pharmacokinetics (PK) as used herein refers to the time course of drug concentrations in plasma (and sometimes in other fluids and tissues) resulting from a particular dosing regimen.

The term pharmacodynamics (PD) as used herein expresses the relationship between drug concentrations in plasma (and sometimes in other fluids and tissues) and a resulting pharmacological effect.

The term PK/PD Index for antimicrobial agents is a parameter of pharmacodynamics expressed as bacteriostasis, 1-log kill or 2-log kill, and linked to the pharmacokinetics to constitute an exposure-response relationship (PK/PD) that is adjusted for the MIC of a given bacterial isolate. The most common PK/PD measures associated with efficacy are the area under the concentration-time curve (AUC) to MIC ratio, peak concentration ($C_{max}$) to MIC ratio, and the percentage of time that drug concentrations exceed the MIC over the dosing interval (T>MIC) (Clin Infect Dis 1998; 26:1-10). To reflect free or unbound (i.e., what is considered microbiologically active) drug, these PK/PD indices are typically corrected for plasma protein binding and expressed as fAUC:MIC, $fC_{max}$:MIC, and fT>MIC. Efficacy for the β-lactam class is driven by fT>MIC exposures and a magnitude of 40% fT>MIC has been demonstrated to be associated with a bacteriostatic effect by cephalosporins against Enterobacteriaceae (Clin Infect Dis 1998; 26:1-10).

Cephalosporins are antibiotics indicated for the prophylaxis and treatment of infections caused by susceptible bacteria. First-generation cephalosporins are active predominantly against Gram-positive bacteria; successive generations have increased activity against Gram-negative bacteria (albeit, often, with reduced activity against Gram-positive organisms).

Clavulanate is a β-lactam drug that functions as a mechanism-based β-lactamase inhibitor. While not effective by itself as an antibiotic, when combined with penicillin-group antibiotics, it can overcome antibiotic resistance in bacteria that secrete β-lactamases, which otherwise inactivates many β-lactam antibiotics, such as penicillins and cephalosporins.

The term PBLIE is the post-β-lactamase inhibitor effect defined as the persistent inhibition of bacterial growth after the β-lactamase inhibitor component of the β-lactam+β-lactamase inhibitor combination has been removed. It represents the time it takes for an organism to recover from the effects of β-lactamase inhibitor exposure and resume normal growth in the presence of the β-lactam alone. Thus, in order to calculate the PBLIE, two experimental conditions are compared. In the first, the bacteria are exposed to a β-lactam alone, and in the second to the combination of the same β-lactam in combination with a β-lactamase inhibitor. After one hour the cells are washed and re-suspended in media with the β-lactam alone, the growth is then monitored over time. The difference between the time it takes for the two cultures to grow 1-log of colony forming units per mL after washout (J Antimicrob Chemother 2004; 53:616-619) is the metric used to define the PBLIE.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. In some embodiments, the disease is or results from a bacterial infection. The methods of the invention contemplate any one or more of these aspects of treatment.

The term "individual" refers to a mammal and includes, but is not limited to, human, bovine, horse, feline, canine, rodent, or primate. Typically, the individual is a human.

The term "effective amount" used herein refers to an amount of a compound or composition sufficient to treat a specified disorder, condition or disease, such as a bacterial infection, such as ameliorate, palliate, lessen, and/or delay one or more of its symptoms. In reference to a bacterial infection, an effective amount comprises an amount sufficient to cause the total number of bacteria present in an individual to shrink and/or to slow the growth rate of the bacteria. In some embodiments, an effective amount is an amount sufficient to prevent or delay recurrence of the bacterial infection. In the case of bacterial infections, the effective amount of the drug or composition may: (i) reduce the number of bacterial cells; (ii) inhibit, retard, slow to some extent and preferably stop bacterial cell proliferation; (iii) prevent or delay occurrence and/or recurrence of the bacterial infection; and/or (iv) relieve to some extent one or more of the symptoms associated with the bacterial infection.

A "prophylactically effective amount" refers to an amount effective, at dosages and for periods of time necessary, to achieve the desired prophylactic result. In some cases, since a prophylactic dose is used in subjects prior to or at an earlier stage of disease, such as a bacterial infection, the prophylactically effective amount is less than the therapeutically effective amount.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, the singular form "a", "an", and "the" includes plural references unless indicated otherwise.

Reference to "about" a value or parameter herein refers to the usual error range for the respective value readily known to the skilled person in this technical field. In particular embodiments, reference to about refers to a range within 10% higher or lower than the value or parameter, while in other embodiments, it refers to a range within 5% or 20% higher or lower than the value or parameter. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

II. COMBINATION TREATMENT

Provided herein are methods and uses involving combined administration of ceftibuten or a pharmaceutically acceptable salt thereof, or a hydrate of the foregoing and clavulanic acid, or a pharmaceutically acceptable salt thereof, or a hydrate of the foregoing, including for treating a bacterial infection, such as Enterobacteriaceae bacterial infections, such as certain types of urinary tract infections (UTI) and/or bacterial infections caused by Enterobacteriaceae isolates that produce extended-spectrum β-lactamases (ESBLs). Also provided are pharmaceutical compositions, articles of manufacture, and kits containing a composition containing ceftibuten or a pharmaceutically acceptable salt thereof, or a hydrate of the foregoing; and/or a composition containing clavulanic acid, or a pharmaceutically acceptable salt thereof, and uses thereof, including for use in the provided methods. In some embodiments, the compositions are suitable for oral administration.

Certain bacterial infections, including those caused by Enterobacteriaceae, are difficult to treat, in part, due to the prevalence of multidrug resistance. Enterobacteriaceae are among the most dominant uropathogens; the Enterobacteriaceae *Escherichia coli* alone accounts for 65% to 85% of UTIs (Foxman et al. (2000) Ann. Epidemiol, 10:509-515; Czaja et al. (2007) Clin. Infect. Dis., 45:273-280; Wagenlehner et al. (2015) Clin. Infect. Dis., 63:754-762). In some aspects, urinary tract infections (UTI) are the most common bacterial infections acquired in community and hospital settings, leading to 3 million hospital treatment episodes every year in the United States The US government estimates that there are 1,050,000 complicated urinary tract infections, including pyelonephritis, each year in the USA, comprising 450,000 community-acquired and 600,000 hospital-acquired infections (Analytical Framework for Examining the Value of Antibacterial Products. US Department of Health and Human Services Task Number HHSP23337004T, 2014). Approximately 79% of these infections are caused by *E. coli* (Wagenlehner et al. (2015) Lancet, 385:1949-1956).

Surveillance in the United States (Lob et al. (2016) Diagn Microbiol Infect Dis, 85:459-465) and Europe (ECDC, EARS-Net, 2016, available from www.ecdc.europa.eu/sites/portal/files/documents/antibiotics-EARS-Net-summary-2016.pdf) have shown that, in many cases, *E. coli* cultured from a urinary source are increasingly resistant to existing antibiotics. For example, 16% of community-acquired and 28% of hospital-associated *E. coli* isolates from a urinary source were reported in 2014 in the US to produce extended-spectrum 3-lactamases (ESBLs) (Lob et al. (2016) Diagn Microbiol Infect Dis, 85:459-465). The prevalence of ESBL-producing *E. coli* has increased approximately 3-fold since 2010 (Lob et al. (2016) Diagn Microbiol Infect Dis, 85:459-465). Between 10% and 30% of all clinical Enterobacteriaceae isolates in the US and European Union produce ESBLs (Paterson et al. (2005) Clin Microbiol. Rev., 18:657-686; Bush et al. (2011) Annu. Rev. Microbiol., 65:455-478). The threat of these ESBL-producing Enterobacteriaceae is highlighted by their classification as a "Serious Threat" by the Centers for Disease Control (CDC) and as a "Critical/Tier 1" threat by the World Health Organization (WHO).

The majority of ESBL-producing Enterobacteriaceae are resistant to β-lactam antibiotics, except, in some cases, carbapenems. The genes encoding ESBLs are often carried on plasmids that also carry resistance genes for other classes of antibacterial agents (Carattoli et al. (2009) Antimicrob. Agents Chemother., 63:2227-2238). In some aspects, Enterobacteriaceae isolates, including ESBL-producing *E. coli* isolates, are resistant to almost all orally available therapies, including cephalosporins (which are hydrolyzed by ESBLs) and drugs such as trimethoprim/sulfamethoxazole (Livermore et al. (2014) J Antimicrob Chemother, 69:1050-1056) and fluoroquinolones, resistance to which is often carried by ESBL-producing isolates (MacVane et al. (2014) J. Hosp. Med., 9:232-238; Paterson et al. (2000) Clin Infect Dis, 30:473-478). This is exemplified by the results in Example 1, which show that the MIC90 is above the breakpoint for susceptibility for cephalosporins (ceftazidime and ceftriaxone), trimethoprim/sulfamethoxazole, and a fluoroquinolone (levofloxacin), as determined using Clinical and Laboratory Standards Institute (CLSI) and European Committee on Antimicrobial Susceptibility Testing (EUCAST) breakpoints.

Thus, effective treatments with oral antibiotics against Enterobacteriaceae infections, including cUTIs, are limited by the increasing prevalence of resistance mechanisms, such as those due to ESBLs. In some cases where oral antibiotics may be available, they are not entirely effective for treating patients having infections associated with contemporary ESBL-producing Enterobacteriaceae isolates. For example, contemporary ESBL-producing *E. coli* from urinary tract infections in the US show approximately 85% susceptibility to oral nitrofurantoin, an oral antibiotic indicated for the treatment of urinary tract infections (MacVane et al. (2014) J Hosp Med, 9:232-238). However, nitrofurantoin is contraindicated in patients with pyelonephritis, perinephric abscesses or impaired renal function (Macrobid® Package Insert. Procter and Gamble Pharmaceuticals, Cincinnati, Ohio: 2008). However, the about 45% of patients that have renal impairment among patients ≥65 years of age, represent a significant proportion of patients with urinary tract infections (Coresh et al. (2007) JAMA, 298:2038-2047) (80% of patients admitted to hospital with a urinary tract infection due to ESBL-producing Enterobacteriaceae were ≥65 years of age in one US cohort). It also is reported that about thirty-five percent of patients enrolled in clinical trials of complicated urinary tract infections have evidence of renal impairment, and >50% are diagnosed with acute pyelonephritis (Wagenlehner et al. (2015) Lancet, 385:1949-1956). Oral fosfomycin has also been reported to be effective in the treatment of urinary tract infections due to ESBL-producing Enterobacteriaceae (Vardaka et al. (2016) Int J Antimicrob Agents, 47:269-285), but fosfomycin is not approved for use in complicated urinary tract infections and is contraindicated in patients with pyelonephritis or perinephric abscesses (Monurol® Package Insert. Forest Pharmaceuticals, St Louis, Mo.: 2007). Therefore, neither nitrofurantoin nor fosfomycin are suitable for the treatment of urinary tract infections in a significant proportion of patients with ESBL-producing Enterobacteriaceae.

Other potential oral formulations are not likely to satisfy the need for oral antibiotics active against ESBL-producing Enterobacteriaceae, including those that cause UTI. Oral use of antibiotics of the penem class, such as an orally administered carbapenem tebipenem, could potentially drive increases in carbapenem resistance, especially in the community setting. Oral antibiotics with activity against carbapenemase producers may not be appropriate for use against ESBL-producers that lack carbapenemases (the vast majority of isolates today), especially if they have the potential to select for resistance to the other intravenous agents used in the treatment of carbapenem-resistant Enterobacteriaceae (CRE) (e.g. ceftazidime/avibactam). Fluoroquinolone antibiotics, such as delafloxacin and finafloxacin, are not anticipated to cover ESBL-producing strains, since approximately 70% of such strains are non-susceptible to fluoroquinolones. Further, certain antibiotics, such as certain fluoroquinolones, are associated with an adverse safety profile that could render them unsuitable unless no other treatment options are available. In some aspects, potential oral antibiotics do not result in adequate systemic exposures following feasible oral doses to achieve their PK/PD targets in human. Accordingly, there is no effective oral therapy for the treatment of bacterial infections associated with or caused by ESBL-producing Enterobacteriaceae, such as urinary tract infections.

Only intravenous drugs, such as certain aminoglycosides (amikacin), carbapenems (impenem, meropenem and doripenem), colistin and tigecycline are reliably active against ESBL-producing Enterobacteriaceae (Table 1). Therefore, patients are often hospitalized to receive intravenous therapy such as carbapenems, despite data showing that many of these infections could be adequately treated with oral antibiotics, if such were effectively available, in the setting of susceptible pathogens (Mombelli et al. (1999) Arch Intern Med, 159:53-58) and physicians' desire to offer oral step-down therapy and shorten the length of stay. Unnecessary hospitalization for intravenous therapy has a negative impact on a patient's day-to-day functioning, is costly, and is associated with an increased likelihood of acquiring a nosocomial infection or iatrogenic injury (Pittet et al. (1994) JAMA, 271:1598-1601; Brown et al. (2005) Pharmacoeconomics, 23:1123-1142; Maki et al. (2006) Mayo Clin Proc, 81:1159-1171). In keeping with this observation, the acquisition of a urinary tract infection due to an ESBL-producing pathogen has been associated with higher overall costs of healthcare, and worse outcomes in multiple health economic outcome research analyses (MacVane et al. (2014) J Hosp Med, 9:232-238; Maslikowska et al. (2016) J Hosp Infect, 92:33-41; Esteve-Palau et al. (2015) J Infect, 71:667-674). For example, with the lack of effective oral options, the number of U.S. patients who require hospitalization to treat infections due to ESBL-producing Enterobacteriaceae increased 2.4-fold from 2000 to 2009 (Zilberberg et al. (2013) Infect. Control Hosp Epidemiol, 34:940-6).

In some aspects, intravenous antibiotics are employed for treatment of UTI due to the potential for resistance to oral antibiotic therapy. In some aspects, cUTI is often treated with a carbapenem, which may not be an ideal option because, for example, the increasing use of carbapenems may be a factor in driving the dissemination of carbapenem-resistant Enterobacteriaceae (Swaminathan et al. (2013) Infect. Control. Hosp. Epidemiol., 34:809-17). For example, in 2014 approximately 350,000 patients were treated with carbapenems for a UTI compared to 60,000 patients in 2004 (Decisions Research Group Arlington Medical Resources (AMR) Hospital Antibiotic Market Guide. Burlingon, Mass.: Decision Resources Group; 2016).

Therefore, new oral drugs are needed for the treatment of these multi-drug resistant infections due to Enterobacteriaceae. In some aspects, a new oral antibiotic effective to treat UTI, including cUTI, and/or bacterial infections caused by or associated with ESBL-producing Enterobacteriaceae would reduce the burden and cost of hospitalization, spare carbapenem use, reduce the complications associated with the use of IV catheters and minimize the risk of oral antibiotic treatment failure. Further, in the setting of the intentional dissemination of pathogenic bacteria, including dissemination of bacteria that have been engineered to produce ESBLs, the lack of an effective oral agent for post-exposure prophylaxis could result in many deaths and the overburdening of IV treatment centers.

The provided combination therapy involving combined administration of ceftibuten, such as a pharmaceutically acceptable salt or hydrate thereof, and clavulanic acid, such as a pharmaceutically acceptable salt, addresses the need for an oral agent that is effective against difficult to treat or multi-resistant bacterial infection, such as cUTI or acute pyelonephritis, and/or bacterial infections caused by or associated with ESBL-producing Enterobacteriaceae. In combination, it is found that the two agents are particularly effective as oral agents against ESBL-producing Enterobacteriaceae, which is not achieved by oral administration of either agent alone or in combination with other drugs.

Oral ceftibuten, as a single agent, is currently approved in the US for the treatment of bacterial infections such as acute bacterial exacerbations of chronic bronchitis, acute bacterial otitis media, and pharyngitis and tonsillitis. Ceftibuten is not indicated for the treatment of urinary tract infections (complicated or uncomplicated) or acute pyelonephritis, which is a focus indication of the provided disclosure. Clavulanate is currently approved in combination with amoxicillin or ticarcillin for a variety of bacterial infection types, including urinary tract infections. However, contemporary ESBL-producing Enterobacteriaceae shown high levels of resistance to penicillin-clavulanate combination products, such as due to the resistance liabilities of penicillins.

As illustrated herein, currently approved orally-bioavailable third-generation cephalosporins alone (e.g. cefixime, cefpodoxime, and ceftibuten) and penicillin/β-lactamase inhibitor combinations (e.g. amoxicillin+clavulanate) are not active against Enterobacteriaceae that produce contemporary ESBLs, such as CTX-M-15 and/or CTX-M-14. The majority (70-90%) of clinical Enterobacteriaceae isolates with an ESBL-phenotype in the US express the CTX-M-15 and/or CTX-M-14 ESBLs (Doi et al., (2013) Clin Infect Dis, 56:641-648). The lack of activity of cephalosporins against ESBL-producing Enterobacteriaceae is reflected in poor outcomes for patients with infections due to these pathogens who receive definitive therapy with cephalosporins (Paterson et al. (2001) J Clin Microb, 39:2206-2212; Lee et al. (2013) Clin Infect Dis, 56:488-495). Commercially-available combinations of cephalosporins with β-lactamase inhibitors, such as ceftolozane/tazobactam (Expert Opin Drug Metab Toxicol 2016; 7:1-8) and ceftazidime/avibactam (Castanheira et al. (2016) Antimicrob Agents Chemother 60:4770-4777), are reported to be active against ESBL-producing Enterobacteriaceae. However, neither the cephalosporins (ceftolozane or ceftazidime) nor the β-lactamase inhibitors (tazobactam or avibactam) used in these combinations are orally bioavailable. In summary, existing orally bioavailable cephalosporins and penicillin/β-lactamase inhibitor combinations are not active against ESBL-producing Enterobacteriaceae, and existing cephalosporin/β-lactamase inhibitor combinations are active but are not orally-bioavailable.

A combination of an orally-bioavailable third-generation cephalosporin antibiotic (ceftibuten) and a β-lactamase inhibitor (clavulanate), such as in a single, oral formulation (a suspension, capsule, tablet or other form), for the treatment of bacterial infections is disclosed. It is understood that reference to clavulanate refers to any form, including the free acid or salt form. In some embodiments, the β-lactamase inhibitor is clavulanic acid. In some embodiments, the β-lactamase inhibitor is a pharmaceutically acceptable salt of clavulanic acid, such as potassium clavulanate or sodium clavulanate. In some embodiments, the β-lactamase inhibitor is the following compound:

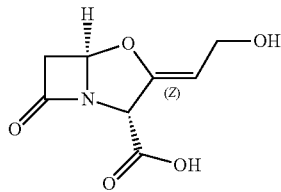 [SMILES: O=C(O)[C@H]1/C(=C/CO)O[C@@H]2CC(=O)N21]

or is a pharmaceutically acceptable salt thereof. It is understood that ceftibuten can be a pharmaceutically acceptable salt or hydrate thereof. In some embodiments, the cephalosporin antibiotic is a pharmaceutically acceptable salt of ceftibuten. In some embodiments, the cephalosporin antibiotic is a hydrate of ceftibuten. In some embodiments, the cephalosporin antibiotic is the following compound:

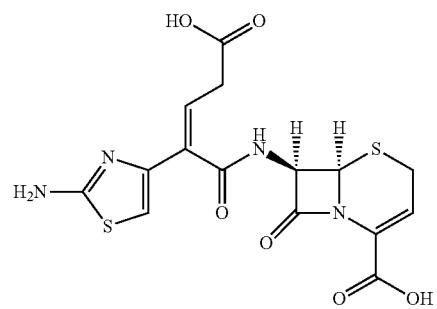 [SMILES: Nc1nc(/C(=C/CC(=O)O)C(=O)N[C@@H]2C(=O)N3C(C(=O)O)=CCS[C@H]23)cs1]

or is a pharmaceutically acceptable salt or hydrate thereof. In some embodiments, the cephalosporin antibiotic is ceftibuten dihydrate.

The provided combination provides an oral treatment option for urinary tract infections caused by Enterobacteriaceae, with activity against ESBL-producing Enterobacteriaceae, which is distinct from existing prior art treatments. Cephalosporins and clavulanate have not been developed in combination previously, due, for example, to: a) the lack of perceived activity of cephalosporins, such as ceftibuten, against contemporary pathogens (Pulcini et al. (2012) Clin Infect Dis, 54:268-274), and b) observations that clavulanate has a short exposure time due to its rapid clearance (Excerpta Medica, International Congress Series 544; 1980, pages 117-121), and higher doses are borderline intolerable (Ball et al. (1980) Lancet, 1(8169):620-623), which would lead one to assume that the PK/PD target for efficacy could not be met. Prior to the observations herein, there was a lack of post-β-lactamase inhibitor effects (PBLIE) data supporting a sustained effect of a cephalosporin+clavulanate against a contemporary ESBL-producing Enterobacteriaceae.

As shown in the in vitro minimum inhibitory concentration (MIC) and post-β-lactamase inhibitor effects (PBLIE) experiments described below, and the associated pharmacokinetic/pharmacodynamic (PK/PD) analyses, the addition of clavulanate to ceftibuten demonstrates activity against bacterial isolates shown to be resistant to ceftibuten alone. As demonstrated by MIC data, the activity of the combination of ceftibuten and clavulanate was particularly effective against isolates containing the most common β-lactamase genes, such as CTX-M enzymes. In addition, the in vitro MIC experiment shows that the addition of clavulanate to ceftibuten has activity against bacterial pathogens that confer resistance to the combination of clavulanate with amoxicillin. In other words, the specific combination of ceftibuten and clavulanate has activity beyond that which would be predicted from the activity of ceftibuten alone or clavulanate in combination with amoxicillin.

The data herein illustrate the unique pharmacological and pharmacokinetic properties of ceftibuten and the combination of ceftibuten and clavulanate, with respect to their activity against ESBL-producing Enterobacteriaceae. Compared to other cephalosporin and clavulanate combinations, the combination of ceftibuten and clavulanate yielded substantially higher antibacterial potency than other combinations, including enhanced activity against ESBL-producing bacteria as compared to other cephalosporin-clavulanate combinations. The finding, in some aspects, may be attributed to a long post-beta lactamase inhibitor effect (PBLIE) of the combination, thereby resulting in persistent inhibition of a β-lactamase after brief exposure to a beta lactamase inhibitor. In particular, the combination of ceftibuten and clavulanate demonstrated a markedly longer PBLIE than the corresponding post-antibiotic effect (PAE) of ceftibuten alone, indicating that clavulanate effectively protects ceftibuten from hydrolysis by contemporary ESBLs and that this effect extends beyond the period when clavulanate concentrations are above a threshold concentration. The results herein show that the combination of ceftibuten and clavulanate, compared to other cephalosporin and clavulanate combinations, results in a longer duration of clavulanate to inhibit the β-lactamase enzyme, and, thus, longer protection of the ceftibuten β-lactam to result in bacterial killing. Moreover, the PBLIE data show for the first time that the combination of ceftibuten+clavulanate is likely to be effective against common, contemporary ESBL-producing Enterobacteriaceae with feasible dosing regimens. As demonstrated from the PK/PD analysis, an exemplary human dose includes a divided daily dose of ceftibuten and clavulanate each given two to three times a day, such as for a plurality of days, e.g. up to 14 days or more, such as 7-10 days. In some embodiments, ceftibuten is administered orally at a total daily dose of 800 to 1800 mg, such as a total daily dose of 900 to 1200 mg, e.g. given as 300-400 mg BID or TID, and clavulanate is administered orally at a total daily dose of 250 to 750 mg, such as a total daily dose of 375 to 562.5 mg, e.g. given 100-250 mg or 125 to 187.5 mg BID or TID. This supports a finding that the specific combination of ceftibuten+clavulanate is superior to other existing orally-bioavailable cephalosporin+β-lactamase inhibitor combinations, and is likely to meet its PK/PD target and be efficacious.

In some embodiments, provided are compositions including ceftibuten and clavulanate, including pharmaceutical compositions and formulations, and methods of using and uses of the agents and compositions, such as for the treatment of bacterial infections. In some embodiments, ceftibuten and clavulanate may be combined in formulations that are altered compared to currently available doses and dosing regimens of ceftibuten or clavulanate (as it is currently used in combination with amoxicillin, ticarcillin or any other antibiotic). For example, ceftibuten alone is approved for clinical use at a dose of 400 mg a day (once daily (QD)). In some embodiments, the formulations of ceftibuten and clavulanate, such as formulated together or separately, include, but are not limited to, extended release formulations or other specific formulations that allow for decreased frequency of dosing (for example once or twice daily dosing) and/or for increased and/or decreased amount of total daily ceftibuten and/or clavulanate administered.

In some embodiments, the methods of using and uses of the agents and compositions are for treatment of bacterial infections. In some embodiments, the treatment is of urinary tract infections including complicated urinary tract infections, uncomplicated urinary tract infections and acute pyelonephritis caused by, but not limited to, species of the Enterobacteriaceae family. However, in some embodiments, this combination also has utility in the treatment of bacterial infections in other body sites and/or caused by other bacterial species. In some embodiments, the provided combination has use against pathogens that are susceptible to other antibiotics and also those that produce β-lactamase enzymes that degrade antibiotics of the β-lactam class, which includes cephalosporins such as ceftibuten.

Thus, the provided ceftibuten and clavulanate combination offer various advantages over the currently available oral third-generation cephalosporins (e.g. ceftibuten, cefixime or cefpodoxime alone), clavulanate containing oral combinations (e.g. amoxicillin with clavulanate), as well as the alternative cephalosporin and clavulanate combinations that were considered. In some aspects, the ability to administer clavulanate and ceftibuten orally permits administration in an outpatient setting, including allowing administration of dosage forms (e.g. tablets or captures) that are relatively simple to self-administer. In some aspects, this addresses needs in the hospital setting and also for hospital avoidance in the community setting. In some aspects, the provided combination of clavulanate and ceftibuten also provides an option to address problems with resistance to other antibiotics, including overcoming threats caused by engineering resistance in bacteria. In some embodiments, the provided combination offers an alternative to carbapenem use, which, in some aspects, could limit spread of carbapenem resistance. In some embodiments, the provided orally available combination therapy with ceftibuten and clavulanate also could be used in prophylactic methods, such as to provide post-exposure prophylaxis and/or treatment regimens to protect at-risk civilian populations, such as in connection with a bioterror attack.

III. PHARMACEUTICAL COMPOSITIONS AND FORMULATIONS

Provided herein are pharmaceutical compositions containing (a) ceftibuten or a pharmaceutically acceptable form thereof, such as a pharmaceutically acceptable salt or hydrate (hereinafter also called "component (a)") and/or containing (b) clavulanic acid or a pharmaceutically acceptable form thereof, such as a pharmaceutically acceptable salt thereof (hereinafter also called "component (b)"). In some embodiments, component (a) and component (b) are formulated as separate pharmaceutical compositions, such as for use in accord with the provided articles of manufacture or for use for administration to an individual simultaneously or concurrently in accord with the provided methods and uses. In some embodiments, component (a) and component (b) are formulated together, such as for use in accord with the provided articles of manufacture or for use for administration to an individual as a single composition in accord with the provided methods and uses.

A person skilled in the art knows that various chemical and polymorphic forms of a compound exist and any form are contemplated for ceftibuten or clavulanic acid in the compositions provided herein. In some embodiments, ceftibuten can be in its free form or in the form of its pharmaceutically acceptable salts, ester, solvate or hydrate thereof. In some embodiments, the hydrate is a monohydrate form, dihydrate form or trihydrate form. In some embodiments, clavulanic acid can be in its free form or the form of its pharmaceutically acceptable salts or esters.

In some embodiments, component (a) and/or component (b) is a pharmaceutically acceptable salt. In some embodiments, a pharmaceutically acceptable salt is one or more salts of a given compound which possesses desired pharmacological activity of the free compound and which is neither biologically nor otherwise undesirable. In some embodiments, a pharmaceutically acceptable salt includes a salt with an inorganic base, organic base, inorganic acid, organic acid, or basic or acidic amino acid. In some aspects, salts of inorganic bases includes, for example, alkali metals such as sodium or potassium; alkaline earth metals such as calcium and magnesium or aluminum; and ammonia. In some aspects, salts of organic bases includes, for example, trimethylamine, triethylamine, pyridine, picoline, ethanolamine, diethanolamine, and triethanolamine. In some aspects, salts of inorganic acids includes, for example, hydrochloric acid, hydroboric acid, nitric acid, sulfuric acid, and phosphoric acid. In some aspects, salts of organic acids includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. In some aspects, salts of basic amino acids includes, for example, arginine, lysine and ornithine. Acidic amino acids include, for example, aspartic acid and glutamic acid.

In certain embodiments, component (a) is ceftibuten or a pharmaceutically acceptable salt thereof, or a hydrate of the foregoing. In certain embodiments, component (a) comprises a hydrate. In certain embodiments, component (a) comprises a pharmaceutically acceptable salt. In certain embodiments, component (a) is ceftibuten dihydrate. In certain embodiments, component (b) is clavulanic acid, or a pharmaceutically acceptable salt thereof. In certain embodiments, component (b) comprises a pharmaceutically acceptable salt. In certain embodiments, the salt is sodium or potassium. In certain embodiments, component (b) is potassium clavulanate. In certain embodiments, component (a) is ceftibuten dihydrate and component (b) is potassium clavulanate.

In some embodiments, the pharmaceutical composition contains a therapeutically effective amount of component (a) and/or component (b) formulated together with one or more pharmaceutically acceptable carriers. In some embodiments, the pharmaceutically acceptable carrier is a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Generally, components (a) and component (b) are formulated for oral administration and administered orally. The pharmaceutical compositions can be formulated for oral administration to an individual, such as to a human or other animal. Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

In some embodiments, solid compositions of a similar type may also be employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In some embodiments, solid compositions of a similar type may also be employed as fillers in soft and hard-filled gelatin capsules using such excipients as lactose or milk sugar as well as high molecular weight polyethylene glycols.

In some embodiments, the active agent(s) can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In some embodiments, component (a) and component (b) are administered orally as soft gel capsules containing liquid. In some embodiments, component (a) and component (b) are administered as a liquid dosage form, such as oral suspensions, syrups or elixirs. In some aspects, liquid dosage forms for oral administration may be provided wherein each dosage unit, for example, teaspoonful, tablespoonful, milliliter, and the like, contains a predetermined amount of the composition containing component (a) and/or component (b).

In some embodiments, the pharmaceutical composition is formulated in a unit dosage form. In some aspects, a unit dosage form is a physically discrete unit suitable as a unitary dosage for human subjects and other mammals in which each unit contains an effective amount of component (a) and/or component (b) or a fraction thereof for administration as a divided dose of a total daily dose. In some embodiments, the pharmaceutical composition, including a unit dosage form is suitable for oral administration. In some embodiments, exemplary, non-limiting unit dosage forms include a tablet (e.g., a chewable tablet), caplet, capsule (e.g., a hard capsule or a soft capsule), lozenge, film, strip, gelcap, and syrup. Pharmaceutical formulations and unit dose forms suitable for oral administration are particularly useful for administration on an outpatient basis and/or in which the individual (patient) self-administers the agents.

In some embodiments, component (a) and component (b) may be administered separately (as separate unit dosage forms) or may be combined in an oral unit dosage form that comprises both component (a) and component (b) for use in the practice of the methods described herein. In some aspects, when administered as separate unit forms, typically the component (a) and component (b) doses are administered (e.g. self-administered) at about the same time, e.g. simultaneously or within about no more than 60 minute of each other, such as within or about within 3 minutes, 5 minutes, 10 minutes, 15 minutes or 30 minutes of each other.

In certain embodiments, component (a) and component (b) are formulated, such as in unit dosage forms, for administration to the individual of component (a) at a ratio to component (b) of between about 1:1-7:1, such as between about 1:1 and about 6:1, 5:1, 4:1, 3:1, or 2:1. In some embodiments, component (a) is administered to the individual at a ratio of 1:1 to 4:1. In certain embodiments, component (a) is administered to the individual at a ratio to component (b) of between 1:1-3:1. In some embodiments, component (a) is administered to the individual at a ratio to component (b) of or about 1:1-2:1. In some embodiments, component (a) is administered to the individual at a ratio to component (b) of 2:1-4:1. In some embodiments, component (a) is administered to the individual at a ratio to component (b) of 2:1-3:1. In some embodiments, component (a) and component (b) are delivered to the individual in the same unit dosage form (i.e., "co-formulated"). For example, a dosage form may contain component (a) and component (b) and a pharmaceutically acceptable carrier, such as excipients or auxiliary agents. In some embodiments, a unit dosage form or pharmaceutical composition containing component (a) and component (b) are formulated for administration (e.g. oral administration) and contain component (a) at a ratio to component (b) of between 1:1-7:1, such as between about 1:1 and about 6:1, 5:1, 4:1, 3:1, or 2:1. In certain embodiments, component (a) is formulated for administration (e.g. oral administration) to the individual at a ratio to component (b) of between 1:1-3:1. In certain embodiments, component (a) is present in the pharmaceutical composition or unit dosage form at a molar ratio to component (b) of between about 1:1 and about 10:1, such as, between about 1:1 and 9:1, 8:1, 7:1, 6:1, 5:1, 4:1, or 3:1.

In certain embodiments, the pharmaceutical composition, such as a unit dosage form, comprises between about 150-600 mg of component (a), such as between about 150-400, 200-400, or 300-400 mg of component (a). In certain embodiments, the pharmaceutical composition, such as a unit dosage form, comprises between about 50-250 mg of component (b), such as between about 50-250 mg, 100-200 mg, or 125-187.5 mg of component (b). In some embodiments, the amount of component (a) and component (b) are present in separate pharmaceutical compositions. In some embodiments, the amount of component (a) and component (b) are formulated together in the same pharmaceutical composition.

In some embodiments, two or more unit dosage forms are administered per dose, such as per a divided dose of a total daily dose. For example, in some embodiments, a unit dosage form (e.g. oral dosage forms, such as a capsule) of component (a) (ceftibuten) contains between about 50 and 250 mg, such as 100 mg and 200 mg, each inclusive, e.g. at about 100 mg or about 200 mg. In such embodiments, a divided dose of component (a) is administered as 1, 2, 3 or 4 unit dosage forms. In some embodiments, a unit dosage form of (e.g. oral dosage form, such as a capsule) of component (b) (e.g. clavulanic acid) contains between about 50 mg and 150 mg, such as 62.5 mg and 125 mg, each inclusive, e.g. at about 62.5 mg or about 125 mg. In some embodiments, a divided dose of component (b) is administered as 1, 2, 3 or 4 unit dosage forms. In some embodiments, the amount of component (a) and component (b) are present in separate pharmaceutical compositions. In some embodiments, the amount of component (a) and component (b) are formulated together in the same pharmaceutical composition.

In certain embodiments, the pharmaceutical composition is suitable for oral, mucosal (including sublingual, buccal, rectal, nasal, or vaginal) or parenteral (including subcutaneous, intramuscular, bolus injection, intraarterial, or intravenous) administration. In some embodiments, the pharmaceutical composition is suitable for oral administration. In some embodiments, the pharmaceutical composition is formulated as a capsule, solutab, sachet, suspension, or tablet. In some embodiments, the divided dose is formulated as 1, 2, 3, or 4 capsules, solutabs, sachets, suspensions, or tablets. In some embodiments, one or both of components (a) and (b) are formulated as a capsule. Capsules can be standard or non-standard sizes. In some embodiments, the capsule is size 0, 1, or 2.

In certain embodiments, the pharmaceutical composition is a suspension. In certain embodiments, the suspension is flavored. In certain embodiments, the suspension is for use in an individual who is less than about 18, such as less than about 16, 14, 12, 10, 8, 6, 5, 4, 3, 2, 1 years old.

IV. METHODS OF USE AND USES

Provided herein are methods of treating or prophylaxis of a bacterial infection in an individual, wherein the method comprises administering to the individual (a) ceftibuten or a pharmaceutically acceptable form thereof, such as a pharmaceutically acceptable salt, ester, solvate or hydrate thereof and/or containing (b) clavulanic acid or a pharmaceutically acceptable form thereof, such as a pharmaceutically acceptable salt or ester thereof. In some embodiments, the methods of treating or prophylaxis of a bacterial infection in an individual include administering to the individual (a) ceftibuten or a pharmaceutically acceptable salt thereof, or a hydrate of the foregoing; and (b) clavulanic acid, or a pharmaceutically acceptable salt thereof. In some embodiments, such methods and uses include therapeutic methods and uses, for example, involving administration of the components to an individual having, or suspected of or likely having, a bacterial infection. In some embodiments, such methods and uses include prophylactic methods and uses, for example, involving administration of the components to an individual at risk of, or suspected of being or likely of being at risk of, exposure to a bacterium that is associated or causes a bacterial infection.

In some embodiments, components (a) and/or (b) are formulated as a pharmaceutical composition. In some embodiments, the pharmaceutical composition is a pharmaceutical composition described herein. In some embodiments, the method comprises administering a pharmaceutical composition comprising components (a) and/or (b). In some embodiments of the provided methods, components (a) and/or (b) may be suitable for oral, mucosal (including sublingual, buccal, rectal, nasal, or vaginal) or parenteral (including subcutaneous, intramuscular, bolus injection, intraarterial, or intravenous) administration. In some embodiments, component (a) is administered orally. In some embodiments, component (b) is administered orally. In some embodiments, components (a) and (b) are administered orally. In some embodiments, one or both of components (a) and (b) are formulated as a capsule, solutab, sachet, suspension, or tablet. In some embodiments, components (a) and components (b) are administered in a total daily dose containing one or more divided dose, wherein the divided dose is formulated as 1, 2, 3, or 4 capsules, solutabs, sachets, suspensions, or tablets. In some embodiments, one or both of components (a) and (b) are formulated as a capsule. Capsules can be standard or non-standard sizes. In some embodiments, the capsule is size 0, 1, or 2. In some embodiments, one or both of components (a) and (b) are formulated for modified or extended release.

In some embodiments, components (a) and (b) are administered in an effective amount to effect the therapeutic or prophylactic treatment of the bacterial infection. Uses include uses of the component (a) and component (b), or the composition or compositions containing such components, in such methods and treatments, and in the preparation of a medicament in order to carry out such therapeutic and prophylactic methods. In some embodiments, the therapeutic methods treat the bacterial infection in the individual or prevent or reduce the risk of the bacterial infection in the individual.

Among the provided methods for using and uses are methods of treating a bacterial infection, such as an Enterobacteriaceae bacterial infection, in an individual in need of such treatment, wherein the method comprises administering to an individual (a) ceftibuten or a pharmaceutically acceptable salt thereof, or a hydrate of the foregoing; and (b) clavulanic acid, or a pharmaceutically acceptable salt thereof. In some embodiments, the method is for treating an individual that exhibits one or more signs or symptoms of the bacterial infection or is suspected or known to have the bacterial infection. In some embodiments, the method is for treating an individual having a urinary tract infection (UTI), such as a complicated urinary tract infection (cUTI), acute pyelonephritis, uncomplicated UTI (uUTI), acute pyelonephritis, upper respiratory infection, lower respiratory tract infection, primary or catheter-associated blood infection, neonatal sepsis, intra-abdominal infection, otitis media, or a wound infection. In some embodiments, the method is for treating an individual having or suspected of having complicated urinary tract infection (cUTI), acute pyelonephritis, uncomplicated UTI (uUTI), complicated intra-abdominal infection (cIAI) or community acquired pneumonia (CAP). In some embodiments, the individual is known or suspected of or is likely to have a bacterial infection that is caused or associated with a bacterium that expresses an extended-spectrum-β-lactamase (ESBL). In some embodiments, the bacterial infection is one that is likely to be associated with a bacterium that expresses an ESBL, such as is one in which it is known that, on average in a population of individuals having the infection, the infection is caused by or associated with an ESBL-producing bacteria in greater than or about 10% of such individuals, such as greater than or about 20%, greater than or about 30%, greater than or about 40%, greater than or about 50%, greater than or about 60%, greater than or about 70%, greater than or about 80%, greater than or about 90% or more of the individuals. In some embodiments, the subject is selected or identified as having a bacterial infection with an ESBL-producing bacteria.

In one aspect, there is provided a method of using or uses of components (a) and/or (b) for treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, wherein the bacterial infection is a urinary tract infection (UTI), upper respiratory infection, lower respiratory tract infection, primary or catheter-associated blood infection, secondary blood infection with a UTI source, neonatal sepsis, intra-abdominal infection, otitis media or a wound infection. In some embodiments, the bacterial infection is complicated urinary tract infection, uncomplicated urinary tract infection and acute pyelonephritis. In some embodiments, the bacterial infection is associated with or caused by, or is likely to be associated with or caused by, a bacterium that expresses an extended-spectrum-β-lactamase (ESBL). In certain embodiments, the bacterial infection is a hospital-associated or a community-acquired infection.

In certain embodiments, the bacterial infection is associated with two or more strains of bacteria. In certain embodiments, one or more of the two or more strains of bacteria is a bacterium described herein. In certain embodiments, one or more of the two or more strains of bacteria expresses an extended-spectrum-β-lactamase (ESBL).

In some embodiments, the method is for prophylaxis of an individual that is at risk of exposure to a bacterial infection or who has or has likely been exposed to the bacterial infection. Among the provided methods of using and uses are prophylactic methods, such as to prevent, reduce or ameliorate the risk of a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof. In certain embodiments, one or both of component (a) and (b) are administered after the individual has been or has likely been exposed to a bacterium associated with the bacterial infection. In certain embodiments, the bacterium expresses an extended-spectrum-β-lactamase (ESBL).

In another aspect, there is provided a method of using or uses of components (a) and/or (b) for treating a bacterial infection in an individual or for preventing, reducing or ameliorating a risk of a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with a bacterium, or is likely to be associated with a bacterium that expresses an extended-spectrum-β-lactamase (ESBL). In some embodiments, the bacterial infection is associated with, or likely to be associated with, a bacterium that expresses an extended-spectrum-β-lactamase (ESBL) that is or is believed to be CTX-M-14 or CTX-M-15.

In another aspect, there is provided a method of using or uses of components (a) and/or (b) for treating a bacterial infection in an individual or for preventing, reducing or ameliorating a risk of a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with a bacterium that expresses an extended-spectrum-β-lactamase (ESBL), and wherein the individual was previously administered an antibiotic to treat the bacterial infection.

In some embodiments, the individual is a mammal. In some embodiments the individual is a human, primate, cow, goat, sheep, pig, horse, cat, dog, or rodent. In some embodiments, the individual is human. In some embodiments, the individual is a domestic animal. In some embodiments, the individual is an agricultural animal.

In some embodiments of any of the methods or uses described herein, an individual who has been diagnosed with or is suspected of having a bacterial infection can be treated. In some embodiments, the individual shows one or more symptom of an infection. In some embodiments, the symptom of an infection is pain, fever, drainage, redness, swelling, sleepiness, headache, cough, chest pain, or trouble breathing. In some embodiments, the individual tested positive for a bacterial infection. Whether an individual is positive for a bacterial infection can be determined by one of skill in the art. The presence of a bacterial infection can be determined, for example, by culture, PCR, ELISA, sequencing, or microarray analysis.

In some embodiments, the individual is human. In some embodiments, the individual is at least about or is about any of 21, 25, 30, 35, 40, 45, 50, 55, 60, 65, 70, 75, 80, or 85 years old. In some embodiments, the individual is a child. In some embodiments, the individual is less than about or about any of 21, 18, 15, 12, 10, 8, 6, 5, 4, 3, 2, or 1 years old. In some embodiments, the individual is male. In some embodiments, the individual is a female. In some embodiments, the individual has any of the types of bacterial infections described herein.

In some embodiments, the individual was previously administered an antibiotic to treat the bacterial infection. In some embodiments, the previously administered antibiotic was a beta-lactam or a fluoroquinolone.

In some embodiments, the previously administered antibiotic was a beta-lactam which was a penicillin derivative, cephalosporin, monobactam, or carbapenem. In some embodiments, the previously administered antibiotic was a beta-lactam which was amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, doripenem, gentamicin, imipenem, loracarbef, meropenem, piperacillin, or tobramycin.

In some embodiments, the previously administered antibiotic was a beta-lactam that was administered with a beta-lactamase inhibitor. In some embodiments, the previously administered beta-lactamase inhibitor was clavulanate, tazobactam, avibactam, or sulbactam.

In some embodiments, the previously administered antibiotic was a fluoroquinolone which was levofloxacin, delafloxacin, finafloxacin, or ciprofloxacin.

In some embodiments, wherein the previously administered antibiotic was not fully effective at treating the bacterial infection. In some embodiments, the bacterial infection is a recurrent bacterial infection. In some embodiments, the previously administered antibiotic was not effective in treating the bacterial infection.

In some embodiments, the previously administered antibiotic was an intravenously administered antibiotic or an orally administer antibiotic. In some embodiments, the previously administered antibiotic was an intravenously administered antibiotic.

In some embodiments, components (a) and (b) are administered orally, and the oral administration of component (a) and (b) is a step-down therapy or is the oral portion of an intravenous to oral therapy switch.

In certain embodiments, one or both of component (a) and (b) are administered on an outpatient basis. In certain embodiments, one or both of component (a) and (b) are self-administered by the individual.

In certain embodiments, component (a) is ceftibuten or a pharmaceutically acceptable salt there, or a hydrate of the foregoing. In certain embodiments, component (a) comprises a hydrate. In certain embodiments, component (a) comprises a pharmaceutically acceptable salt. In certain embodiments, component (a) is ceftibuten dihydrate.

In certain embodiments, component (b) is clavulanic acid, or a pharmaceutically acceptable salt thereof. In certain embodiments, component (b) comprises a pharmaceutically acceptable salt. In certain embodiments, the salt is sodium or potassium. In certain embodiments, component (b) is potassium clavulanate. In certain embodiments, component (a) is ceftibuten dihydrate and component (b) is potassium clavulanate.

In certain embodiments, component (a) is administered to the individual at a ratio to component (b) of between about 1:1-7:1, such as between about 1:1 and about 6:1, 5:1, 4:1, 3:1, or 2:1. In certain embodiments, component (a) is administered to the individual at a ratio to component (b) of 1:1-3:1. In some embodiments, component (a) is administered to the individual at a ratio to component (b) of or about 1:1-2:1. In some embodiments, component (a) is administered to the individual at a ratio to component (b) of 2:1-4:1. In some embodiments, component (a) is administered to the individual at a ratio to component (b) of 2:1-3:1.

In some embodiments, the components (a) and (b) are sequentially administered, concurrently administered or simultaneously administered. In certain embodiments, components (a) and (b) are administered with a time separation of no more than about 15 minutes, such as no more than about any of 10, 5, or 1 minutes. In certain embodiments, components (a) and (b) are administered with a time separation of more than about 15 minutes, such as more than about any of 20, 30, 40, 50, 60, or more minutes. Either component (a) or component (b) may be administered first. In certain embodiments, components (a) and (b) are administered simultaneously. In certain embodiments, components (a) and (b) are administered together in the same pharmaceutical composition.

Individuals may receive combined administration of component (a) and component (b) for a predetermined time, an indefinite time or until an endpoint is reached. In some embodiments, treatment may be continued on a continuous daily basis for days, weeks or months. In some embodiments, treatment is continued until administration is effective to reduce the bacterial infection and/or at which time the bacterial infection is no longer detected or present. In accord with the provided methods, components (a) and (b) are administered, for a period of time, such as for consecutive days, until the bacterial infection is treated and/or until there is a reduction or decrease in one or more sign or symptom of the bacterial infection. In some embodiments, such as in connection with prophylactic methods, components (a) and (b) are administered for a period of time, such as for consecutive days, until the risk of the bacterial infection is reduced, prevented or ameliorated.

In certain embodiments, one or both of component (a) and component (b) are administered for at least about 3 days, such as at least about 4, 5, 6, 7, 8, 9, 10, 11, 12, 13, 14, 15, or 20 days. In certain embodiments, one or both of component (a) and component (b) are administered for from about 3 days to about 20 days, such as from about 3 days and about 20, 15, 14, 13, 12, 11, 10, 9, 8, 7, 6, 5, or 4 days, or from about 5 days and about 20, 15, 14, 13, 12, 11, 10, 9, 8, 7, or 6 days, or between about 7 days and about 20, 15, 14, 13, 12, 11, 10, 9, or 8 days. In certain embodiments, one or both of component (a) and component (b) are administered for from about 7 days to about 10 days. In certain embodiments, one or both of component (a) and component (b) are administered for about 3, 4, 5, 6, 7, 8, 9, 10, 11, 12, 13, 14, 15, 16, 17, 18, 19 or 20 days. In certain embodiments, one or both of component (a) and component (b) are administered for 7 to 10 days. In any of such embodiments, components (a) and component (b) are administered daily for consecutive days.

In some embodiments, treatment may be discontinued or suspended after the predetermined number of days or a specified endpoint, such as the reduction in a sign or symptom of the bacterial infection and/or the absence of detectable infection in the individual. In some embodiments, treatment is discontinued and suspended unless and until the bacterial infection returns to detectable levels and/or the individual exhibits one or more signs or symptoms of the bacterial infection.

In some embodiments, the method involves administering to the individual a therapeutically effective amount of component (a) and/or component (b) for the therapeutic or prophylactic treatment of a bacterial infection. In some aspects, the total daily dose administered for the therapeutic or prophylactic treatment of a particular bacterial infection will vary depending on the host treated, the route of administration and the severity of the illness being treated. Accordingly, the optimum dosage may be determined by the practitioner who is treating any particular patient. For example, it may be necessary or desirable to reduce the above-mentioned doses of the treatment in order to reduce toxicity.

In some embodiments, the provided methods involve administering to an individual, such as a human, component (a) in a total daily dose of about 500 mg-2000 mg, such as about 900, 800, 700 mg, or about 800 to about 1800, 1600, 1500, 1400, 1300, 1200, 1100, 1000, or 900 mg, or about 900 to about 1800, 1600, 1500, 1400, 1300, 1200, 1100, or 1000 mg, or about 1200 to about 1800, 1600, 1500, 1400, or 1300 mg. In some embodiments, the total daily dose is about 600 to 1800 mg, 600 to 1600 mg, 600 to 1400 mg, 600 to 1200 mg, 600 to 1000 mg, 600 to 900 mg, 600 to 800 mg, 800 mg to 2000 mg, 800 mg to 1800 mg, 800 mg to 1600 mg, 800 mg to 1400 mg, 800 mg to 1200 mg, 800 mg to 1000 mg, 800 to 900 mg, 900 to 2000 mg, 900 to 1800 mg, 900 to 1600 mg, 900 to 1400 mg, 900 to 1200 mg, 900 to 1000 mg, 1000 to 2000 mg, 1000 to 1800 mg, 1000 to 1600 mg, 1000 to 1400 mg, 1000 to 1200 mg, 1200 mg to 2000 mg, 1200 mg to 1800 mg, 1200 mg to 1600 mg, 1200 mg to 1400 mg, 1400 mg to 2000 mg, 1400 mg to 1800 mg, 1400 mg to 1600 mg, 1600 mg to 2000 mg, 1600 mg to 1800 mg, or 1800 mg to 2000 mg, each inclusive. In some embodiments, the provided methods involve administering to the individual component (b), such as the human, in a total daily dose of about 250 mg-750 mg, such as about or 375 mg, or about 375 to about 750, 600, 562.5, 500, or 400 mg, or about 500 to about 750, 600, or 562.5 mg, or about 562.5 to about 750 or 600 mg. In some embodiments, the total daily dose is about 250 to 600 mg, 250 to 600 mg, 250 to 500 mg, 250 to 375 mg, 250 to 300 mg, 300 to 750 mg, 300 to 600 mg, 300 to 750 mg, 300 to 600 mg, 300 to 500 mg, 300 to 375 mg, 375 to 750 mg, 375 to 600 mg, 375 to 500 mg, 500 to 750 mg, 500 to 600 mg or 600 to 750 mg, each inclusive. In some embodiments, the total daily dose of component (b) is or is about 375 to 562.5 mg, inclusive, such as is about 375 mg or is about 562.5 mg. In some embodiments, the provided methods involve administering to the individual component (a) in a total daily dose of 800-1800 mg, and administering component (b) in a total daily dose of 250-750 mg. In some embodiments, the provided methods involve administering to the individual component (a) in a total daily dose of 900 to 1200 mg, and administering component (b) in a total daily dose of 375 to 562.5 mg. In some embodiments, components (a) and (b) are administered together at the same time. In some embodiments, components (a) and (b) are formulated for administration together. In some embodiments, components (a) and (b) are formulated as separate compositions for administration separately, such as concurrently or simultaneously.

In some embodiments, the total daily dose of one or both of component (a) and component (b) are administered in one dose or as two or more divided doses. In some aspects, the divided dose is such that the total daily dose to be administered to the individual, such as a human, in any one day period (for example one 24 hour period from midnight to midnight) is divided up into two or more fractions of the total daily dose and these fractions are administered. In some embodiments, the total daily dose is administered in 2-5 divided doses, such that a divided dose is administered 2-5 times per day. In some embodiments, the total daily dose is administered in 2-3 divided doses, such that a divided dose is administered two or three times per day. In some embodiments, component (a) and component (b) is administered BID (two times a day). In some embodiments, component (a) and component (b) is administered TID (three times a day). In some embodiments, the divided dose in a day of component (a) is administered in an amount of 300-400 mg, e.g. at or about 300 mg or 400 mg. In some embodiments, the divided dose in a day of component (b) is administered in an amount of 100-250 mg, such as 125-187.5 mg, e.g. at or about 125 mg or 187.5 mg.

In some embodiments, the method involves administering to an individual, such as a human, ceftibuten in two or three divided doses each containing 300-400 mg, e.g. at or about 400 mg, and administering to the individual, such as the human individual, clavulanic acid in two or three divided doses each containing 100-250 mg, such as 125-187.5 mg, e.g. at or about 125 mg or 187.5 mg.

In some embodiments, the time intervals between divided doses of component (a) and/or component (b) are administered with a time period between each divided dose containing the component of between or between about 0 and 12 hours, such as between about 0 hour and 8 hours, 0 and 6 hours, 0 and 4 hours, 0 and 2 hours, 0 and 1 hours, 1 hour and 12 hours, 1 hour and 8 hours, 1 hour and 6 hours, 1 hour and 4 hours, 1 hour and 2 hours, 2 hours and 12 hours, 2 hours and 8 hours, 2 hours and 6 hours, 2 hours and 4 hours, 4 hours and 12 hours, 4 hours and 8 hours, 4 hours and 6 hours, 6 hours and 12 hours, 6 hours and 8 hours, or 8 hours and 12 hours. In certain embodiments, the divided doses of component (a) and/or component (b) are administered with a time period between each divided dose containing the component of more than about 1 hour, such as more than about any of 2, 3, 4, 5, 6, 7, 8, 9, 10, 11, or 12 hours. In certain embodiments, the divided doses are administered with a time period between each divided dose of no more than about 1 hour, such as no more than about any of 2, 3, 4, 5, 6, 7, 8, 9, 10, 11, or 12 hours. In certain embodiments, the divided doses are administered about every 3 to about every 12 hours, such as about every 3 hours to about every 10, 9, 8, 7, 6, 5, or 4 hours, or about every 4 hours to about every 12, 10, 9, 8, 7, 6, or 5 hours, or about every 6 hours to about every 12, 10, 9, 8, or 7 hours, or about every 8 hours to about every 12, 10, or 9 hours. In certain embodiments, the divided doses are administered about every 3, 4, 6, 8, or 12 hours. In certain embodiments, the divided doses are administered about every 8 or 12 hours.

In some embodiments, each divided dose containing component (a) and/or component (b) comprises the same amount of one or both of component (a) and component (b). In some embodiments, at least one divided dose containing component (a) and/or component (b) comprises a different amount of one or both of component (a) and component (b) compared with a second divided dose given the same day. In some embodiments, the first divided dose administered in a day comprises a smaller amount of one or both of component (a) and component (b) than one or more divided dose(s) administered subsequently in the same day. In some embodiments, the first divided dose administered in a day comprises the smallest amount administered of one or both of component (a) and component (b) in a day.

In some embodiments, the first divided dose administered in a day comprises a larger amount of one or both of component (a) and component (b) than one or more divided dose(s) administered subsequently. In some embodiments, the first divided dose administered in a day comprises the largest amount administered of one or both of component (a) and component (b) in a day. In some embodiments, the first divided dose administered in a day comprises 300 mg of component (a) and one or more subsequent divided dose(s) comprise more than 300 mg. In some embodiments, the first divided dose administered in a day comprises 400 mg of component (a) and one or more subsequent divided dose(s) comprise less than 400 mg. In some embodiments, the first divided dose administered in a day comprises 125 mg of component (b) and one or more subsequent divided dose(s) comprise(s) more than 125 mg. In some embodiments, the first divided dose administered in a day comprises 187.5 mg of component (b) and one or more subsequent divided dose(s) comprise(s) less than 187.5 mg.

In certain embodiments, one or both of component (a) and component (b) are administered with or without food. In certain embodiments, one or both of component (a) and component (b) are administered prior to, with, or subsequent to food. In certain embodiments, the food is to be eaten within about 2 hours, such as within about 1.5 hours, 1.25 hours, 1 hour, 55 minutes, 50 minutes, 45 minutes, 40 minutes, 35 minutes, 30 minutes, or less, of the administration of one or both of component (a) and component (b). In certain embodiments, the food is to be eaten within about 30 minutes of the administration of one or both of component (a) and component (b). In certain embodiments, one or both of component (a) and component (b) are administered without food. In certain embodiments, the food is not to be eaten within about 45 minutes, such as at least about any of 50 minutes, 55 minutes, 1 hour, 1.25 hours, 1.5 hours, 1.75 hours, 2 hours, 3 hours, 4 hours, 5 hours, 6 hours, 7 hours 8 hours, 9 hours, 10 hours, 11 hours, 12 hours or more, of the administration of one or both of component (a) and component (b). In certain embodiments, the food is not to be eaten within about 1 hour of the administration of one or both of component (a) and component (b).

In certain embodiments one or both of component (a) and component (b) are administered before or after food. In certain embodiments, one or both of component (a) and component (b) are administered at least about 30 minutes before food, such as at least about 40 minutes, 45 minutes, 50 minutes, 55 minutes, 1 hour, 1.25 hour, 1.5 hour, 1.75 hour, 2 hours, 3 hours, 4 hours, or 5 hours or at least about 30 minutes after food, such as at least about 40 minutes, 45 minutes, 50 minutes, 55 minutes, 1 hour, 1.25 hour, 1.5 hour, 1.75 hour, 2 hours, 2.25 hours, 2.5 hours, 2.75 hours, 3 hours, 4 hours, or 5 hours. In certain embodiments, one or both of component (a) and component (b) are administered at least 1 hour before food or 2 hours after food.

In certain embodiments, one or both of component (a) and component (b) are administered before food. In certain embodiments, the food is to be eaten within about 2 hours, such as within about any of 1.5 hours, 1.25 hours, 1 hour, 55 minutes, 50 minutes, 45 minutes, 40 minutes, 35 minutes, 30 minutes, or less before administration of one or both of component (a) and component (b) or within about 2 hours, such as within about any of 1.5 hours, 1.25 hours, 1 hour, 55 minutes, 50 minutes, 45 minutes, 40 minutes, 35 minutes, 30 minutes, or less after administration of one or both of component (a) and component (b).

In certain embodiments, the food is high in fat and/or calories. In certain embodiments, the food contains at least about 20%, 25%, 30%, 35%, 40%, 45%, 50%, 55%, 60%, or more of the daily recommended value of fat and/or calories.

In certain embodiments, the bacterial infection is associated with a bacterium that is gram-positive or gram negative. In certain embodiments, the bacterium is Enterobacteriaceae. In certain embodiments, the bacterium is *Acinetobacter, Bdellovibrio, Burkholderia, Chlamydia, Enterobacter, Escherichia, Francisella, Haemophilus, Helicobacter, Klebsiella, Legionella, Moraxella, Neisseria, Pantoea, Pseudomonas, Salmonella, Shigella, Stenotrophomonas, Vibrio*, or *Yersinia*. In certain embodiments, the bacterium is *Citrobacter freundii, Enterobacter aerogenes, Enterobacter cloacae, Escherichia coli, Klebsiella pneumoniae*, or *Klebsiella oxytoca*. In certain embodiments, the bacterium is *Escherichia coli*. In certain embodiments, the bacterium is *Klebsiella pneumoniae*. In certain embodiments, the bacterium is *Burkholderia mallei, Burkholderia pseudomallei, Francisella tularensis*, or *Yersinia pestis*. In certain embodiments, the bacterium has been genetically engineered.

In certain embodiments, the bacterial infection is a urinary tract infection (UTI), upper respiratory infection, lower respiratory tract infection, primary or catheter-associated blood infection, secondary blood infection with a UTI source, neonatal sepsis, intra-abdominal infection, otitis media, or a wound infection. In certain embodiments, the bacterial infection is a recurrent UTI, complicated UTI, uncomplicated UTI, bacteremic UTI, acute pyelonephritis, hospital-acquired pneumonia, community acquired pneumonia, ventilator-acquired pneumonia, complicated intra-abdominal infection (cIAI), or bronchitis. In certain embodiments, the bacterial infection is a UTI. In certain embodiments, the bacterial infection is complicated UTI (cUTI). In certain embodiments, the cUTI is associated with one or more complicating factors selected from the group including: urinary retention, urinary catheterization, structural or anatomical abnormality of the urinary tract, and neurological deficiencies resulting in residual urine of at least 100 mL. In certain embodiments, the bacterial infection is acute pyelonephritis.

In certain embodiments, the bacterium expresses an extended-spectrum-β-lactamase (ESBL). Sequences and classifications of ESBLs are known by of one of skill in the art. For example: Babic et al. Drug Resistance Updates, 2006, 9:142-156; Bush et al. Antimicrob Agents Chemother, 2010; 54(3):969-976). See also The Lactamase Engineering database (www.laced.uni-stuttgart.de/; www.lahey.org/Studies/).

In certain embodiments, the ESBL is inhibited by component (b). In certain embodiments, the ESBL is an Ambler Class A ESBL. In certain embodiments, the ESBL is or is believed to be a CTX-M, TEM, or SHV beta-lactamase. In certain embodiments, the TEM beta-lactamase comprises one or more amino acid substitutions selected from R164S/H/C, G238D/N/S, and E104K. In certain embodiments, the SHV beta-lactamase comprises one or more amino acid substitutions selected from D179A/N/G, G238S/A, and E240K. In certain embodiments, the ESBL is CTX-M group 1, 2, 8, 9, or 25. In certain embodiments, the ESBL is or is believed to be a CTX-M, CTX-M-1, CTX-M-2, CTX-M-3, CTX-M-4, CTX-M-4L or CTX-M-89, CTX-M-5, CTX-M-6, CTX-M-7, CTX-M-8, CTX-M-9, CTX-M-10, CTX-M-12, CTX-M-13, CTX-M-14, CTX-M-15, CTX-M-16, CTX-M-17, CTX-M-19, CTX-M-20, CTX-M-21, CTX-M-22, CTX-M-23, CTX-M-24, CTX-M-25, CTX-M-26, CTX-M-27, CTX-M-28, CTX-M-55, FEC-1, KLUA-1, KLUA-5, KLUA-6, KLUA-8, KLUA-9, KLUA-10, KLUA-11, KLUG-1, SHV-2, SHV-7, SHV-12, TEM-1, or TOHO-1. In certain embodiments, the ESBL is or is believed to be a CTX-M-1, CTX-M-3, CTX-M-14, CTX-M-15, CTX-M-55, SHV-2, SHV-7, SHV-12, or TEM-1. In certain embodiments, the ESBL is or is believed to be CTX-M-14 or CTX-M-15. In certain embodiments, the ESBL is CTX-M-14. In certain embodiments, the ESBL is CTX-M-15.

In certain embodiments, the bacterium further expresses one or more additional beta-lactamase. In certain embodiments, the bacterium further expresses TEM wild-type or SHV wild-type.

In certain embodiments, the bacterium further expresses one or more additional ESBL. In certain embodiments, the one or more additional ESBL is or is believed to be independently CTX-M, a TEM, or a SHV beta-lactamase. In certain embodiments, the one or more additional ESBL is or is believed to be CTX-M, CTX-M-1, CTX-M-2, CTX-M-3, CTX-M-4, CTX-M-4L or CTX-M-89, CTX-M-5, CTX-M-6, CTX-M-7, CTX-M-8, CTX-M-9, CTX-M-10, CTX-M-12, CTX-M-13, CTX-M-14, CTX-M-15, CTX-M-16, CTX-M-17, CTX-M-19, CTX-M-20, CTX-M-21, CTX-M-22, CTX-M-23, CTX-M-24, CTX-M-25, CTX-M-26, CTX-M-27, CTX-M-28, FEC-1, KLUA-1, KLUA-5, KLUA-6, KLUA-8, KLUA-9, KLUA-10, KLUA-11, KLUG-1, SHV-2, SHV-7, SHV-12, TEM-1, or TOHO-1. In certain embodiments, the one or more additional ESBL is or is believed to be CTX-M-1, CTX-M-3, CTX-M-14, CTX-M-15, SHV-2, SHV-7, SHV-12, or TEM-1.

Methods of determining the expression of an ESBL or beta-lactamase are well known in the art. In some embodiments, methods for detecting an ESBL include phenotyping using growth of a bacteria in media supplemented with different types of beta-lactam antibiotics, such as antibiotics. In certain embodiments, the expression of an ESBL can be determined by conventional PCR, real-time PCR, genomic sequencing, such as Next Generation Sequencing, Luminex xMAP technology, DNA hybridization based methods, such as DNA microarrays, e.g. CHECK-MDR CT101, CT102, CT103, or CT103XL (Check-Points, Netherlands). ESBL expression can also be determined by detecting the protein using antibody assays or mass spectrometry. In some cases, an enzyme is identified to be CTX-M-like, such as CTX-M-14-like or CTX-M-15-like, if it is identified by an assay, such as certain gene-based assays, designed to identify a particular gene but that may not distinguish from other genes of high sequence identity in a region or regions being detected. Methods for detecting ESBL-producing bacteria include those described in U.S. Patent Appl. No. US2013/0065790; Frickmann et al. (2014) Biomed Research International, Article ID 375681; and Souverein et al. (2017) Journal of Antimicrobial Chemotherapy, doi: 10.1093/jac/dkx189.

In certain embodiments, the bacterium has an antibiotic resistant phenotype. Methods of determining an antibiotic resistant phenotype are well known in the art. In certain embodiments, the antibiotic resistant phenotype can be determined by assaying the minimum inhibitory concentration or the minimum bactericidal concentration (MBC). In certain embodiments, the antibiotic resistant phenotype is resistance to a DHFR inhibitor, a sulfonamide, an anaerobic DNA inhibitor, a fluoroquinolone, a beta-lactam, or a beta-lactam:beta-lactamase inhibitor combination. In certain embodiments, the antibiotic resistant phenotype is resistance to a fluoroquinolone, a beta-lactam, or a beta-lactam:beta-lactamase inhibitor combination. In certain embodiments, the antibiotic resistant phenotype is resistance to amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, ciprofloxacin, delafloxacin, doripenem, finafloxacin. gentamicin, imipenem, levofloxacin, loracarbef, mecillinam, meropenem, nitrofurantoin, piperacillin, sulfamethoxazole, trimethoprim, or tobramycin. In certain embodiments, the antibiotic resistant phenotype is ST131.

In certain embodiments, the bacterium expresses a qnr gene. In certain embodiments, the qnr gene is member of the qnrA, qnrB, qnrC, qnrD, qnrS, or qnrVC family.

In certain embodiments, the bacterium does not express a carbapenemase. In certain embodiments, the bacterium does not express an Ambler Class C ESBL. In certain embodiments, the bacterium does not express a protein selected from the group consisting of an AmpC, a KPC, an OXA, an NDM, or an OMP. In certain embodiments, the bacterium does not express an AmpC. In certain embodiments, the bacterium does not express a transferable AmpC. In certain embodiments, the bacterium does not express a KPC. In certain embodiments, the bacterium does not express an OXA. In certain embodiments, the bacterium does not express OXA-48 or OXA-181. In certain embodiments, the bacterium does not express an NDM. In certain embodiments, the bacterium does not express NDM-1. In certain embodiments, the bacterium does not express an OMP. In certain embodiments, the bacterium does not express a carbapenemase or a transferable AmpC. In certain embodiments, the bacterium does not express KPC, NDM-1, ACC, ACT/MIR, CMYI/MOX, CMYII, DHA, or FOX.

In some embodiments, component (a) and component (b) is administered with at least one additional antibiotic. In some embodiments, the additional antibiotic is administered by mucosal, oral or parenteral administration. In some embodiments, the additional antibiotic is administered intravenously. In some embodiments, the additional antibiotic is administered orally. In some embodiments, the additional antibiotic is a beta-lactam, such as a penicillin derivative, cephalosporin, monobactam, or carbapenem. In some embodiments, the additional antibiotic is amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, doripenem, gentamicin, imipenem, loracarbef, meropenem, piperacillin, ticarcillin, or tobramycin. In some embodiments, the additional antibiotic is formulated together with component (a). In some embodiments, the additional antibiotic is formulated together with component (b).

In some embodiments, the $IC_{50}$ of component (a) is or is greater than about 50 μM for the ESBL, such as greater than about 100 μM, 200 μM, 300 μM, 400 μM, 500 μM, 600 μM, 700 μM, 800 μM, 900 μM, or 1000 μM for the ESBL. In certain embodiments, the $IC_{50}$ of component (a) is or is greater than about 100 μM or 1000 μM. In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the $K_M$ of component (a) is or is greater than about 30 μM for the ESBL, such as is or is greater than about 30 μM, 40 μM, 50 μM, 60 μM, 70 μM, 80 μM, 90 μM, 100 μM, or more for the ESBL. In certain embodiments, the Km of component (a) is or is greater than about 100 μM for the ESBL. In some aspects, $K_M$ is the substrate concentration at which the reaction rate is half of the maximum rate achieved by the system at saturating substrate concentration. Methods of determining $K_M$ in vitro and in vivo are known in the art.

In certain embodiments, administration of components (a) and (b) in accord with the provided method results in systemic exposure of component (a) of greater than 30%, such as greater than about 35%, 40%, 45%, 50%, 60% or more. In certain embodiments, administration of components (a) and (b) in accord with the provided method results in systemic exposure of component (a) of greater than 40% fT>MIC, greater than 50% fT>MIC, or greater than 60% fT>MIC of component (a).

In certain embodiments, administration of components (a) and (b) in accord with the provided method results in systemic exposure of component (b) of greater than 20% $fT>C_T$, such as great than about 25% 30%, 35%, 40%, 45%, 50%, or more. In certain embodiments, administration of components (a) and (b) in accord with the provided method results in systemic exposure of component (b) of greater than 20% $fT>C_T$, greater than 25% $fT>C_T$, greater than 30% $fT>C_T$, or greater than 40% $fT>C_T$.

In certain embodiments, the peak concentration of component (a) is between about 10 μg/mL and about 30 μg/mL, such as between 10 μg/mL and 25 μg/mL, between 15 μg/mL and about 30 μg/mL, or between 15 μg/mL and about 25 μg/mL. In certain embodiments, the peak concentration of component (b) is between about 0.2 μg/mL and about 5 μg/mL, such as between 0.2 μg/mL and 4 μg/mL, between 0.2 μg/mL and about 3 μg/mL, between 0.5 μg/mL and about 4 μg/mL, between 1 μg/mL and about 4 μg/mL, between 1 μg/mL and about 3 μg/mL. In some embodiments, the peak concentrations are peak serum concentrations.

In certain embodiments, the PBLIE of component (b) in combination with component (a) is or is greater than about 0.5 hours, such as is or is greater than about 0.75 hours, 1 hour, 1.1 hours, 1.2 hours, 1.3 hours, 1.4 hours, 1.5 hours, 1.6 hours, 1.7 hours, 1.8 hours, 1.9 hours, 2 hours, 2.25 hours, 2.5 hours, 2.75 hours, 3 hours, or 3.5 hours. In certain embodiments, the PBLIE of component (b) in combination with component (a) is or is greater than about 1 hour, greater than about 1.5 hours, greater than about 2 hours, or greater than about 2.5 hours. Methods of determining PBLIE in vitro are known in the art. In some aspects, in order to calculate the PBLIE, two experimental conditions are compared, such as a first condition in which the bacteria are exposed to a β-lactam alone, and in the second to the combination of the same β-lactam in combination with a β-lactamase inhibitor. In an assay, after a certain period of time, such as after one hour, the cells are washed and re-suspended in media with the β-lactam alone and the growth of the bacterial culture is then monitored over time. In some embodiments, the difference between the time it takes for the two cultures to grow 1-log of colony forming units per mL after washout (J Antimicrob Chemother 2004; 53:616-619) is the metric used to define the PBLIE.

In certain embodiments, the MIC of component (a) when used in combination with component (b) is or is less than about 8 μg/mL, such as is or is less than about 4 μg/mL, 2 μg/mL, 1 μg/mL, 0.5 μg/mL, or 0.25 μg/mL. In certain embodiments, the MIC of component (a) when used in combination with component (b) is or is less than about 4 μg/mL, is or is less than about 2 μg/mL, is or is less than about 1 μg/mL, or is or is less than about 0.5 μg/mL. In certain embodiments, the MIC of component (a) alone, such as for the same microorganism, e.g. bacterial strain, e.g. ESBL-producing Enterobacteriaceae, is or is greater than about 4 μg/mL, such as is or is greater than about 8 μg/mL, 16 μg/mL, or 32 μg/mL. In certain embodiments, the MIC of component (a) alone is or is greater than about 2-fold more than the MIC of component (a) when used in combination with component (b) for the same microorganism, e.g. bacterial strain, e.g. ESBL-producing Enterobacteriaceae, such as is or is greater than about 3-fold, 4-fold, 5-fold, 6-fold, 7-fold, 8-fold, 9-fold, 10-fold, 16-fold, 32-fold, 64-fold or more. Methods of determining MIC in vitro are known in the art.

In certain embodiments, the minimum bactericidal concentration (MBC) of component (a) when used in combination with (b) is or is less than 4-fold or 2-fold higher than the MIC of component (a) when used in combination with component (b). In certain embodiments, the MBC of component (a) when used in combination with (b) is or is greater than the MIC of component (a) when used in combination with component (b).

In still another embodiment of the present invention there is provided a method for treating a mammal with a bacterial infection, the method comprising: a) obtaining a sample from a mammal suffering from a bacterial infection; b) identifying the presence of bacteria in said sample; c) determining the MIC required to kill the bacteria identified in step b); and d) administering the combination composition to a subject based on the MIC value determined in step c).

V. KITS AND ARTICLES OF MANUFACTURE

Provided herein are articles of manufacture or kits comprising (a) ceftibuten or a pharmaceutically acceptable salt thereof, or a hydrate of the foregoing and (b) clavulanic acid, or a pharmaceutically acceptable salt thereof, or a hydrate of the foregoing. In some embodiments, the kits further include (c) instructions for use, e.g. for administering an effective amount of components (a) and (b) for treatment of a bacterial infection to an individual in need thereof according to a method as described herein. In some embodiments, the bacterial infection is associated with a bacterium that expresses an extended-spectrum-β-lactamase (ESBL).

In certain embodiments, kits include one or more containers containing components (a) and/or (b). In certain embodiments, the kit comprises a container comprising component (a), wherein component (a) is ceftibuten or a pharmaceutically acceptable salt there, or a hydrate of the foregoing. In certain embodiments, component (a) comprises a hydrate. In certain embodiments, component (a) is ceftibuten dihydrate. In certain embodiments, the kit comprises a container comprising component (b), wherein component (b) is clavulanic acid, or a pharmaceutically acceptable salt thereof. In certain embodiments, component (b) comprises a pharmaceutically acceptable salt. In certain embodiments, the salt is sodium or potassium. In certain embodiments, component (b) is potassium clavulanate. In certain embodiments, the kit comprises one or more containers comprising ceftibuten dihydrate (component (a)) and potassium clavulanate (component (b)), in which component (a) and component (b) are provided in the same container (e.g. formulated together) or separate containers. In certain embodiments, the kit comprises a container comprising both component (a) and component (b). In certain embodiments, the kit comprises a first container comprising component (a) and a second container comprising component (b).

In some embodiments, the kit and/or components of the kits are packaged, such as in packaging containing paper (e.g. cardboard), plastic or other suitable material. In some embodiments, the components of the kit are contained in one or more containers. In some embodiments, the kit further comprises instructions for use in accordance with any of the methods described herein. Instructions supplied in the kits are typically written instructions on a label or package insert (e.g., a paper sheet included in the kit), but machine-readable instructions (e.g., instructions carried on a magnetic or optical storage disk) are also acceptable.

In some embodiments, the component (a) and component (b) in the kits provided herein are contained as a pharmaceutical composition as described herein. In some embodiments, component (a) and component (b) are provided as separate compositions. In some embodiments, component (a) and component (b) are provided together in the same composition.

In some embodiments, the kit contains component (a) and component (b) in combination in a single dosage form and/or as separate doses in a plurality of single dosage forms. In some embodiments, the single dosage form is an oral dosage form. In some embodiments, the single dosage form is for administration of a unit dose, such as is a unit dose form, e.g. in the form of a tablet or capsule. In some embodiment, a unit dose is a discrete amount of the pharmaceutical composition comprising a predetermined amount of active ingredient. Amounts of active ingredients are generally equal to the dosage of active ingredients which would be administered to individuals and/or convenient fractions of such a dosage such as, for example, one half- or one-third of such a dosage. The dose of each drug (e.g. mg) and the form of the dose (e.g. tablet, capsule) can be any doses or forms as described above.

In some embodiments, the kit contains at least two dosage forms, such as two or more fractions of doses in unit dose form, of component (a). In some aspects, the two or more dosage forms together are sufficient to provide at least one total daily dose of component (a), such as a total daily dose as described above, e.g. a total daily dose of about 500 mg-2000 mg, such as about 800 mg to 1800 mg, e.g. 900 mg to 1200 mg. In some embodiments, the kit contains dosage forms, e.g. unit dose forms, of component (a) for administration of the total daily dose as divided doses of component (a) 2 to 5 times a day, such as two or three times a day. In some embodiments, the dosage form, e.g. unit dosage form, comprises about 150-600 mg of component (a), such as between about 150-400, 200-400, or 300-400 mg, e.g. about 300 mg or about 400 mg. In some embodiments, the kit contains dosage forms, e.g. unit dose forms, of component (a) for administration of 2 or more unit dose forms per each divided dose, such as 1, 2, 3, or 4 unit dose forms for each divided dose. In some embodiments, the dosage form, e.g. unit dosage form, comprises between about 50 and 250 mg, such as 100 mg and 200 mg, e.g. about 100 mg or about 200 mg. In some embodiments, the kit contains sufficient dosage forms, e.g. unit dose forms, of component (a) for administration of the total daily dose for greater than 3 days, such as for up to or for about 3, 4, 5, 6, 7, 8, 9, 10, 11, 12, 13, 14, 15, 16, 17, 18, 19 or 20 days, such as 7 to 10 days.

In some embodiments, the kit contains at least two dosage forms, such as two or more fractions of doses in unit dosage form, of component (b). In some aspects, the two or more dosage forms together are sufficient to provide at least one total daily dose of component (b), such as a total daily dose as described above, e.g. a total daily dose of about 250 mg-750 mg, such as about 375 to 562.5 mg. In some embodiments, the kit contains dosage forms, e.g. unit dose forms, of component (b) for administration of the total daily dose as divided doses of component (b) 2 to 5 times a day, such as two or three times a day. In some embodiments, the dosage form, e.g. unit dose dosage form, comprises about 50-250 mg of component (b), such as between about 50-250 mg, 100-200 mg, or 125-187.5 mg of component (b), e.g. about 125 mg or about 187.5 mg. In some embodiments, the kit contains dosage forms, e.g. unit dose forms, of component (b) for administration of 2 or more unit dose forms per each divided dose, such as 1, 2, 3, or 4 unit dose forms for each divided dose. In some embodiments, the dosage form, e.g. unit dosage form, comprises between about 50 and 150 mg, such as 62.5 mg and 125 mg, e.g. about 62.5 mg or about 125 mg. In some embodiments, the kit contains sufficient unit dose forms of component (b) for administration of the total daily dose for greater than 3 days, such as for up to or for about 3, 4, 5, 6, 7, 8, 9, 10, 11, 12, 13, 14, 15, 16, 17, 18, 19 or 20 days, such as 7 to 10 days.

In some embodiments, the container can be a divided container, such as a divided bottle or a divided foil pack. In some embodiments, components (a) and component (b) are separated from each other in the divided container and/or each dosage form, e.g. unit dose form, is separated from each other in the divided container. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved. It is feasible that more than one container can be used together in a single package to market a single dosage form. For example, tablets may be contained in a bottle that is in turn contained within a box.

In some embodiments, the kit includes a blister pack. Blister packs are well known in the packaging industry and are used for the packaging of pharmaceutical unit dosage forms (tablets, capsules, and the like). Blister packs generally contain a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. In some aspects, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. In some aspects, the strength of the sheet is such that the tablets or capsules can be removed from the blister pack by manually applying pressure on the recesses whereby an opening is formed in the sheet at the place of the recess. The tablet or capsule can then be removed via said opening.

In some embodiments, the kit includes doses suitable for multiple days of administration, such as up to or for about one week, one month or three months. In some embodiments, the kit contains doses suitable for greater than 3 days, such as for up to or for about 3, 4, 5, 6, 7, 8, 9, 10, 11, 12, 13, 14, 15, 16, 17, 18, 19 or 20 days, such as 7 to 10 days. In some embodiments, the kit is a multi-day pack containing a number of divided daily doses. In some aspects, in multi-day packs the doses (e.g. tablets) for each administration (e.g. BID or TID administration) are separated from doses to be administered on different days or at different times.

In certain embodiments, the kits are in suitable packaging. Suitable packaging include, but is not limited to, vials, bottles, jars, flexible packaging (e.g., sealed Mylar or plastic bags), and the like.

In some embodiments, the kit includes instructions for administering the components or the composition(s) in accord with any of the provided methods. In some embodiments, the instructions specify one or more of the bacterial infection to be treated, including the type of bacterial strain and/or ESBL produced by the bacterial strain; the patient population to be treated; the dosing regimen of the components to the individual, such as the total daily dose of each component or of the composition, the number of divided doses of each component or of the composition, the number of tablets or capsules per divided dose and/or the number of days of a treatment.

In some embodiments, the instructions specify the components or the composition(s) of the kit are for treating a bacterial infection caused by or associated with an Enterobacteriaceae strain, such as an Enterobacteriaceae species selected from the group consisting of isolates of *Citrobacter freundii, Enterobacter aerogenes, Enterobacter cloacae, Escherichia coli, Klebsiella pneumoniae* and *Klebsiella oxytoca*. In some embodiments, the instructions specify the components of the kit are for treating a bacterial infection as described herein, such as complicated urinary tract infection, uncomplicated urinary tract infection and acute pyelonephritis.

In some embodiments, the kit specifies the components are for treating bacterial infections caused by, associated with or involving Enterobacteriaceae that express or produce an extended-spectrum-β-lactamase (ESBL) or a particular type of ESBL, such as a SHV, TEM or CTX-M, including any as described in accord with the provided methods. In some embodiments, the ESBL is or includes CTX-M-14 or CTX-M-15. In some embodiments, the instructions specify the individual to be treated is one that has been selected or determined to have a bacterial infection that expresses or produced the ESBL, such as determined by PCR, real-time PCR, genomic sequencing, such as Next Generation Sequencing, or microarray-based assay.

In some embodiments, the instructions specify the total daily dose of components (a) and components (b) to be administered which, in some aspects, can be specified for administration in a single dose or in divided (multiple) doses.

In some embodiments, the kit includes instructions for administering to the individual (e.g. orally administered) a total daily dose of component (a) of about 500 mg-2000 mg, such as about 600 to 1800 mg, 600 to 1600 mg, 600 to 1400 mg, 600 to 1200 mg, 600 to 1000 mg, 600 to 900 mg, 600 to 800 mg, 800 mg to 2000 mg, 800 mg to 1800 mg, 800 mg to 1600 mg, 800 mg to 1400 mg, 800 to 1200 mg, 800 to 1000 mg, 800 to 900 mg, 900 to 2000 mg, 900 to 1800 mg, 900 to 1600 mg, 900 to 1400 mg, 900 to 1200 mg, 900 to 1000 mg, 1000 to 2000 mg, 1000 to 1800 mg, 1000 to 1600 mg, 1000 to 1400 mg, 1000 to 1200 mg, 1200 mg to 2000 mg, 1200 mg to 1800 mg, 1200 mg to 1600 mg, 1200 mg to 1400 mg, 1400 mg to 2000 mg, 1400 mg to 1800 mg, 1400 mg to 1600 mg, 1600 mg to 2000 mg, 1600 mg to 1800 mg, or 1800 mg to 2000 mg, each inclusive. In some embodiments, the kit includes instructions for administering to the individual (e.g. orally administered) a total daily dose of component (b) of about 250 mg-750 mg, such as about 250 to 600 mg, 250 to 600 mg, 250 to 500 mg, 250 to 375 mg, 250 to 300 mg, 300 to 750 mg, 300 to 600 mg, 300 to 750 mg, 300 to 600 mg, 300 to 500 mg, 300 to 375 mg, 375 to 750 mg, 375 to 600 mg, 375 to 500 mg, 500 to 750 mg, 500 to 600 mg, or 600 to 750 mg, each inclusive. In some embodiments, the kit includes instructions for administering to an individual (e.g. orally administering) component (a) in a total daily dose of 800-1800 mg, such as 900-1200 mg, and component (b) in a total daily dose of 250-750 mg, such as 375-562.5 mg.

In some embodiments, the instructions specify the number of divided doses, e.g. as one or more unit dosage form (e.g. tablet or capsule), to be administered to provide a total daily dose of one or both of component (a) and component (b). In some embodiments, the kit includes instructions for administering unit dose forms (e.g. capsules) of component (a) and/or (b) 2-5 times per day, such as two or three times per day. In some embodiments, components (a) and (b) are formulated separately and the instructions specify that components (a) and (b) are to be administered simultaneously or concurrently at the same time.

In some embodiments, the kits includes instructions to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen that the tablets or capsules so specified should be ingested or a card that contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

In some embodiments, the kit includes a dispenser to dispense the divided daily doses or one at a time in the order of their intended use. In some cases, the dispenser is equipped with a memory-aid, so as to further facilitate compliance with the regimen. An example of such a memory-aid is a mechanical counter, which indicates the number of divided daily doses that has been dispensed. Another example of such a memory-aid is a battery-powered micro-chip memory coupled with a liquid crystal readout, or audible reminder signal that, for example, reads out the time that the last daily dose had been taken and/or the date that the last daily dose has been taken and/or reminds one when the next dose is to be taken.

In some embodiments, the kit includes at least one additional antibiotic. In some embodiments, the additional antibiotic is a beta-lactam, such as a penicillin derivative, cephalosporin, monobactam, or carbapenem. In some embodiments, the additional antibiotic is amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, ceicarcillin, cephalexin, cephradine, doripenem, gentamicin, imipenem, loracarbef, meropenem, piperacillin, ticarcillin or tobramycin. In some embodiments, the additional antibiotic is formulated together with component (a). In some embodiments, the additional antibiotic is formulated together with component (b). In some embodiments, the additional antibiotic is suitable for intravenous administration. In some embodiments, the additional antibiotic is suitable for oral administration. In some embodiments, the kit includes instructions for administering the additional antibiotic in combination, separately (e.g. simultaneously, concurrently or sequentially) or together, with component (a) and/or component (b) by mucosal, oral or parenteral administration.

VI. EXEMPLARY EMBODIMENTS

Among the provided embodiments are:

1. A method of treating an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein:
   the bacterial infection is caused by a Enterobacteriaceae that expresses an extended-spectrum beta-lactamase (ESBL); and
   the method is characterized by one or more of (i)-(iii):
   (i) component (a) is administered to the individual at a total daily dose of 800-1800 mg;
   (ii) component (b) is administered to the individual at a total daily dose of 250-750 mg;
   (iii) a total daily dose is administered in two or more divided doses per day of one or both of components (a) and (b).

2. A method of prophylaxis of an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein:
   the bacterial infection is caused by a Enterobacteriaceae that expresses an extended-spectrum beta-lactamase (ESBL); and
   the method is characterized by one or more of (i)-(iii):
   (i) component (a) is administered to the individual at a total daily dose of 800-1800 mg;
   (ii) component (b) is administered to the individual at a total daily dose of 250-750 mg;
   (iii) a total daily dose is administered in two or more divided doses of one or both of components (a) and (b).

3. The method of embodiment 1 or embodiment 2, wherein component (a) and component (b) are administered together in the same pharmaceutical composition.

4. A method of treating or prophylaxis of an Enterobacteriaceae bacterial infection in an individual, the method comprising orally administering to the individual (a) ceftibuten or a pharmaceutically acceptable salt thereof, or a hydrate of the foregoing, wherein:
   the bacterial infection is caused by an Enterobacteriaceae that expresses an extended-spectrum beta-lactamase (ESBL);
   component (a) is administered in a total daily dose of 800-1800 mg and/or is administered in two or more divided doses per day, wherein the divided doses of component (a) is about 300-400 mg of component (a); and
   component (a) is administered with (b) clavulanic acid, or a pharmaceutically acceptable salt thereof, wherein component (b) is orally administered in a total daily dose of about 250-750 mg and/or is administered in two or more divided doses per day, wherein the divided dose of component (b) is about 100-250 mg.

5. A method of treating or prophylaxis of an Enterobacteriaceae bacterial infection in an individual, the method comprising orally administering to the individual a daily dose of (b) clavulanic acid, or a pharmaceutically acceptable salt thereof, wherein:
   the bacterial infection is caused by an Enterobacteriaceae that expresses an extended-spectrum beta-lactamase (ESBL);
   component (b) is administered in a total daily dose of 250-750 mg and/or is administered in two or more divided doses per day, wherein the divided dose of component (b) is about 100-250 mg; and
   component (b) is administered with (a) ceftibuten or a pharmaceutically acceptable salt thereof, or a hydrate of the foregoing, wherein component (a) is orally administered in a total daily dose of about 800-1800 mg and/or is administered in two or more divided doses, wherein the divided dose of component (a) is about 300-400 mg.

6. The method of any of embodiments 1-5, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP).

7. A method of treating an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein:
   the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP); and/or
   the bacterial infection is caused by or associated with an Enterobacteriaceae that expresses an extended spectrum β-lactamase (ESBL).

8. A method of prophylaxis of an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP); and/or the bacterial infection is caused by or associated with an Enterobacteriaceae that expresses an extended spectrum β-lactamase (ESBL).

9. A method of treating a bacterial infection in an individual, wherein the method comprises orally administering to the individual (a) ceftibuten or a pharmaceutically acceptable salt thereof, or a hydrate of the foregoing; and (b) clavulanic acid, or a pharmaceutically acceptable salt thereof, wherein the bacterial infection is caused by a bacterium that expresses an extended-spectrum-β-lactamase (ESBL), and wherein the individual was previously administered an antibiotic to treat the bacterial infection.

10. The method of any of embodiments 1-9, wherein component (a) is ceftibuten dihydrate.

11. The method of any of embodiments 1-10, wherein component (b) is potassium clavulanate.

12. The method of any of embodiments 1-2 and 4-11, wherein component (a) is administered simultaneously or sequentially with component (b).

13. The method of any of embodiments 7-12, wherein components (a) and (b) are administered together in the same pharmaceutical composition.

14. The method of any of embodiments 1-13, wherein component (a) is administered to the individual at a ratio to component (b) of between 1:1-7:1.

15. The method of any of embodiments 1-14, wherein component (a) is administered to the individual at a ratio to component (b) of between 1:1-3:1.

16. The method of embodiments 7-15, wherein the method is characterized by one or more of (i)-(iii):
(i) component (a) is administered to the individual at a total daily dose of 800-1800 mg;
(ii) component (b) is administered to the individual at a total daily dose of 250-750 mg;
(iii) a total daily dose is administered in two or more divided doses of one or both of components (a) and (b).

17. The method of any of embodiments 1-3, 6 and 10-16, wherein the method is characterized by (i) and the total daily dose is administered in two or more divided doses per day.

18. The method of any of embodiments 1-3, 6 and 10-17, wherein the method is characterized by (ii) and the total daily dose is administered in two or more divided doses per day.

19. The method of any of embodiments 1-3, 6 and 10-18, wherein the method is characterized by (i), (ii), and (iii).

20. The method of any of embodiments 1-6 and 10-19, wherein the total daily dose of one or both of components (a) and (b) is administered in 2-5 divided doses per day.

21. The method of any of embodiments 1-6 and 10-20, wherein the total daily dose of one or both of components (a) and (b) is administered in 2 or 3 divided doses per day.

22. The method of any of embodiments 1-6 and 10-21, wherein the divided dose of component (a) is administered in an amount of about 300-600 mg of component (a).

23. The method of any of embodiments 1-6 and 10-22, wherein the divided dose of component (a) is about 300-400 mg of component (a).

24. The method of any of embodiments 1-23, wherein component (a) is administered in a total daily dose of 900-1200 mg.

25. The method of any of embodiments 1-6 and 10-24, wherein the divided dose of component (b) is about 100-250 mg.

26. The method of any of embodiments 1-25, wherein component (b) is administered in a total daily dose of 375-562.5 mg.

27. A method of treating or prophylaxis of an Enterobacteriaceae bacterial infection in an individual, the method comprising orally administering to the individual (a) ceftibuten or a pharmaceutically acceptable salt thereof, or a hydrate of the foregoing; and (b) clavulanic acid, or a pharmaceutically acceptable salt thereof, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or wherein the Enterobacteriaceae expresses an extended-spectrum beta lactamase (ESBL); and
(i) the component (a) and component (b) are administered in two or three divided doses per day, wherein the divided dose of component (a) is about 300-400 mg and the divided dose of component (b) is about 100-250 mg; and/or
(ii) component (a) is administered in a total daily dose of 900-1200 mg and component (b) is administered in a total daily dose of 375-562.5 mg.

28. The method of any of embodiments 1-6 and 10-27, wherein the divided dose of component (b) is about 125-187.5 mg.

29. The method of any of embodiments 1-6 and 10-28, wherein the divided dose of component (a) is about 400 mg.

30. The method of any of embodiments 1-6 and 10-29, wherein the divided dose of component (a) is about 300 mg of component (a).

31. The method of any of embodiments 1-6 and 10-30, wherein the divided dose of component (b) is about 125 mg.

32. The method of any of embodiments 1-6 and 10-31, wherein the divided dose of component (b) is about 187.5 mg of component (b).

33. The method of any of embodiments 1-32, wherein one or both of components (a) and (b) are formulated as a capsule, solutab, sachet, suspension, or tablet.

34. The method of any of embodiments 1-33, wherein one or both of components (a) and (b) are formulated as a capsule, and wherein the capsule is size 0, 1, or 2.

35. The method of any of embodiments 1-34, wherein one or both of components (a) and (b) are formulated for modified or extended release.

36. The method of any of embodiments 1-35, wherein the Enterobacteriaceae bacterium is a *Citrobacter freundii*, *Enterobacter aerogenes*, *Enterobacter cloacae*, *Escherichia coli*, *Klebsiella pneumoniae*, or *Klebsiella oxytoca*.

37. The method of any of embodiments 1-36, wherein the bacterial infection is a complicated UTI or acute pyelonephritis.

38. The method of any of embodiments 1-37, wherein method is characterized by one or more of the following:
(i) the ESBL is inhibited by component (b);
(ii) the $IC_{50}$ of component (a) is greater than about 100 µM or 1000 µM for the ESBL;

(iii) the $K_M$ of component (a) is greater than about 100 μM for the ESBL;

(iv) the administration of component (a) and component (b) results in systemic exposure of component (a) of greater than 40% fT>MIC, greater than 50% fT>MIC, or greater than 60% fT>MIC of component (a);

(v) the administration of components (a) and (b) results in systemic exposure of component (b) of greater than 20% fT>CT, greater than 25% fT>CT, greater than 30% fT>CT, or greater than 40% fT>CT;

(vi) the PBLIE of component (b) in combination with component (a) is or is greater than about 1 hour, greater than about 1.5 hours, greater than about 2 hours, or greater than about 2.5 hours;

(vii) the MIC of component (a) when used in combination with component (b) is or is less than about 4 μg/mL, is or is less than about 2 μg/mL, is or is less than about 1 μg/mL, or is or is less than about 0.5 μg/mL;

(viii) the MIC of component (a) alone is or is greater than about 4-fold more than the MIC of component (a) for the same Enterobacteriaceae, optionally ESBL-producing Enterobacteriaceae, when used in combination with component (b);

(ix) the MBC of component (a) when used in combination with component (b) is or is less than 4-fold or 2-fold higher than the MIC of component (a) when component (a) is used in combination with component (b) for the same Enterobacteriaceae, optionally ESBL-producing Enterobacteriaceae;

(x) the administration of component (a) and component (b) results in a peak concentration of component (a) between about 10 μg/mL and about 30 μg/mL, between 10 μg/mL and 25 μg/mL, between 15 μg/mL and about 30 μg/mL, or between 15 μg/mL and about 25 μg/mL, optionally wherein the peak concentration is peak serum concentration; and/or (xi) the peak concentration of component (b) is between about 0.2 μg/mL and about 5 μg/mL, between 0.2 μg/mL and 4 μg/mL, between 0.2 μg/mL and about 3 μg/mL, between 0.5 μg/mL and about 4 μg/mL, between 1 μg/mL and about 4 μg/mL, between 1 μg/mL and about 3 μg/mL, optionally wherein the peak concentrations is peak serum concentration.

39. The method of any of embodiments 1-38, wherein the ESBL is a CTX-M, TEM, or SHV beta-lactamase.

40. The method of any of embodiments 1-39, wherein the ESBL is CTX-M-14 or CTX-M-15 or is of the same CTX-M group as CTX-M-14 or CTX-M-15.

41. The method of any of embodiments 1-40, wherein the bacterium expresses CTX-M-14.

42. The method of any of embodiments 1-41, wherein the bacterium expresses CTX-M-15.

43. The method of any of embodiments 1-42, wherein the bacterium further expresses one or more additional beta-lactamase.

44. The method of embodiment 43, wherein the one or more additional beta-lactamase is independently CTX-M, a FEC, a KLUA, a KLUG, a TEM, a TOHO, or a SHV beta-lactamase.

45. The method of embodiment 43 or 44, wherein the one or more additional beta-lactamase is independently CTX-M, CTX-M-1, CTX-M-2, CTX-M-3, CTX-M-4, CTX-M-4L or CTX-M-89, CTX-M-5, CTX-M-6, CTX-M-7, CTX-M-8, CTX-M-9, CTX-M-10, CTX-M-12, CTX-M-13, CTX-M-14, CTX-M-15, CTX-M-16, CTX-M-17, CTX-M-19, CTX-M-20, CTX-M-21, CTX-M-22, CTX-M-23, CTX-M-24, CTX-M-25, CTX-M-26, CTX-M-27, CTX-M-28, FEC-1, KLUA-1, KLUA-5, KLUA-6, KLUA-8, KLUA-9, KLUA-10, KLUA-11, KLUG-1, SHV-2, SHV-7, SHV-12, TEM-1, TEM-OSBL, or TOHO-1.

46. The method of any of embodiments 43-45, wherein the one or more additional beta-lactamase is independently CTX-M-1, CTX-M-3, CTX-M-14, CTX-M-15, SHV-2, SHV-7, SHV-12, TEM-1, or TEM-OSBL.

47. The method of any of embodiments 1-46, wherein the bacterium has an antibiotic resistant phenotype.

48. The method of embodiment 47, wherein the antibiotic resistant phenotype is resistance to a fluoroquinolone, a beta-lactam, or a beta-lactam:beta-lactamase inhibitor combination.

49. The method of embodiment 47 or 48, wherein the antibiotic resistant phenotype is resistance to amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, ciprofloxacin, doripenem, gentamicin, imipenem, levofloxacin, loracarbef, meropenem, piperacillin, or tobramycin.

50. The method of any of embodiments 47-49, wherein the antibiotic resistant phenotype is ST131.

51. The method of any of embodiments 1-50, wherein the bacterium does not express a protein selected from the group consisting of an AmpC, a KPC, an OXA, an NDM, or an OMP.

52. The method of any of embodiments 1-51, wherein the bacterium does not express an AmpC.

53. The method of any of embodiments 1-52, wherein the bacterium does not express a KPC.

54. The method of any of embodiments 1-50, wherein the bacterium does not express an OXA.

55. The method of any of embodiments 1-54, wherein the bacterium does not express an NDM.

56. The method of any of embodiments 1-55, wherein the bacterium does not express an OMP.

57. The method of any of embodiments 1-8 and 10-56, wherein the individual was previously administered an antibiotic to treat the bacterial infection.

58. The method of embodiment 9 or claim 57, wherein the previously administered antibiotic was a beta-lactam or a fluoroquinolone.

59. The method of any of embodiments 9 and 57-58, wherein the previously administered antibiotic was not fully effective at treating the bacterial infection.

60. The method of any of embodiments 9 and 57-59, wherein the previously administered antibiotic was an intravenously administered antibiotic.

61. The method of any one of embodiments 1-60, wherein administration of components (a) and (b) is a step-down therapy or is the oral portion of an intravenous to oral therapy switch.

62. The method of any of embodiments 1-61, wherein component (a) and component (b) are administered with food.

63. The method of any of embodiments 1-61, wherein component (a) and component (b) are administered without food.

64. The method of any of embodiments 1-63, wherein the individual has a renal impairment.

65. The method of any of embodiments 1-64, wherein component (a) and component (b) are administered on an outpatient basis and/or are self-administered by the individual.

66. The method of any of embodiments 1-65, wherein component (a) and component (b) are administered for at least about or about 3 days, 4 day, 5 days, 6 days, 7 days, 8 day, 9 days, 10 days, 11 days, 12 days, 13 days, 14 days, 15 days, 16 days, 17 days, 18 days, 19 days, or 20 days.

67. The method of any of embodiments 1-66, wherein component (a) and component (b) are administered for about 7 to 10 days.

68. The method of any of embodiments 1-67, wherein the individual is a human.

69. Use of (a) ceftibuten or a pharmaceutically acceptable salt thereof, or a hydrate of the foregoing and (b) clavulanic acid, or a pharmaceutically acceptable salt thereof in the manufacture of a medicament for treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL); and the medicament is to be used to orally administer a divided dose of component (a) and a divided dose of component (b) to an individual, wherein component (a) and component (b) is administered in two or more divided doses per day and the divided doses are characterized by one or more of the following:
  (i) the divided dose of component (a) is for administering a total daily dose of 800-1800 mg;
  (ii) the divided dose of component (a) is at least or about at least 300 mg;
  (iii) the divided dose of component (b) is for administering a total daily dose of 250-750 mg; and/or
  (iv) the divided dose of component (b) is at least or about at least 100 mg.

70. The use of embodiment 69, wherein component (a) and component (b) are combined in a single dosage form.

71. The use of embodiment 69, wherein component (a) and component (b) are provided in separate dosage forms.

72. Use of (a) ceftibuten or a pharmaceutically acceptable salt thereof, or a hydrate of the foregoing in the manufacture of a medicament for treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL);

the medicament is to be used to orally administer a divided dose of component (a) to an individual;

component (a) is administered with (b) clavulanic acid, or a pharmaceutically acceptable salt thereof, wherein component (b) is orally administered in a divided dose; and component (a) component (b) are to be administered in two or more divided doses per day and the divided doses are characterized by one or more of the following:
  (i) the divided dose of component (a) is for administering a total daily dose of 800-1800 mg;
  (ii) the divided dose of component (a) is at least or about at least 300 mg;
  (iii) the divided dose of component (b) is for administering a total daily dose of 250-750 mg; and/or
  (iv) the divided dose of component (b) is at least or about at least 100 mg.

73. Use of (b) clavulanic acid, or a pharmaceutically acceptable salt thereof in the manufacture of a medicament for treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is an Enterobacteriaceae that expresses an extended-spectrum beta-lactamase (ESBL);

the medicament is to be used to orally administer a divided dose of component (b) to an individual;

component (b) is administered with (a) ceftibuten or a pharmaceutically acceptable salt thereof, or a hydrate of the foregoing, wherein component (a) is orally administered in a divided dose; and component (a) and component (b) are to be administered in two or more divided doses per day and the divided doses are characterized by one or more of the following:
  (i) the divided dose of component (a) is for administering a total daily dose of 800-1800 mg;
  (ii) the divided dose of component (a) is at least or about at least 300 mg;
  (iii) the divided dose of component (b) is for administering a total daily dose of 250-750 mg; and/or
  (iv) the divided dose of component (b) is at least or about at least 100 mg.

74. Use of (a) ceftibuten or a pharmaceutically acceptable salt thereof, or a hydrate of the foregoing and (b) clavulanic acid, or a pharmaceutically acceptable salt thereof in the manufacture of a medicament for treating or prophylaxis of an Enterobacteriaceae bacterial infection, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL), and wherein components (a) and (b) are formulated for oral administration.

75. The use of embodiment 74, wherein the medicament is to be used to orally administer a divided dose of component (a) and/or a divided dose of component (b) to an individual, wherein t component (a) and component (b) are to be administered in two or more divided doses per day and the divided doses are characterized by one or more of the following:
  (i) the divided dose of component (a) is for administering a total daily dose of 800-1800 mg;
  (ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

76. The use of embodiment 75, wherein component (a) and component (b) are combined in a single dosage form.

77. The use of embodiment 75, wherein component (a) and component (b) are provided in separate dosage forms.

78. A pharmaceutical composition comprising (a) ceftibuten or a pharmaceutically acceptable salt thereof, or a hydrate of the foregoing and (b) clavulanic acid, or a pharmaceutically acceptable salt thereof, or a hydrate of the foregoing for use in treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL); and the pharmaceutical composition is to be used to orally administer a divided dose of component (a) and component (b) to the individual, wherein component (a) component (b) are to be administered in two or more divided doses per day and the divided doses are characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

79. The pharmaceutical composition of embodiment 78, wherein component (a) and component (b) are combined in a single dosage form.

80. The pharmaceutical composition of embodiment 79, wherein component (a) and component (b) are provided in separate dosage forms.

81. A pharmaceutical composition comprising (a) ceftibuten or a pharmaceutically acceptable salt thereof, or a hydrate of the foregoing for treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL); and the pharmaceutical composition is to be used to orally administer a divided dose of component (a) to an individual, component (a) is administered with (b) clavulanic acid, or a pharmaceutically acceptable salt thereof, wherein component (b) is orally administered in a divided dose; and component (a) and component (b) are to be administered in two or more divided doses per day and the divided doses are characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

82. A pharmaceutical composition comprising (b) clavulanic acid, or a pharmaceutically acceptable salt thereof for use in treating or prophylaxis of an Enterobacteriaceae bacterial infection, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL);

the pharmaceutical composition is to be used to orally administer a divided dose of component (b) to an individual;

component (b) is for administration with (a) ceftibuten or a pharmaceutically acceptable salt thereof, or a hydrate of the foregoing, wherein component (a) is orally administered in a divided dose; and component (a) and component (b) are to be administered in two or more divided doses per day and the divided doses are characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

83. A pharmaceutical composition comprising (a) ceftibuten or a pharmaceutically acceptable salt thereof, or a hydrate of the foregoing and (b) clavulanic acid, or a pharmaceutically acceptable salt thereof for treating or prophylaxis of an Enterobacteriaceae bacterial infection, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL), and wherein the pharmaceutical composition is formulated for oral administration.

84. The pharmaceutical composition of embodiment 83, wherein the composition is to be used to orally administer a divided dose of component (a) and/or a divided dose of component (b) to an individual, wherein component (a) and/or component (b) are to be administered in two or more divided doses per day and the divided doses are characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

85. The pharmaceutical composition of embodiment 83 or embodiment 84, wherein component (a) and component (b) are combined in a single dosage form.

86. The pharmaceutical composition of embodiment 84 or embodiment 85, wherein component (a) and component (b) are provided in separate dosage forms.

87. The use or pharmaceutical composition of any of embodiments 69-86, wherein component (a) is ceftibuten dihydrate.

88. The use or pharmaceutical composition of any of embodiments 69-87, wherein component (b) is potassium clavulanate.

89. The use or pharmaceutical composition of any of embodiments 69, 71-75, 77, 78, 80-84, and 86-88, wherein component (a) and component (b) are for administration simultaneously, concurrently or sequentially.

90. The use or pharmaceutical composition of any of embodiments 69, 70, 72-76, 78, 79, 81-85, and 87-89, wherein component (a) and component (b) are for administration together.

91. The use or pharmaceutical composition of any of embodiments 69, 71-75, 77, 78, 80-84, and 86-89, wherein component (a) and component (b) are for administration separately.

92. The pharmaceutical composition or use of any of embodiments 69-91, wherein component (a) and component (b) are to be used on an outpatient basis and/or are to be self-administered by the individual.

93. The use or pharmaceutical composition of any of embodiments 69-92, wherein component (a) is administered to the individual at a ratio to component (b) of between 1:1-7:1.

94. The use or pharmaceutical composition of any of embodiments 69-93, wherein component (a) is administered to the individual at a ratio to component (b) of between 1:1-3:1.

95. The use or pharmaceutical composition of any of embodiments 69-94, wherein the divided dose is administered 2-5 times per day.

96. The use or pharmaceutical composition of any of embodiments 69-95, wherein the divided dose is administered 2 to 3 times per day.

97. The use or pharmaceutical composition of any of embodiments 69-96, wherein the divided dose of component (a) comprises about 300-600 mg of component (a).

98. The use or pharmaceutical composition of any of embodiments 69-97, wherein the divided dose of component (a) is about 300-400 mg.

99. The use or pharmaceutical composition of any of embodiments 69-98, wherein the divided dose of component (a) is about 400 mg.

100. The use or pharmaceutical composition of any of embodiments 69-99, wherein the divided dose of component (a) is about 300 mg.

101. The use or pharmaceutical composition of any of embodiments 69-100, wherein the total daily dose of component (a) is about 900 to 1200 mg.

102. The use or pharmaceutical composition of any of embodiments 69-101, wherein the divided dose of component (b) is about 100-250 mg.

103. The use or pharmaceutical composition of any of embodiments 69-102, wherein the divided dose of component (b) is about 125-187.5 mg.

104. The use or pharmaceutical composition of any of embodiments 69-103, wherein the total daily dose of component (b) is about 375 mg to 562.5 mg.

105. The use or pharmaceutical composition of any of embodiments 69-104, wherein the divided dose of component (b) is about 125 mg.

106. The use or pharmaceutical composition of any of embodiments 69-105, wherein the divided dose of component (b) is about 187.5 mg.

107. The use or pharmaceutical composition of any of embodiments 69-106, wherein one or both of components (a) and (b) are formulated as a capsule, solutab, sachet, suspension, or tablet.

108. The use or pharmaceutical composition of any of embodiments 69-107, wherein one or both of components (a) and (b) are formulated as a capsule, and wherein the capsule is size 0, 1, or 2.

109. The use or pharmaceutical composition of any of embodiments 69-108, wherein one or both of components (a) and (b) are formulated for modified or extended release.

110. The use or pharmaceutical composition of any of embodiments 69-109, wherein the Enterobacteriaceae bacterium is a *Citrobacter freundii, Enterobacter aerogenes, Enterobacter cloacae, Escherichia coli, Klebsiella pneumoniae,* or *Klebsiella oxytoca.*

111. The use or pharmaceutical composition of any of embodiments 1-110, wherein the bacterial infection is a complicated UTI or acute pyelonephritis.

112. The pharmaceutical composition or use of any of embodiments 69-111, wherein the ESBL is a CTX-M, TEM, or SHV beta-lactamase.

113. The pharmaceutical composition or use of any of embodiments 69-112, wherein the ESBL is CTX-M-14 or CTX-M-15 or is of the same CTX-M group as CTX-M-14 or CTX-M-15.

114. The pharmaceutical composition or use of any of embodiments 69-113, wherein component (a) and component (b) are for use in an individual that has been previously administered an antibiotic to treat the bacterial infection.

115. The pharmaceutical composition or use of embodiment 114, wherein the previously administered antibiotic was a beta-lactam or a fluoroquinolone.

116. The pharmaceutical composition or use of any of embodiments 69-115, wherein component (a) and component (b) are for administration with food.

117. The pharmaceutical composition or use of any of embodiments 69-116, wherein component (a) and component (b) are for administration without food.

118. The pharmaceutical composition or use of any of embodiments 69-117, wherein the medicament or composition is for use in an individual that has a renal impairment.

119. The pharmaceutical composition or use of any of embodiments 69-118, wherein component (a) and component (b) are to be administered to the individual for at least about or about 3 days, 4 day, 5 days, 6 days, 7 days, 8 day, 9 days, 10 days, 11 days, 12 days, 13 days, 14 days, 15 days, 16 days, 17 days, 18 days, 19 days, or 20 days.

120. The pharmaceutical composition or use of any of embodiments 69-119, wherein component (a) and component (b) are to be administered for about 7 to 10 days.

121. The pharmaceutical composition or use of any of embodiments 69-120, wherein the individual is a human.

122. A kit comprising at least two oral dosage forms comprising (a) ceftibuten or a pharmaceutically acceptable salt thereof, or a hydrate of the foregoing and/or at least two oral dosage forms comprising (b) clavulanic acid, or a pharmaceutically acceptable salt thereof, wherein:

each dosage form is for oral administration to an individual of a unit dose;

the at least two oral dosage forms of component (a) and/or the at least two oral dosage forms of component (b) are for administering a divided dose of component (a) and/or component (b) two or more times a day, wherein component (a) is administered with component (b); and the divided dose is characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

123. The kit of embodiment 122, wherein component (a) and component (b) are combined in a single dosage form.

124. The kit of embodiment 122, wherein component (a) and component (b) are provided in separate dosage forms.

125. The kit of embodiment 122-124, further comprising instructions for use of component (a) and component (b).

126. The kit of embodiment 125, wherein the instructions specify the kit is for use in treating or prophylaxis of an Enterobacteriaceae bacterial infection.

127. The kit of embodiment 126, wherein the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL)

128. A kit for treating or prophylaxis of an Enterobacteriaceae bacterial infection, the kit comprising at least two oral dosage forms comprising (a) ceftibuten or a pharmaceutically acceptable salt thereof, or a hydrate of the foregoing and/or at least two oral dosage forms comprising (b) clavulanic acid, or a pharmaceutically acceptable salt thereof, wherein:

the bacterial infection is a urinary tract infection (UTI), upper respiratory infection, lower respiratory tract infection, primary or catheter-associated blood infection, neonatal sepsis, intra-abdominal infection, otitis media, or a wound infection, optionally wherein the bacterial infection is a complicated urinary tract infection (cUTI), acute pyelonephritis, uncomplicated UTI (uUTI), complicated intra-abdominal infection (cIAI) or community acquired pneumonia (CAP) and/or the bacterial infection is caused by an Enterobacteriaceae that expresses an extended-spectrum beta-lactamase (ESBL);

each dosage form is for oral administration to an individual of a unit dose:

the at least two oral dosage forms of component (a) and/or the at least two oral dosage forms of component (b) are for administering a divided dose of component (a) and/or component (b) two or more times a day, wherein component (a) is administered with component (b); and the divided dose is characterized by one or more of the following:

(i) the divided dose of component (a) is for administering a total daily dose of 800-1800 mg;

(ii) the divided dose of component (a) is at least or about at least 300 mg;

(iii) the divided dose of component (b) is for administering a total daily dose of 250-750 mg; and/or (iv) the divided dose of component (b) is at least or about at least 100 mg.

129. The kit of embodiment 128, wherein component (a) and component (b) are combined in a single dosage form.

130. The kit of embodiment 128, wherein component (a) and component (b) are provided in separate dosage forms.

131. The kit of any of embodiments 122-130, wherein the kit further comprises instructions for administering component (a) or component (b) to the individual.

132. The kit of embodiment 131, wherein the instructions specify the divided dose of component (a) and component (b) is for administration together.

133. The kit of embodiment 131, wherein the instructions specify the divided dose of component (a) and component (b) is for administration separately.

134. The kit of embodiment 131 or embodiment 133, wherein the instructions specify the divided dose of component (a) and the divided dose of component (b) is for administration simultaneously, concurrently or sequentially.

135. The kit of any of embodiments 131-134, wherein the instructions specify the component (a) and component (b) are for administration on an outpatient basis and/or are to be self-administered by the individual.

136. The kit of any of embodiments 122-135, wherein the divided dose is administered 2-5 times per day.

137. The kit of any of embodiments 122-136, wherein the divided dose is administered 2 or 3 times per day.

138. The kit of any of embodiments 132-137, wherein the instructions specify the divided dose of component (a) and the divided dose of component (b) is to be administered 2-5 times per day.

139. The kit of any of embodiments 132-137, wherein the instructions specify the divided dose of component (a) and the divided dose of component (b) is to be administered 2 or 3 times per day.

140. The kit of any of embodiments 122-139, wherein the divided dose of component (a) is about 300-600 mg.

141. The kit of any of embodiments 122-140, wherein the divided dose of component (a) is about 300-400 mg.

142. The kit of any of embodiments 122-141, wherein the divided dose of component (a) is about 400 mg.

143. The kit of any of embodiments 122-142, wherein the divided dose of component (a) is about 300 mg.

144. The kit of any of embodiments 122-143, wherein the total daily dose of component (a) is about 900 to 1200 mg.

145. The kit of any of embodiments 122-144, wherein the divided dose of component (b) is about 100-250 mg.

146. The kit of any of embodiments 122-145, wherein the divided dose of component (b) is about 125-187.5 mg.

147. The kit of any of embodiments 122-146, wherein the total daily dose of component (b) is about 375 mg to 562.5 mg.

148. The kit of any of embodiments 122-147, wherein the divided dose of component (b) is about 125 mg.

149. The kit of any of embodiments 122-148, wherein the divided dose of component (b) is about 187.5 mg.

150. The kit of any of embodiments 122-149, wherein the oral dosage form comprises a capsule, solutab, sachet, suspension, or tablet.

151. The kit of any of embodiments 122-150, wherein the oral dosage from is a capsule and the capsule is size 0, 1 or 2.

152. The kit of any of embodiments 122-151, wherein one or both of the oral dosage form of component (a) and component (b) are formulated for modified or extended release.

153. The kit of any of embodiments 122-152, wherein component (a) is ceftibuten dihydrate.

154. The kit of any of embodiments 122-153, wherein component (b) is potassium clavulanate.

155. The kit of any of embodiments 122-154, wherein component (a) and component (b) are packaged in the same container.

156. The kit of any of embodiments 122-155, wherein component (a) and component (b) are packaged in a different container.

157. The kit of embodiment 155 or embodiment 156, wherein the container is a divided container, wherein the at least two oral dosage forms of component (a) are separated from each other in the divided container and/or the at least two oral dosage forms of component (b) are separated from each other in the divided container.

158. The kit of embodiment 156 or embodiment 157, wherein the container is a blister pack.

159. The method of any of embodiments 1-68, further comprising administering at least one additional antibiotic.

160. The pharmaceutical composition or use of any of embodiments 69-121 for use with at least one additional antibiotic.

161. The kit of any of embodiments 122-158, wherein the kit comprises at least one additional antibiotic.

162. A method of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with a bacterium that expresses an extended-spectrum-β-lactamase (ESBL), and wherein the bacterial infection is a urinary tract infection (UTI), upper respiratory infection, lower respiratory tract infection, primary or catheter-associated blood infection, neonatal sepsis, intra-abdominal infection, otitis media, or a wound infection.

163. A method of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, and wherein the bacterial infection is associated with a bacterium that expresses an extended-spectrum-β-lactamase (ESBL) that is or is believed to be CTX-M-14 or CTX-M-15.

164. A method of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, wherein the bacterial infection is associated with a bacterium that expresses an extended-spectrum-β-lactamase (ESBL), and wherein the individual was previously administered an antibiotic to treat the bacterial infection.

165. A method of treating a bacterial infection in an individual, wherein the method comprises administering to the individual (a) ceftibuten or a pharmaceutically acceptable salt thereof, or a hydrate of the foregoing; and (b) clavulanic acid, or a pharmaceutically acceptable salt thereof, or a hydrate of the foregoing, wherein component (a) is administered separately, simultaneously or sequentially with component (b), and wherein the bacterial infection is associated with a bacterium that expresses an ESBL, and wherein the method is characterized by one or more of (i)-(iii):

(i) component (a) is administered to the individual at a daily dose of 800-1800 mg;
(ii) component (b) is administered to the individual at a daily dose of 250-750 mg;
(iii) a daily dose is administered in two or more divided doses of one or both of components (a) and (b).

166. The method of any of embodiments 1-68, 159 and 162-165, wherein component (a) is ceftibuten dihydrate.

167. The method of any of embodiments 1-68, 159 and 162-166, wherein component (b) is potassium clavulanate.

168. The method of any of embodiments 1-68, 159 and 162-167, wherein one or both of components (a) and (b) are administered orally.

169. The method of any of embodiments 1-68, 159 and 162-168, wherein component (a) is administered simultaneously or sequentially with component (b).

170. The method of any of embodiments 1-68, 159 and 162-169, wherein components (a) and (b) are administered together in the same pharmaceutical composition.

171. The method of any of embodiments 1-68, 159 and 162-170, wherein component (a) is administered to the individual at a ratio to component (b) of between 1:1-7:1.

172. The method of any of embodiments 1-68, 159 and 162-171, wherein component (a) is administered to the individual at a ratio to component (b) of between 1:1-3:1.

173. The method of embodiments 1-68, 159 and 162-172, wherein the method is characterized by one or more of (i)-(iii):

(i) component (a) is administered to the individual at a daily dose of 800-1800 mg;
(ii) component (b) is administered to the individual at a daily dose of 250-750 mg;
(iii) a daily dose is administered in two or more divided doses of one or both of components (a) and (b).

174. The method of any of embodiments 1-68, 159, 165 and 173, wherein the method is characterized by (i) and the daily dose is administered in two or more divided doses.

175. The method of any of embodiments 1-68, 159 165, 173, and 174, wherein the method is characterized by (ii) and the daily dose is administered in two or more divided doses.

176. The method of any of embodiments 1-68, 159, 165 and 173-175, wherein the method is characterized by (i), (ii), and (iii).

177. The method of any of embodiments 1-68, 159, 165 and 173-176, wherein the daily dose of one or both of components (a) and (b) is administered in 2-5 divided doses.

178. The method of any of embodiments 1-68, 159, 165 and 173-177, wherein the daily dose of one or both of components (a) and (b) is administered in 2 or 3 divided doses.

179. The method of any of embodiments 1-68, 159, 165 and 173-178, wherein each divided dose of component (a) comprises about 300-600 mg of component (a).

180. The method of any of embodiments 1-68, 159, 165 and 173-179, wherein each divided dose of component (a) comprises about 400 mg of component (a).

181. The method of any of embodiments 1-68, 159, 165 and 173-180, wherein each divided dose of component (b) comprises about 100-250 mg of component (b).

182. The method of any of embodiments 1-68, 159, 165 and 173-181, wherein each divided dose of component (b) comprises about 125 mg of component (b).

183. The method of any of embodiments 1-68, 159, 165 and 173-182, wherein each divided dose of component (b) comprises about 187.5 mg of component (b).

184. The method of any of embodiments 1-68, 159, and 162-183, wherein one or both of components (a) and (b) are formulated as a capsule, solutab, sachet, suspension, or tablet.

185. The method of any of embodiments 1-68, 159 and 162-184, wherein components (a) and (b) are formulated together.

186. The method of any of embodiments 1-68, 159, 162-185, wherein one or both of components (a) and (b) are formulated as a capsule, and wherein the capsule is size 0, 1, or 2.

187. The method of any of embodiments 1-68, 159, and 162-186, wherein one or both of components (a) and (b) are formulated for modified or extended release.

188. The method of any of embodiments 1-68, 159 and 162-187, wherein the bacterium is an Enterobacteriaceae.

189. The method of any of embodiments 1-68, 159 and 162-188, wherein the bacterium is a *Citrobacter freundii, Enterobacter aerogenes, Enterobacter cloacae, Escherichia coli, Klebsiella pneumoniae,* or *Klebsiella oxytoca.*

190. The method of any of embodiments 1-68, 159 and 163-189, wherein the bacterial infection is a urinary tract infection (UTI), upper respiratory infection, lower respiratory tract infection, primary or catheter-associated blood infection, neonatal sepsis, intra-abdominal infection, otitis media, or a wound infection.

191. The method of any of embodiments 1-68, 159 and 162-190, wherein the bacterial infection is a recurrent UTI, complicated UTI, uncomplicated UTI, bacteremic UTI, acute pyelonephritis, hospital-acquired pneumonia, ventilator-acquired pneumonia, or bronchitis.

192. The method of any of embodiments 1-68, 159 and 162-191, wherein the ESBL is inhibited by component (b).

193. The method of any of embodiments 1-68, 159, 162 and 164-192, wherein the ESBL is a CTX-M, TEM, or SHV beta-lactamase.

194. The method of any of embodiments 1-68, 159, 162 and 164-193, wherein the ESBL is or is believed to be CTX-M-14 or CTX-M-15.

195. The method of any of embodiments 1-68, 159 and 162-194, wherein the bacterium expresses CTX-M-14.

196. The method of any of embodiments 1-68, 159 and 162-195, wherein the bacterium expresses CTX-M-15.

197. The method of any of embodiments 1-68, 159 and 162-196, wherein the bacterium further expresses one or more additional beta-lactamase.

198. The method of embodiment 197, wherein the one or more additional beta-lactamase is independently CTX-M, a FEC, a KLUA, a KLUG, a TEM, a TOHO, or a SHV beta-lactamase.

199. The method of embodiment 197 or 198, wherein the one or more additional beta-lactamase is independently CTX-M, CTX-M-1, CTX-M-2, CTX-M-3, CTX-M-4, CTX-M-4L or CTX-M-89, CTX-M-5, CTX-M-6, CTX-M-7, CTX-M-8, CTX-M-9, CTX-M-10, CTX-M-12, CTX-M-13, CTX-M-14, CTX-M-15, CTX-M-16, CTX-M-17, CTX-M-19, CTX-M-20, CTX-M-21, CTX-M-22, CTX-M-23, CTX-M-24, CTX-M-25, CTX-M-26, CTX-M-27, CTX-M-28, FEC-1, KLUA-1, KLUA-5, KLUA-6, KLUA-8, KLUA-9, KLUA-10, KLUA-11, KLUG-1, SHV-2, SHV-7, SHV-12, TEM-1, TEM-OSBL, or TOHO-1.

200. The method of any of embodiments 197-199, wherein the one or more additional beta-lactamase is independently CTX-M-1, CTX-M-3, CTX-M-14, CTX-M-15, SHV-2, SHV-7, SHV-12, TEM-1, or TEM-OSBL.

201. The method of any of embodiments 1-68, 159 and 162-200, wherein the bacterium has an antibiotic resistant phenotype.

202. The method of embodiment 201, wherein the antibiotic resistant phenotype is resistance to a fluoroquinolone, a beta-lactam, or a beta-lactam:beta-lactamase inhibitor combination.

203. The method of embodiment 201 or 202, wherein the antibiotic resistant phenotype is resistance to amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, ciprofloxacin, doripenem, gentamicin, imipenem, levofloxacin, loracarbef, meropenem, piperacillin, or tobramycin.

204. The method of any of embodiments 201-203, wherein the antibiotic resistant phenotype is ST131.

205. The method of any of embodiments 1-68, 159 and 162-204, wherein the bacterium does not express a protein selected from the group consisting of an AmpC, a KPC, an OXA, an NDM, or an OMP.

206. The method of any of embodiments 1-68, 159 and 162-205, wherein the bacterium does not express an AmpC.

207. The method of any of embodiments 1-68, 159 and 162-206, wherein the bacterium does not express a KPC.

208. The method of any of embodiments 1-68, 159 and 162-207, wherein the bacterium does not express an OXA.

209. The method of any of embodiments 1-68, 159 and 162-208, wherein the bacterium does not express an NDM.

210. The method of any of embodiments 1-68, 159 and 162-209, wherein the bacterium does not express an OMP.

211. The method of any of embodiments 1-68, 159, 162, 163, and 165-210, wherein the individual was previously administered an antibiotic to treat the bacterial infection.

212. The method of embodiment 164 or 211, wherein the previously administered antibiotic was a beta-lactam or a fluoroquinolone.

213. The method of embodiment 212, wherein the previously administered antibiotic was a beta-lactam which was a penicillin derivative, cephalosporin, monobactam, or carbapenem.

214. The method of embodiment 212 or 213, wherein the previously administered antibiotic was a beta-lactam which was amikacin, amoxicillin, ampicillin, aztreonam, cefaclor, cefadroxil, cefepime, cefixime, ceftibuten, cefdinir, cefditoren, cefotaxime, cefpodoxime, cefprozil, ceftaroline, ceftazidime, ceftriaxone, cefuroxime, cephalexin, cephradine, doripenem, gentamicin, imipenem, loracarbef, meropenem, piperacillin, or tobramycin.

215. The method of any of embodiments 212-214, wherein the previously administered antibiotic was a beta-lactam that was administered with a beta-lactamase inhibitor.

216. The method of embodiment 215, wherein the previously administered beta-lactamase inhibitor was clavulanate, tazobactam, avibactam, or sulbactam.

217. The method of embodiment 216, wherein the previously administered antibiotic was a fluoroquinolone which was levofloxacin or ciprofloxacin.

218. The method of any of embodiments 164 and 211-217, wherein the previously administered antibiotic was not fully effective at treating the bacterial infection.

219. The method of any of embodiments 164 and 211-218, wherein the previously administered antibiotic was an intravenously administered antibiotic.

220. The method of any of embodiments 1-68, 159 and 162-219, wherein components (a) and (b) are administered orally, and wherein the oral administration of component (a) and (b) is a step-down therapy or is the oral portion of an intravenous to oral therapy switch.

221. A kit comprising (a) ceftibuten or a pharmaceutically acceptable salt thereof, or a hydrate of the foregoing; (b) clavulanic acid, or a pharmaceutically acceptable salt thereof, or a hydrate of the foregoing, and wherein the bacterial infection is associated with a bacterium that expresses an extended-spectrum-β-lactamase (ESBL); and (c) instructions for performing the method of any one of embodiments 1-68, 159 and 162-220.

222. A kit comprising (a) ceftibuten or a pharmaceutically acceptable salt thereof, or a hydrate of the foregoing; (b) clavulanic acid, or a pharmaceutically acceptable salt thereof, or a hydrate of the foregoing, and wherein the bacterial infection is associated with a bacterium that expresses an extended-spectrum-β-lactamase (ESBL); and (c) instructions for administering an effective amount of components (a) and (b) for treatment of a bacterial infection to an individual in need thereof, wherein the bacterial infection is associated with a bacterium that expresses an extended-spectrum-β-lactamase (ESBL).

It will be appreciated that details of the foregoing embodiments, given for purposes of illustration, are not to be construed as limiting the scope of this invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

VII. EXAMPLES

The following examples are included for illustrative purposes only and are not intended to limit the scope of the invention.

Example 1: In Vitro Microbiological Activity of a Panel of Approved Antibiotics Against *Escherichia coli* Isolates with an ESBL-Phenotype A surveillance program was carried out in the United States on contemporary *E. coli* isolates with an ESBL-producing phenotype to assess the microbiological activity of a panel of approved antibiotics. The microbiological activity was determined using Clinical and Laboratory Standards Institute (CLSI) and European Committee on Antimicrobial Susceptibility Testing (EUCAST) breakpoints. As shown in Table 1, the results showed that the $MIC_{90}$ was above the breakpoint for susceptibility for cephalosporins (ceftazidime and ceftriaxone), trimethoprim/sulfamethoxazole, and a fluoroquinolone (levofloxacin).

TABLE 1

In vitro Microbiological Activity of a Panel of Approved Antibiotics Against *Escherichia coli* Isolates with an ESBL-Phenotype

| Drug | *E. coli* (n = 124)<br>$MIC_{90}$ (µg/mL)* |
|---|---|
| Aztreonam | >16 |
| Ceftazidime | >32 |
| Ceftriaxone | >8 |
| Piperacillin/Tazobactam | 64 |
| Levofloxacin | >4 |
| Trimethoprim/Sulfamethoxazole | >4 |
| Gentamicin | >8 |
| Tobramycin | >8 |
| Amikacin | 8 |
| Imipenem | 0.25 |
| Meropenem | 0.03 |
| Doripenem | ≤0.06 |
| Colistin | 0.25 |
| Tigecycline | 0.25 |

*$MIC_{90}$: MIC required to inhibit the growth of 90% of organisms.
$MIC_{90}$ values in bold are resistant according to current CLSI/EUCAST breakpoints.
$MIC_{90}$ values that are not in bold are susceptible according to current CLSI/EUCAST breakpoints.
CLSI: Clinical & Laboratory Standards Institute;
EUCAST: European Committee on Antimicrobial Susceptibility Testing Example 2: Evaluation of Combinations of Cephalosporins and β-Lactamase Inhibitors A. Initial MIC Evaluation of Cephalosporins and β-Lactamase Inhibitor Combinations Twelve orally-bioavailable cephalosporins of various generations have been marketed: cephalexin, cefadroxil, cephradine, cefaclor, cefuroxime, loracarbef, cefprozil, cefdinir, cefixime, ceftibuten, cefpodoxime and cefditoren. The initial evaluation described herein focused on the orally-bioavailable third-generation cephalosporins, cefixime, ceftibuten, and cefpodoxime, due to their improved spectrum of activity against Gram-negative pathogens. The third-generation cephalosporin cefditoren was not initially tested.

The in vitro activity of the orally-bioavailable third-generation cephalosporins ceftibuten, cefpodoxime, and cefixime and the forth-generation cephalosporin cefepime were characterized by determining the minimum inhibitory concentration (MIC) of the compound alone or in combination with one or both of the currently marketed β-lactamase inhibitors, clavulanate and tazobactam. For comparison, the MICs of clavulanate alone, tazobactam alone, amoxicillin+clavulanate, and piperacillin+tazobactam were also determined. Clavulanate was tested at a fixed 2:1 ratio (cephalosporin:β-lactamase inhibitor) according to the methods used for testing clavulanate with amoxicillin; tazobactam was tested at a fixed 4 µg/mL concentration as is done with tazobactam in combination with piperacillin (CLSI M100-S25, Performance Standards for Antimicrobial Susceptibility Testing, January 2015).

MIC values were determined for the combinations against nineteen isolates of Enterobacteriaceae species bacteria, including *Citrobacter freundii*, *Enterobacter aerogenes*, *Enterobacter cloacae*, *Escherichia coli*, *Klebsiella pneumoniae*, and *Klebsiella oxytoca*. The isolates were chosen to represent the major species of Enterobacteriaceae encountered in urinary tract infections (Lancet 2015; 385:1949-1956) and included isolates that produce individual and multiple β-lactamases (including Ambler Class A ESBLs and Ambler Class C β-lactamases), which were expected to be resistant to cephalosporins (Clin Infect Dis 2013; 56:641-648). Activity against isolates in this panel is expected to reflect activity against clinical isolates of the same and/or other Enterobacteriaceae species producing the same or similar β-lactamases. The results these studies are shown in Tables 2a-b.

TABLE 2a

MIC values Determined for Cephalosporins With and Without β-Lactamase Inhibitors Against a Panel of Contemporary Clinical Enterobacteriacceae Isolates that are Known to Express Extended-Spectrum β-Lactamases

| Isolate[a] | Extended Spectrum β-Lactamases Encoded by the Isolate | Cefixime MIC (CLSI susceptible ≤ 1) | | | Cefpodoxime MIC (CLSI susceptible ≤ 2) | | |
|---|---|---|---|---|---|---|---|
| | | alone | +Clavulanate | +Tazobactam | alone | +Clavulanate | +Tazobactam |
| ACFR1034 | CTX-M-15, TEM-OSBL | >64 | 64 | >64 | >64 | 32 | >64 |
| ACFR1035 | CTX-M-3, TEM-OSBL | >64 | 2 | 4 | >64 | 4 | >64 |
| AEAE1027 | CTX-M-14 | 8 | 1 | 0.25 | >64 | 2 | 0.5 |
| AEAE1029 | CTX-M-15 | >64 | 1 | 4 | >64 | 2 | 8 |
| AECL1065 | CTX-M-15 | >64 | >64 | >64 | >64 | >64 | >64 |
| AECL1067 | CTX-M-3 | >64 | >64 | 16 | >64 | >64 | 8 |
| AECO1078 | CTX-M-15 | >64 | 1 | 1 | >64 | 2 | 1 |
| AECO1147 | CTX-M-15 | ND | 2 | 1 | >64 | 2 | 2 |
| AECO1157 | CTX-M-15, TEM-OSBL | >64 | 1 | 1 | >64 | 2 | 8 |
| AECO1159 | CTX-M-15 | >64 | 2 | 4 | >64 | 4 | 16 |
| AECO1169 | CTX-M-1, TEM-OSBL | 16 | 1 | 0.5 | >64 | 2 | 1 |
| AECO1172 | CTX-M-14 | 16 | 1 | 1 | >64 | 4 | 1 |
| AKOX1005 | SHV-2, TEM-1, DHA-1 | 16 | 4 | ND | 32 | 4 | 0.125 |
| AKOX1009 | CTX-M-15 | >64 | 0.5 | 0.125 | >64 | 1 | ND |
| AKPN1159 | SHV-12 | 32 | 0.25 | 0.063 | 64 | 0.5 | 0.25 |
| AKPN1161 | SHV-7 | 32 | 0.5 | 0.5 | 16 | 1 | 1 |
| AKPN1162 | CTX-M-15, SHV-12 | >64 | 1 | ND | >64 | 2 | 16 |
| AKPN1166 | CTX-M-14, SHV-12 | >64 | 0.5 | 1 | >64 | 1 | 1 |
| AKPN1167 | SHV-2 | 8 | 0.5 | 8 | >64 | 1 | >64 |
| AECO001 | None | 1 | 1 | 0.25 | 0.5 | 0.5 | 0.5 |

| Isolate[a] | Ceftibuten MIC (EUCAST susceptible ≤ 1) | | | Cefepime MIC (CLSI susceptible ≤ 2) | |
|---|---|---|---|---|---|
| | alone | +Clavulanate | +Tazobactam | alone | +Tazobactam |
| ACFR1034 | >64 | 32 | >64 | >32 | 8 |
| ACFR1035 | 16 | 2 | 2 | >32 | 2 |
| AEAE1027 | 1 | 1 | 0.25 | 8 | 0.063 |
| AEAE1029 | 8 | 0.5 | 0.5 | >32 | 0.25 |
| AECL1065 | >64 | >64 | >64 | >32 | >32 |
| AECL1067 | 32 | >64 | 16 | >32 | 0.25 |
| AECO1078 | 32 | 1 | 0.5 | >32 | 0.125 |
| AECO1147 | 4 | 1 | 2 | 4 | 0.5 |
| AECO1157 | 8 | 0.5 | 0.25 | 32 | 2 |
| AECO1159 | 16 | 1 | 1 | >32 | 8 |
| AECO1169 | 1 | 0.5 | 0.25 | >32 | 0.125 |
| AECO1172 | 2 | 2 | 1 | >32 | 0.125 |
| AKOX1005 | 2 | ND | ≤0.063 | 0.25 | ≤0.031 |
| AKOX1009 | 4 | 0.25 | ≤0.063 | 32 | 0.125 |
| AKPN1159 | 4 | ≤0.063 | ≤0.063 | 2 | 0.25 |
| AKPN1161 | 2 | 0.5 | 0.25 | 1 | 0.5 |
| AKPN1162 | 32 | 0.5 | 0.063 | >32 | ND |
| AKPN1166 | 4 | 0.25 | 0.125 | 4 | 0.25 |
| AKPN1167 | 2 | 0.5 | 2 | 8 | 8 |
| AECO001 | 0.5 | 0.5 | 0.25 | ≤0.031 | 0.063 |

[a]Isolate genus/species followed by ID number: ACFR, *Citrobacter freundii*; AEAE, *Enterobacter aerogenes*; AECL, *Enterobacter cloacae*; AECO, *Escherichia coli*; AKOX, *Klebsiella oxytoca*; AKPN, *Klebstella pneumoniae*.
CLSI: Clinical & Laboratory Standards Institute; EUCAST: European Committee on Antimicrobial Susceptibility Testing.

TABLE 2b

MIC Values Determined for Available Penicillin + β-Lactamase Inhibitor Combinations, and β-Lactamase Inhibitors Alone Against a Panel of Contemporary Clinical Enterobacteriaceae Isolates that are Known to Express Extended-Spectrum β-Lactamases

| Isolate[a] | Extended Spectrum B-Lactamases Encoded by the Strain | Amoxicillin + Clavulanate MIC (2:1) (CLSI susceptible ≤8) | Piperacillin + Tazobactam MIC (Tazobactam at 4 μg/mL) (CLSI susceptible ≤16) | Clavulanate alone MIC | Tazobactam alone MIC |
|---|---|---|---|---|---|
| ACFR1034 | CTX-M-15, TEM-OSBL | 32 | >64 | 32 | >64 |
| ACFR1035 | CTX-M-3, TEM-OSBL | >32 | >64 | 32 | >64 |
| AEAE1027 | CTX-M-14 | >32 | 4 | 32 | >64 |

TABLE 2b-continued

MIC Values Determined for Available Penicillin + β-Lactamase Inhibitor Combinations, and β-Lactamase Inhibitors Alone Against a Panel of Contemporary Clinical Enterobacteriaceae Isolates that are Known to Express Extended-Spectrum β-Lactamases

| Isolate[a] | Extended Spectrum B-Lactamases Encoded by the Strain | Amoxicillin + Clavulanate MIC (2:1) (CLSI susceptible ≤8) | Piperacillin + Tazobactam MIC (Tazobactam at 4 μg/mL) (CLSI susceptible ≤16) | Clavulanate alone MIC | Tazobactam alone MIC |
|---|---|---|---|---|---|
| AEAE1029 | CTX-M-15 | >32 | 32 | 32 | >64 |
| AECL1065 | CTX-M-15 | >32 | >64 | 64 | >64 |
| AECL1067 | CTX-M-3 | >32 | 4 | 64 | >64 |
| AECO1078 | CTX-M-15 | 16 | 2 | 32 | >64 |
| AECO1147 | CTX-M-15 | 16 | 64 | 32 | >64 |
| AECO1157 | CTX-M-15, TEM-OSBL | 32 | >64 | 32 | >64 |
| AECO1159 | CTX-M-15 | >32 | >64 | 32 | >64 |
| AECO1169 | CTX-M-1, TEM-OSBL | 8 | 4 | 32 | >64 |
| AECO1172 | CTX-M-14 | 16 | 2 | 32 | >64 |
| AKOX1005 | SHV-2, TEM-1, DHA-1 | >32 | 2 | 32 | >64 |
| AKOX1009 | CTX-M-15 | 16 | 16 | 32 | >64 |
| AKPN1159 | SHV-12 | 32 | ND | 32 | >64 |
| AKPN1161 | SHV-7 | 4 | 16 | 16 | >64 |
| AKPN1162 | CTX-M-15, SHV-12 | 8 | 8 | 32 | >64 |
| AKPN1166 | CTX-M-14, SHV-12 | 16 | 64 | 32 | >64 |
| AKPN1167 | SHV-2 | 16 | >64 | 16 | >64 |
| AECO001 | None | 4 | 2 | 32 | >64 |

[a]Isolate genus/species followed by ID number: ACFR, *Citrobacter freundii*, AEAE, *Enterobacter aerogenes*; AECL, *Enterobacter cloacae*; AECO, *Escherichia coli*; AKOX, *Klebsiella oxytoca*; AKPN, *Klebsiella pneumoniae*. CLSI: Clinical & Laboratory Standards Institute.

The MICs for cefixime, cefpodoxime and ceftibuten against ESBL-producing Enterobacteriaceae tested in Table 2a-b were above the CLSI/EUCAST (CLSI: Clinical & Laboratory Standards Institute; EUCAST: European Committee on Antimicrobial Susceptibility Testing) MIC breakpoints for the approved dosing regimens of these drugs. Therefore, cefixime, cefpodoxime, and ceftibuten would not be expected to be effective against contemporary ESBL-producing Enterobacteriaceae. As demonstrated in Table 2b, while the combination of a β-lactam (e.g. a penicillin) with a β-lactamase inhibitor (e.g. amoxicillin+clavulanate or piperacillin+tazobactam) was active against Enterobacteriaceae that do not produce ESBLs (e.g. AECO001), ESBL-producing Enterobacteriaceae (e.g. AECO1159) were generally resistant to the combination. Thus, the mere addition of a β-lactamase inhibitor does not necessarily restore the activity of any β-lactam drug against an ESBL-producing Enterobacteriaceae.

As shown in Table 2a, many of the ESBL-producing isolates were unexpectedly sensitive to low concentrations of ceftibuten alone, compared with other orally-bioavailable third-generation cephalosporins (cefixime or cefpodoxime) or cefepime (a fourth-generation intravenous cephalosporin used as a comparator agent in this assay). For example, ceftibuten had an MIC<8 μg/mL for 10 of 19 ESBL-producing isolates. However, neither cefpodoxime nor cefixime had an MIC<8 μg/mL for any ESBL-producing isolates in this panel. Cefepime also fell short of ceftibuten, achieving an MIC<8 μg/mL for only 4 of 19 ESBL-producing isolates. Importantly, the results showed that ceftibuten was uniquely and unexpectedly more resistant to degradation by contemporary CTX-M-14 (e.g. AEAE1027, AECO1172) and CTX-M15 (e.g. AEAE1029, AKOX1009) expressing isolates. CTX-M-14 and CTX-M15 expressing isolates account for the majority of ESBL-producing isolates in the USA (Clin Infect Dis 2013; 56:641-648). Despite this relative advantage of ceftibuten over other drugs in the same class, in the absence of a β-lactamase inhibitor, the majority of ESBL-producing isolates described herein were not susceptible to ceftibuten alone at currently marketed doses.

As shown in Table 2a, the addition of clavulanate to ceftibuten was unexpectedly effective in isolates that have relatively high MICs for each agent alone. This was unexpected, given that a recent survey of potentially useful older antibiotics by international experts concluded that ceftibuten did not have potential against resistant bacteria (Clin Infect Dis 2012; 54:268-274). Specifically, the addition of clavulanate to ceftibuten lowered the MICs from 16 μg/mL to 2 μg/mL against *Citrobacter freundii* ACFR1035, from 8 μg/mL to 0.5 μg/mL against *Enterobacter aerogenes* AEAE1029, from 4 μg/mL to 1 μg/mL against *E. coli* AECO1147 (CTX-M-15 producer), from 8 μg/mL to 0.5 μg/mL against *E. coli* AECO1157 (CTX-M-15 and TEM producer), from 16 μg/mL to 1 μg/mL against *E. coli* AECO1159 (CTX-M-15 producer), from 4 μg/mL to 0.25 μg/mL against *Klebsiella oxytoca* AKOX1009 (CTX-M-15 producer), from 32 μg/mL to 0.5 μg/mL against *Klebsiella pneumoniae* AKPN1162 (CTX-M-15 and SHV-12 producer) and from 4 μg/mL to 0.25 μg/mL against *K. pneumoniae* AKPN1166 (CTX-M-14 and SHV-12 producer). Similar results were observed for combinations with tazobactam, but tazobactam does not have a known oral formulation, limiting its therapeutic application.

The effectiveness of the clavulanate and ceftibuten combination was seen in isolates with both relatively high and low MICs for ceftibuten alone. For instance, AKPN1162 was relatively resistant to ceftibuten alone and showed a 64-fold reduction in MIC when clavulanate was added to ceftibuten (the MIC was reduced from 32 to 0.5 μg/mL). Similarly, while AKPN1159 was 8-fold more susceptible to ceftibuten alone, the addition of clavulanate to ceftibuten showed an equivalent ≥64-fold reduction in the MIC (the MIC was reduced from 4 to ≤0.063 μg/mL). The observed effectiveness across the MIC range was an unexpected finding with respect to the addition of clavulanate to ceftibuten, and was exemplified by considering the proportion of ESBL-producing isolates having an MIC<1 μg/mL for the combination of ceftibuten+clavulanate (9 of 19 isolates tested) compared to cefixime+clavulanate (5 of 19 isolates tested) or cefpodoxime (1 of 19 isolates tested). The persistence of increased effectiveness between ceftibuten and clavulanate at the low end of the MIC range is critical for ceftibuten to achieve the PK/PD target of 40% fT>MIC, as outlined in Example 5 below.

Other isolates tested (*Citrobacter freundii* ACFR1034, *Enterobacter cloacae* AECL1065 and *Enterobacter cloacae* AECL1067) showed resistance to combinations of any one of the three orally-bioavailable third-generation cephalosporins with clavulanate. However, these species often express a chromosomal AmpC β-lactamase (Scand J Infect Dis Suppl 1986; 49:38-45), which is known to hydrolyze certain cephalosporins and against which clavulanate has no appreciable activity. Despite ceftibuten's differentially greater activity against ESBL-producing isolates, described above, AmpC-expressing isolates showed equivalently high MICs to ceftibuten, cefixime and cefpodoxime, irrespective of the addition of clavulanate. This highlights the non-obvious nature of ceftibuten's activity against ESBL-producing Enterobacteriaceae (especially CTX-M-15 and CTX-M-14 producers), and the effectiveness of ceftibuten and clavulanate in these isolates, which cannot be applied broadly across all Enterobacteriaceae or to all β-lactamases.

B. Expanded MIC Evaluation of Combinations of Cephalosporins and β-Lactamase Inhibitors Based on the initial in vitro evaluation of cephalosporin and β-lactamase inhibitor combinations, the MIC was determined for an expanded panel of cephalosporins in combination with the β-lactamase inhibitor clavulanate against 13 Enterobacteriaceae isolates. Cephalosporin and clavulanate were tested at a fixed 2:1 ratio according to the methods used for testing clavulanate with amoxicillin as described above. The tested cephalosporins included cefuroxime (CFU), cefaclor (CFC), cefprozil (CPR), cefalexin (CFL), loracarbef (LCB), cefditoren (CDT), cefpodoxime (CPD), cefdinir (CFD), cefixime (CFX), and ceftibuten (CTB). Results are shown in Table 3. The combination of ceftibuten and clavulanate consistently demonstrated the lowest MIC of the 10 cephalosporins tested. For comparison, MICs for amoxicillin-clavulanate and ciprofloxacin were also determined.

Example 3: Assessment of Bactericidal Activity of Ceftibuten and Clavulanate Combination Against Extended-Spectrum Beta-Lactamase (ESBL) Enterobacteriaceae A. Minimum Bactericidal Concentration The bactericidal activity of ceftibuten-clavulanate against extended-spectrum beta-lactamase (ESBL) Enterobacteriaceae was assessed by determining the minimum bactericidal concentration (MBC) against 9 bacterial isolates (6 *Escherichia coli*, 2 *Klebsiella pneumoniae* and 1 *Enterobacter aerogenes*) expressing ESBLs from the CTX-M and SHV families.

To determine the MBC, log-phase bacterial cultures were mixed with serial dilutions of antibiotics according to Clinical and Laboratory Standards Institute (CLSI) guidelines for determination of the minimum inhibitory concentration (MIC) by the broth microdilution method. (CLSI Document M07-A9, Vol. 32, No. 2. January 2012). The ceftibuten: clavulanate mass ratio was 2:1 across the dilution series. Samples taken from antibiotic-free wells of the assay plates at the beginning of the experiment were serially diluted in sterile saline and spread on agar plates to determine the inoculum cell density. After 18-20 hours of incubation at 35° C. in ambient air, MIC values were recorded. Plates were shaken for 1 minute on a microtiter plate shaker, then returned to the incubator. After 24 hours of total incubation, plates were shaken again for 1 minute. Samples of 10 μL were taken from wells at the MIC and higher antibiotic concentrations, diluted into 100 μL of liquid media on the surface of an agar plate, and spread across the plate. After overnight incubation at 35° C., colonies were counted to determine the MBC, defined as the lowest concentration of antibiotic that reduced the viable cell density by ≥3 $\log_{10}$ compared to the cell density of the untreated control measured at the beginning of the experiment.

TABLE 3

MIC Values of Expanded Panel of Cephalosporins + Clavulanate

| Organism | ESBL | Amoxicillin-Clavulanate (2:1) MIC (μg/mL) | Ciprofloxacin MIC (μg/mL) | Cephalosporin + Clavulanate (2:1) MIC (μg/mL) | | | | | | | | | |
|---|---|---|---|---|---|---|---|---|---|---|---|---|---|
| | | | | CFU | CFC | CPR | CFL | LCB | CDT | CPD | CFD | CFX | CTB |
| E. coli | CTX-M-15, TEM-1 | 16 | ≤0.03 | 8 | 2 | 4 | 16 | 2 | 1 | 2 | 2 | 1 | 0.5 |
| E. coli | CTX-M-15, TEM-1 | 8 | >4 | 8 | 2 | 4 | 8 | 2 | 1 | 2 | 2 | 1 | 0.5 |
| E. coli | CTX-M-14 | 8 | ≤0.03 | 8 | 2 | 4 | 8 | 2 | 1 | 2 | 2 | 1 | 0.5 |
| K. pneumoniae | SHV-5, TEM-1 | 8 | 0.25 | 8 | 1 | 1 | 8 | 1 | 2 | 1 | 0.5 | 0.25 | 0.12 |
| K. pneumoniae | SHV WT, CTX-M-15, OXA-1/30-like | 16 | 1 | 8 | 2 | 4 | 4 | 2 | 1 | 2 | 2 | 2 | 0.5 |
| K. pneumoniae | SHV-11, SHV-12, TEM-1 | 8 | >4 | 8 | 1 | 2 | 8 | 1 | 1 | 1 | 0.5 | 0.5 | 0.25 |
| K. pneumoniae | SHV-30 | 8 | 0.12 | 16 | 2 | 2 | 16 | 2 | 2 | 2 | 1 | 0.5 | 0.25 |
| P. mirabilis | CTX-M-15-like, TEM WT | 2 | ≤0.03 | 1 | 1 | 1 | 8 | 2 | 0.12 | 0.25 | 0.25 | 0.03 | 0.03 |
| P. mirabilis | CTX-M-14-like, TEM WT | 8 | 4 | 4 | 2 | 4 | 16 | 4 | 0.25 | 0.5 | 1 | 0.06 | 0.03 |
| P. mirabilis | | 0.5 | >4 | 1 | 1 | 1 | 8 | 1 | 0.06 | 0.06 | 0.06 | 0.015 | <0.015 |
| P. mirabilis | | 1 | ≤0.03 | 1 | 1 | 1 | 8 | 1 | 0.06 | 0.03 | 0.06 | 0.015 | <0.015 |
| E. coli | | 8 | >4 | 8 | 2 | 2 | 8 | 1 | 0.25 | 0.5 | 0.25 | 0.5 | 0.25 |
| K. pneumoniae | | 2 | >4 | 2 | 0.5 | 1 | 4 | 0.5 | 0.25 | 0.12 | 0.12 | 0.12 | 0.06 |

CFU: Cefuroxime, CFC: Cefaclor, CPR: Cefprozil, CFL: Cefalexin, LCB: Loracarbef, CDT Cefditoren, CPD: Cefpodoxime, CFD: Cefdinir, CFX: Cefixime, CTB: Ceftibuten Table 4 lists the analyzed bacterial strains, including the ESBL produced by each strain (beta-lactamase genotype) and antibiotic resistance of each strain. Table 4 also sets forth the MIC and MBC values obtained in this experiment. For 8 of 9 strains, the MBC at 24 hours was equal to the MIC (=MIC). For 1 strain, the MBC at 24 hours was 2-fold higher than the MIC. An agent is usually regarded as bactericidal if the MBC is no more than four times the MIC. (J Antimicrob Chemother (2006) 58 (6): 1107-1117). These results are consistent with a finding that Ceftibuten-clavulanate is bactericidal ($\geq 3$ $\log_{10}$ reduction in viable cell density) against ESBL *E. coli, K. pneumoniae*, and *Enterobacter aerogenes*.

TABLE 4

Minimum Bactericidal Concentrations of Ceftibuten-Clavulanate Against ESBL Enterobacteriaceae

| Strain | Beta-lactamase(s) | Antibiotic Resistance | Ceftibuten-clavulanate MIC (µg/mL) | MBC (relative to MIC) |
|---|---|---|---|---|
| AECO1138 | CTX-M-55 | AMK, GEN, TOB | 1 | ~=MIC |
| AECO1155 | CTX-M-15 | AMP, CPT, CTX, LVX, TOB | 1 | =MIC |
| AECO1156 | CTX-M-15, TEM-OSBL | AMK, AMP, CAZ, CTR, FEP, GEN, LVX, TOB | 0.5 | =MIC |
| AECO1157 | CTX-M-15, TEM-OSBL | CAZ, CTR, CTX, FEP,LVX, PTZ, TOB | 0.25 | =MIC |
| AECO1159 | CTX-M-15 | AMK, AMP, ATM, CAZ, CPT, CTX, FEP, LVX, PTZ, TOB | 1 | =MIC |
| AECO1162 | CTX-M-14 | AMP, ATM, CPT, CTX, LVX | 0.5 | =MIC |
| AKPN1159 | SHV-12 | AMP, ATM, CAZ, CPT, CTX, FEP, PTZ | 0.06 | =MIC |
| AKPN1168 | SHV-5 | AMP, ATM, CAZ, CPT, CTX | 0.12 | 2 × MIC |
| AEAE1019 | CTX-M-15, TEM-OSBL | AMP, ATM, CAZ, CPT, FEP | 0.25 | =MIC |

AEAE = *Enterobacter aerogenes*; AECO = *Escherichia coli*; AKPN = *Klebsiella pneumoniae*; AMK = amikacin; AMP = ampicillin; ATM = aztreonam; CAZ = ceftazidime; CPT = ceftaroline; CTR = ceftriaxone; CTX = cefotaxime; FEP = cefepime; GEN = gentamicin; LVX = levofloxacin; MBC = minimum bactericidal concentration; MIC = minimum inhibitory concentration; OSBL = original-spectrum beta-lactamase; PTZ = piperacillin-tazobactam; TOB = tobramycin.

B. Killing Kinetics of Ceftibuten-Clavulanate

The killing kinetics of ceftibuten-clavulanate were measured against 6 bacterial isolates (4 *Escherichia coli* and 2 *Klebsiella pneumoniae*) expressing CTX-M and SHV ESBLs. Log-phase bacterial cultures were mixed with antibiotics in glass culture tubes and incubated at 37° C. with shaking. Viability of the cultures over time was monitored by serially diluting samples in sterile saline and spreading the diluted samples onto agar plates. For cultures treated with the ceftibuten-clavulanate combination, the mass ratio was 2:1 across the dilution series. For cultures treated with ceftibuten alone, the concentration was equivalent to 4-fold above the MIC of the ceftibuten-clavulanate combination. Meropenem was included as a comparator at 8-fold above its MIC.

Table 5a sets forth the analyzed bacterial strains, including the ESBL produced by each strain (beta-lactamase genotype) and the MICs of ceftibuten-clavulanate, ceftibuten and meropenem against isolates in the time-kill experiment. For each bacterial strain, viable cell densities of representative cultures as monitored in the time-kill experiments are listed in Table 5b and depicted graphically in FIGS. 1A-1F.

TABLE 5a

MICs of Ceftibuten-Clavulanate, Ceftibuten, and Meropenem Against Isolates Analyzed in Time-Kill Experiments

| Strain Code and Beta-lactamase | MIC (mg/L) | | |
|---|---|---|---|
| | Ceftibuten-clavulanate | Ceftibuten | Meropenem |
| AECO1156 (CTXM-15, TEM-OSBL) | 0.5 | 16 | 0.03 |
| AECO1157 (CTXM-15, TEM-OSBL) | 0.5 | 8 | 0.03 |
| AECO1162 (CTX-M-14) | 0.5 | 8 | 0.03 |
| AECO1166 (SHV-12) | 0.12 | 2 | 0.016 |
| AKPN1159 (SHV-12) | 0.06 | 4 | 0.03 |
| AKP1162 (SHV-12, CTX-M-15) | 0.25 | 32 | 0.06 |

AECO = *Escherichia coli*; AKPN = *Klebsiella pneumoniae*; MIC = minimum inhibitory concentration; OSBL = original-spectrum beta-lactamase.

TABLE 5b

Change in Viable Cell Counts Over Time for ESBL *E. coli* and *K.pneumoniae* Treated With Ceftibuten-Clavulanate, Ceftibuten, or Meropenem

| Strain Code and Beta-lactamase | Time (h) | Change in $\log_{10}$ CFU/mL From Inoculum (0 hr) | | | | | |
|---|---|---|---|---|---|---|---|
| | | No Abx | CTB Only[1] | CTB + CLA | | | MEM |
| | | | | 2X MIC | 4X MIC | 8X MIC | 8X MIC |
| AECO1156 | 2 | 2.31 | 0.33 | −1.05 | −1.13 | −1.41 | −3.41 |
| (CTX-M-15, | 4 | 3.04 | 2.35 | −1.92 | −2.19 | −2.17 | −4.08 |
| TEM-OSBL) | 6 | 3.46 | 3.28 | −3.57 | −3.51 | −3.73 | −5.69 |
| | 24 | 3.85 | 3.98 | −5.69 | −5.69 | −5.69 | −5.69 |
| AECO1157 | 2 | 2.16 | 1.02 | −0.79 | −0.85 | −1.04 | −3.49 |
| (CTX-M-15, | 4 | 3.17 | 2.88 | −1.39 | −1.70 | −1.89 | −4.98 |
| TEM-OSBL) | 6 | 3.37 | 3.29 | −2.25 | −2.16 | −2.89 | −4.38 |
| | 24 | 3.52 | 3.63 | −5.98 | −5.98 | −5.98 | −5.98 |
| AECO1162 | 2 | 1.93 | −0.36 | −1.30 | −1.23 | −1.31 | −2.91 |
| (CTX-M-14) | 4 | 3.13 | 0.17 | −1.91 | −2.13 | −2.03 | −3.42 |
| | 6 | 3.38 | 2.19 | −3.23 | −3.38 | −3.67 | −4.39 |
| | 24 | 3.46 | 3.46 | −6.08 | −6.08 | −6.08 | −6.08 |
| AECO1166 | 2 | 2.00 | −1.30 | −1.23 | −1.42 | −1.72 | −4.17 |
| (SHV-12) | 4 | 3.08 | 0.58 | −2.26 | −2.38 | −2.55 | −6.08 |
| | 6 | 3.27 | 2.24 | −3.38 | −3.48 | −3.80 | −6.08 |
| | 24 | 3.45 | 3.71 | −6.08 | −6.08 | −6.08 | −6.08 |
| AKPN1159 | 2 | 2.08 | 0.65 | −0.92 | −0.99 | −1.19 | −2.64 |
| (SHV-12) | 4 | 3.02 | 2.37 | −1.87 | −2.02 | −2.17 | −4.16 |
| | 6 | 3.25 | 3.01 | −3.19 | −3.11 | −3.16 | −4.73 |
| | 24 | 3.61 | 3.71 | −5.03 | −5.33 | −6.33 | −6.33 |
| AKPN1162 | 2 | 1.91 | 1.57 | −0.90 | −1.06 | −1.18 | −3.01 |
| (CTX-M-15, | 4 | 2.77 | 2.76 | −1.61 | −1.78 | −2.04 | −3.58 |
| SHV-12) | 6 | 2.88 | 2.96 | −2.70 | −2.87 | −3.10 | −3.66 |
| | 24 | 3.27 | 3.55 | −3.91 | −3.34 | −3.81 | −6.48 |

Abx = antibiotics; AECO = *Escherichia coli*; AKPN = *Klebsiella pneumoniae*; CFU = colony forming units; CLA = clavulanate; CTB = ceftibuten; h = hours; MIC = minimum inhibitory concentration; MEM = meropenem; OSBL = original-spectrum beta-lactamase. Bold indicates ≥ 3 $\log_{10}$ reduction in viable cell density.
[1] The ceftibuten-only concentration equals 4-fold of the MIC concentration for the ceftibuten-clavulanate combination.

Ceftibuten-clavulanate showed time-dependent killing against all strains tested. Increasing the antibiotic concentration (up to 8-fold above the MIC) had little or no effect on the killing kinetics. Bactericidality, defined as ≥3 $\log_{10}$ reduction in viable cell density, was achieved by the 6-hour time point for 4 of 6 strains at all ceftibuten-clavulanate concentrations. The remaining 2 strains achieved ≥2 $\log_{10}$ reduction in viable cells by the 6-hour time point and ≥3 log$_{10}$ reduction by the 24-hour time point for all ceftibuten-clavulanate concentrations. At 8-fold above their respective MICs, the rate of killing for ceftibuten-clavulanate was slower than for meropenem, which achieved ≥3 log$_{10}$ reduction in viable cells by 2 to 4 hours.

Ceftibuten-clavulanate achieved more complete killing against ESBL-producing *E. coli* compared to ESBL-producing *K. pneumoniae*. For *E. coli*, 23 of 24 cultures treated with ceftibuten-clavulanate at 2- to 8-fold above the MIC had viable cell counts at or below the limit of detection after 24 hours of incubation. For *K. pneumoniae*, only 2 of 8 cultures treated with ceftibuten-clavulanate were at or below the limit of detection at 24 hours.

Regrowth was observed in only 1 of 24 ESBL-producing *E. coli* cultures treated with ceftibuten-clavulanate at 2- to 8-fold above the MIC. The single instance of *E. coli* regrowth was observed in a culture of AECO1156 treated with 8-fold the MIC of ceftibuten-clavulanate (data not shown) and was not reproducible. Regrowth was observed in 1 of 8 *K. pneumoniae* cultures treated with ceftibuten-clavulanate. This regrowth occurred in a culture of AKPN1159 treated with 2-fold the MIC of ceftibuten-clavulanate and did not recur in a duplicate experiment.

In summary, the combination of ceftibuten-clavulanate demonstrated time-dependent killing of ESBL-producing *E. coli* and *K. pneumoniae*. All ceftibuten-clavulanate concentrations tested (2- to 8-fold above the MIC) were bactericidal within 6 hours for 4 of 6 strains (3 *E. coli* and 1 *K. pneumoniae*). For the remaining strains (1 *E. coli* and 1 *K. pneumoniae*) ceftibuten-clavulanate was bactericidal within 24 hours. Regrowth of cultures treated with ceftibuten-clavulanate was rarely observed (1 of 24 *E. coli* cultures and 1 of 8 *K. pneumoniae* cultures) and was not reproducible.

Example 4: Determination of MIC$_{90}$ of Ceftibuten and Clavulanate Against Gram-Negative Pathogens A. Enterobacteriaceae Isolates The antimicrobial activity of ceftibuten-clavulanate, ceftibuten alone or clavulanate alone were tested against a total of 385 *Escherichia coli* and 126 *Klebsiella pneumoniae* collected in the USA and Europe during 2014-2015, including isolates displaying an Extended spectrum β-lactamase (ESBL)-phenotype. To assess the ESBL-phenotype, the 511 isolates was tested for the presence of β-lactamases by a microarray based assay (Check-MDR CT 101 Kit; Check-points, The Netherlands) that targets genes encoding CTX-M Groups 1, 2, 8+25 and 9, TEM wild-type (WT) and ESBL, SHV WT and ESBL, ACC, ACT/MIR, CMY-2-like, DHA, FOX, KPC and NDM-1-like. The most common amino acid alterations that expand the spectrum of TEM and SHV enzymes are detected by this assay and these include E104K, R164S/H or G238S for TEM and G238A/S and E240K for SHV. These organisms were collected from urinary tract infections (430 isolates) or bloodstream infections with a source of urinary tract infection (81 isolates).

Table 6a summarizes the results for the β-lactamase screening for 511 Enterobacteriaceae isolates selected for this study. Although 240 isolates tested were positive for only one β-lactamase-encoding gene detected, all other isolates carried multiple β-lactamases.

TABLE 6a

Molecular screening results for isolates

| Check-points test/gene name | Check-points test/gene results (no. of positives [% of total by total no. of organisms]) | | | | |
|---|---|---|---|---|---|
| | Overall (511) | *E. coli* (385) | *K. pneumoniae* (126) | USA (304) | Europe (207) |
| Carbapenemases | | | | | |
| KPC | 25 (4.9%) | 1 (0.3%) | 24 (19.0%) | 16 (5.3%) | 9 (4.3%) |
| NDM-1 | 1 (0.2%) | 0 (0.0%) | 1 (0.8%) | 0 (0.0%) | 1 (0.5%) |
| ESBLs | | | | | |
| CTX-M Group 1 | 294 (57.5%) | 215 (55.8%) | 79 (62.7%) | 151 (49.7%) | 143 (69.1%) |
| CTX-M Group 2 | 2 (0.4%) | 2 (0.5%) | 0 (0.0%) | 1 (0.3%) | 1 (0.5%) |
| CTX-M Group 8 + 25 | 0 (0.0%) | 0 (0.0%) | 0 (0.0%) | 0 (0.0%) | 0 (0.0%) |
| CTX-M Group 9 | 95 (18.6%) | 87 (22.6%) | 8 (6.3%) | 64 (21.1%) | 31 (15.0%) |
| SHV ESBL | 24 (4.7%) | 5 (1.3%) | 19 (15.1%) | 16 (5.3%) | 8 (3.9%) |
| TEM ESBL | 3 (0.6%) | 3 (0.8%) | 0 (0.0%) | 2 (0.7%) | 1 (0.5%) |
| Transferable AmpC | | | | | |
| ACC | 0 (0.0%) | 0 (0.0%) | 0 (0.0%) | 0 (0.0%) | 0 (0.0%) |
| ACT/MIR | 0 (0.0%) | 0 (0.0%) | 0 (0.0%) | 0 (0.0%) | 0 (0.0%) |
| CMYI/MOX | 0 (0.0%) | 0 (0.0%) | 0 (0.0%) | 0 (0.0%) | 0 (0.0%) |
| CMYII | 40 (7.8%) | 39 (10.1%) | 1 (0.8%) | 34 (11.2%) | 6 (2.9%) |
| DHA | 15 (2.9%) | 7 (1.8%) | 8 (6.3%) | 5 (1.6%) | 10 (4.8%) |
| FOX | 2 (0.4%) | 1 (0.3%) | 1 (0.8%) | 2 (0.7%) | 0 (0.0%) |
| Narrow Spectrum β-lactamase | | | | | |
| SHV WT | 124 (24.3%) | 7 (1.8%) | 117 (92.9%) | 44 (14.5%) | 80 (38.6%) |
| TEM WT | 223 (43.6%) | 147 (38.2%) | 76 (60.3%) | 121 (39.8%) | 102 (49.3%) |

MIC values, including $MIC_{50}$ and $MIC_{90}$ values, were determined against all isolates in the presence of the following conditions: ceftibuten alone (range 0.015 to 32 µg/mL); ceftibuten-clavulanate (2:1 ratio; 0.015/0.008 to 32/16 µg/mL); ceftibuten-clavulanate with clavulanate fixed at 2 µg/mL; 0.015/2 to 32/2 µg/mL); ceftibuten-clavulanate with clavulanate fixed at 4 µg/mL (0.015/4 to 32/4 µg/mL), and amoxicillin-clavulanate (2:1 ratio; 0.015/0.008 to 32/16 µg/mL). MIC values were determined using reference frozen-form broth microdilution panels containing cation-adjusted Mueller-Hinton broth per Clinical and Laboratory Standards Institute (CLSI) specifications (CLSI. M07-A10) (CLSI. *Methods for dilution antimicrobial susceptibility tests for bacteria that grow aerobically*; Approved standard-tenth edition. Clinical and Laboratory Standards Institute, Wayne, Pa., 2015). Other antimicrobial agents also were assessed for comparison. Quality Control (QC) strains were tested concomitantly with testing of clinical isolates and inoculum density was monitored by colony counts. QC ranges and interpretive criteria were as available in CLSI (M100-S26) antibiotic susceptibility testing (AST) guidelines (CLSI. *Performance standards for antimicrobial susceptibility testing;* 26th informational supplement. CLSI document M100-S25. Clinical and Laboratory Standards Institute, Wayne, Pa., 2016). Tested QC strains included *Escherichia coli* ATCC 25922 and ATCC 35218, *Klebsiella pneumoniae* ATCC 700603, and *Pseudomonas aeruginosa* ATCC 27853. QC results for comparator agents were within CLSI (M100-S26) published ranges.

The activity of ceftibuten±clavulanate is summarized in Table 6b for the overall collection of 511 Enterobacteriaceae isolates. The activity of ceftibuten±clavulanate compared to other antimicrobial agents is displayed in Table 6c. In Table 6c, the MICs were analyzed using both CLSI (M100-S26, 2016) and EUCAST 2016 (EUCAST: *European Committee on Antimicrobial Susceptibility Testing breakpoint tables for interpretation of MICs and zone diameters*. Version 6.0, 2016) guidelines and classified as resistant (R), intermediate (I) or susceptible (S).

TABLE 6b

Antimicrobial activity of ceftibuten and ceftibuten-clavulanate combinations tested against 511 isolates.

| Organisms/Organism Groups | No. of isolates at MIC (μg/mL, cumulative %) | | | | | | | | | | | | | MIC$_{50}$ | MIC$_{90}$ |
|---|---|---|---|---|---|---|---|---|---|---|---|---|---|---|---|
| | 0.015 | 0.03 | 0.06 | 0.12 | 0.25 | 0.5 | 1 | 2 | 4 | 8 | 16 | 32 | > | | |
| Enterobacteriaceae (511) | | | | | | | | | | | | | | | |
| Ceftibuten | 0 (0.0) | 5 (1.0) | 4 (1.8) | 3 (2.3) | 14 (5.1) | 29 (10.8) | 40 (18.6) | 46 (27.6) | 53 (38.0) | 92 (56.0) | 82 (72.0) | 48 (81.4) | 95 (100.0) | 8 | >32 |
| Ceftibuten-clavulanate at fixed 2 μg/mL | 12 (2.3) | 30 (8.2) | 29 (13.9) | 48 (23.3) | 179 (58.3) | 76 (73.2) | 17 (76.5) | 4 (77.3) | 6 (78.5) | 15 (81.4) | 19 (85.1) | 15 (88.1) | 61 (100.0) | 0.25 | >32 |
| Ceftibuten-clavulanate at fixed 4 μg/mL | 21 (4.1) | 24 (8.8) | 28 (14.3) | 71 (28.2) | 177 (62.8) | 55 (73.6) | 15 (76.5) | 5 (77.5) | 11 (79.6) | 14 (82.4) | 18 (85.9) | 14 (88.6) | 58 (100.0) | 0.25 | >32 |
| Ceftibuten-clavulanate ratio 2:1 | 0 (0.0) | 8 (1.6) | 12 (3.9) | 34 (10.6) | 130 (36.0) | 160 (67.3) | 33 (73.8) | 6 (75.0) | 22 (79.3) | 14 (82.0) | 28 (87.5) | 46 (96.5) | 18 (100.0) | 0.5 | 32 |
| E. coli (385) | | | | | | | | | | | | | | | |
| Ceftibuten | 0 (0.0) | 0 (0.0) | 1 (0.3) | 2 (0.8) | 10 (3.4) | 27 (10.4) | 36 (19.7) | 41 (30.4) | 37 (40.0) | 65 (56.9) | 62 (73.0) | 35 (82.1) | 69 (100.0) | 8 | >32 |
| Ceftibuten-clavulanate at fixed 2 μg/mL | 0 (0.0) | 4 (1.0) | 7 (2.9) | 40 (13.2) | 168 (56.9) | 73 (75.8) | 15 (79.7) | 2 (80.3) | 0 (80.3) | 5 (81.6) | 13 (84.9) | 10 (87.5) | 48 (100.0) | 0.25 | >32 |
| Ceftibuten-clavulanate at fixed 4 μg/mL | 2 (0.5) | 2 (1.0) | 10 (3.6) | 60 (19.2) | 167 (62.6) | 51 (75.8) | 13 (79.2) | 3 (80.0) | 2 (80.5) | 7 (82.3) | 12 (85.5) | 10 (88.1) | 46 (100.0) | 0.25 | >32 |
| Ceftibuten-clavulanate ratio 2:1 | 0 (0.0) | 1 (0.3) | 3 (1.0) | 19 (6.0) | 103 (32.7) | 145 (70.4) | 26 (77.1) | 4 (78.2) | 9 (80.5) | 6 (82.1) | 19 (87.0) | 37 (96.6) | 13 (100.0) | 0.5 | 32 |
| K pneumoniae (126) | | | | | | | | | | | | | | | |
| Ceftibuten | 0 (0.0) | 5 (4.0) | 3 (6.3) | 1 (7.1) | 4 (10.3) | 2 (11.9) | 4 (15.1) | 5 (19.0) | 16 (31.7) | 27 (53.2) | 20 (69.0) | 13 (79.4) | 26 (100.0) | 8 | >32 |
| Ceftibuten-clavulanate at fixed 2 μg/mL | 12 (9.5) | 26 (30.2) | 22 (47.6) | 8 (54.0) | 11 (62.7) | 3 (65.1) | 2 (66.7) | 2 (68.3) | 6 (73.0) | 10 (81.0) | 6 (85.7) | 5 (89.7) | 13 (100.0) | 0.12 | >32 |
| Ceftibuten-clavulanate at fixed 4 μg/mL | 19 (15.1) | 22 (32.5) | 18 (46.8) | 11 (55.6) | 10 (63.5) | 4 (66.7) | 2 (68.3) | 2 (69.8) | 9 (77.0) | 7 (82.5) | 6 (87.3) | 4 (90.5) | 12 (100.0) | 0.12 | >32 |
| Ceftibuten-clavulanate ratio 2:1 | 0 (0.0) | 7 (5.6) | 9 (12.7) | 15 (24.6) | 27 (46.0) | 15 (57.9) | 7 (63.5) | 2 (65.1) | 13 (75.4) | 8 (81.7) | 9 (88.9) | 9 (96.0) | 5 (100.0) | 0.5 | 32 |
| All CTX-M-producing isolates (365) | | | | | | | | | | | | | | | |
| Ceftibuten | 0 (0.0) | 1 (0.3) | 1 (0.5) | 2 (1.1) | 9 (3.6) | 23 (9.9) | 36 (19.7) | 40 (30.7) | 45 (43.0) | 78 (64.4) | 61 (81.1) | 33 (90.1) | 36 (100.0) | 8 | 32 |
| Ceftibuten-clavulanate at fixed 2 μg/mL | 7 (1.9) | 25 (8.8) | 23 (15.1) | 43 (26.8) | 169 (73.2) | 70 (92.3) | 14 (96.2) | 3 (97.0) | 0 (97.0) | 2 (97.5) | 0 (97.5) | 2 (98.1) | 7 (100.0) | 0.25 | 0.5 |
| Ceftibuten-clavulanate at fixed 4 μg/mL | 16 (4.4) | 19 (9.6) | 22 (15.6) | 63 (32.9) | 168 (78.9) | 50 (92.6) | 12 (95.9) | 3 (96.7) | 3 (97.5) | 1 (97.8) | 0 (97.8) | 2 (98.4) | 6 (100.0) | 0.25 | 0.5 |
| Ceftibuten-clavulanate ratio 2:1 | 0 (0.0) | 2 (0.5) | 7 (2.5) | 29 (10.4) | 119 (43.0) | 152 (84.7) | 30 (92.9) | 5 (94.2) | 12 (97.5) | 1 (97.8) | 3 (98.6) | 2 (99.2) | 3 (100.0) | 0.5 | 1 |
| All CTX-M-producing E. coli (294) | | | | | | | | | | | | | | | |
| Ceftibuten | 0 (0.0) | 0 (0.0) | 0 (0.0) | 1 (0.3) | 7 (2.7) | 23 (10.5) | 34 (22.1) | 36 (34.4) | 33 (45.6) | 61 (66.3) | 49 (83.0) | 26 (91.8) | 24 (100.0) | 8 | 32 |
| Ceftibuten-clavulanate at fixed 2 μg/mL | 0 (0.0) | 2 (0.7) | 6 (2.7) | 35 (14.6) | 161 (69.4) | 68 (92.5) | 14 (97.3) | 2 (98.0) | 0 (98.0) | 1 (98.3) | 0 (98.3) | 2 (99.0) | 3 (100.0) | 0.25 | 0.5 |
| Ceftibuten-clavulanate at fixed 4 μg/mL | 2 (0.7) | 0 (0.7) | 9 (3.7) | 52 (21.4) | 161 (76.2) | 48 (92.5) | 12 (96.6) | 3 (97.6) | 1 (98.0) | 1 (98.3) | 0 (98.3) | 2 (99.0) | 3 (100.0) | 0.25 | 0.5 |

TABLE 6b-continued

Antimicrobial activity of ceftibuten and ceftibuten-clavulanate combinations tested against 511 isolates.

| Organisms/Organism Groups | No. of isolates at MIC (μg/mL; cumulative %) | | | | | | | | | | | | | MIC$_{50}$ | MIC$_{90}$ |
|---|---|---|---|---|---|---|---|---|---|---|---|---|---|---|---|
| | 0.015 | 0.03 | 0.06 | 0.12 | 0.25 | 0.5 | 1 | 2 | 4 | 8 | 16 | 32 | > | | |
| Ceftibuten-clavulanate ratio 2:1 ratio | 0 (0.0) | | 2 (0.7) | 17 (6.5) | 95 (38.8) | 139 (86.1) | 23 (93.9) | 4 (95.2) | 9 (98.3) | 0 (98.3) | 1 (98.6) | 2 (99.3) | 2 (100.0) | 0.5 | 1 |
| **All CTX-M-producing *K pneumoniae* (71)** | | | | | | | | | | | | | | | |
| Ceftibuten | | 1 (1.4) | 1 (2.8) | 1 (4.2) | 2 (7.0) | 0 (7.0) | 2 (9.9) | 4 (15.5) | 12 (32.4) | 17 (56.3) | 12 (73.2) | 7 (83.1) | 12 (100.0) | 8 | >32 |
| Ceftibuten-clavulanate at fixed 2 μg/mL | 7 (9.9) | 23 (42.3) | 17 (66.2) | 8 (77.5) | 8 (88.7) | 2 (91.5) | 0 (91.5) | 1 (93.0) | 0 (93.0) | 1 (94.4) | 0 (94.4) | 0 (94.4) | 4 (100.0) | 0.06 | 0.5 |
| Ceftibuten-clavulanate at fixed 4 μg/mL | 14 (19.7) | 19 (46.5) | 13 (64.8) | 11 (80.3) | 7 (90.1) | 2 (93.0) | 0 (93.0) | 0 (93.0) | 2 (95.8) | 0 (95.8) | 0 (95.8) | 0 (95.8) | 3 (100.0) | 0.06 | 0.25 |
| Ceftibuten-clavulanate ratio 2:1 ratio | 0 (0.0) | 2 (2.8) | 5 (9.9) | 12 (26.8) | 24 (60.6) | 13 (78.9) | 7 (88.7) | 1 (90.1) | 3 (94.4) | 1 (95.8) | 2 (98.6) | 0 (98.6) | 1 (100.0) | 0.25 | 2 |
| Isolates producing CTX-M Group 1 (276) | | | | | | | | | | | | | | | |
| Ceftibuten | 5 (1.8) | 23 (10.1) | 22 (18.1) | 32 (29.7) | 5 (3.6) | 5 (3.6) | 15 (9.1) | 17 (15.2) | 36 (28.3) | 76 (55.8) | 58 (76.8) | 30 (87.7) | 34 (100.0) | 8 | >32 |
| Ceftibuten-clavulanate at fixed 2 μg/mL | | | 22 (18.8) | 0 (0.0) | 121 (73.6) | 49 (91.3) | 12 (95.7) | 3 (96.7) | 0 (96.7) | 2 (97.5) | 0 (97.5) | 2 (98.2) | 5 (100.0) | 0.25 | 0.5 |
| Ceftibuten-clavulanate at fixed 4 μg/mL | 13 (4.7) | 17 (10.9) | | 44 (34.8) | 126 (80.4) | 32 (92.0) | 9 (95.3) | 3 (96.4) | 3 (97.5) | 1 (97.8) | 0 (97.8) | 2 (98.6) | 4 (100.0) | 0.25 | 0.5 |
| Ceftibuten-clavulanate ratio 2:1 ratio | | 0 (0.0) | 7 (2.5) | 21 (10.1) | 87 (41.7) | 115 (83.3) | 25 (92.4) | 3 (93.5) | 11 (97.5) | 1 (97.8) | 3 (98.9) | 2 (99.6) | 1 (100.0) | 0.5 | 1 |
| Isolates producing CTX-M Group 9 (92) | | | | | | | | | | | | | | | |
| Ceftibuten | 0 (0.0) | 1 (1.1) | 1 (2.2) | 2 (4.3) | 4 (8.7) | 18 (28.3) | 20 (50.0) | 24 (76.1) | 10 (87.0) | 2 (89.1) | 3 (92.4) | 3 (95.7) | 4 (100.0) | 1 | 16 |
| Ceftibuten-clavulanate at fixed 2 μg/mL | 2 (2.2) | 2 (4.3) | 1 (5.4) | 10 (16.3) | 51 (71.7) | 22 (95.7) | 2 (97.8) | 1 (98.9) | 0 (98.9) | 0 (98.9) | 0 (98.9) | 0 (98.9) | 1 (100.0) | 0.25 | 0.5 |
| Ceftibuten-clavulanate at fixed 4 μg/mL | 3 (3.3) | 2 (5.4) | 0 (5.4) | 18 (25.0) | 45 (73.9) | 19 (94.6) | 3 (97.8) | 1 (98.9) | 0 (98.9) | 0 (98.9) | 0 (98.9) | 0 (98.9) | 1 (100.0) | 0.25 | 0.5 |
| Ceftibuten-clavulanate ratio 2:1 ratio | 0 (0.0) | 2 (2.2) | 0 (2.2) | 8 (10.9) | 31 (44.6) | 40 (88.0) | 6 (94.6) | 2 (96.7) | 2 (98.9) | 0 (98.9) | 0 (98.9) | 0 (98.9) | 1 (100.0) | 0.5 | 1 |
| Isolates producing SHV ESBL (18) | | | | | | | | | | | | | | | |
| Ceftibuten | 0 (0.0) | 2 (11.1) | 1 (16.7) | 1 (22.2) | 1 (27.8) | 2 (38.9) | 3 (55.6) | 1 (61.1) | 1 (66.7) | 1 (72.2) | 4 (94.4) | 0 (94.4) | 1 (100.0) | 1 | 16 |
| Ceftibuten-clavulanate at fixed 2 μg/mL | 5 (27.8) | 2 (38.9) | 5 (66.7) | 2 (77.8) | 3 (94.4) | 1 (100.0) | | | | | | | | 0.06 | 0.25 |
| Ceftibuten-clavulanate at fixed 4 μg/mL | 5 (27.8) | 2 (38.9) | 4 (61.1) | 4 (83.3) | 3 (100.0) | | | | | | | | | 0.06 | 0.25 |
| Ceftibuten-clavulanate ratio 2:1 ratio | 0 (0.0) | 6 (33.3) | 1 (38.9) | 3 (55.6) | 3 (72.2) | 5 (100.0) | | | | | | | | 0.12 | 0.5 |

TABLE 6b-continued

Antimicrobial activity of ceftibuten and ceftibuten-clavulanate combinations tested against 511 isolates.

| Organisms/ Organism Groups | No. of isolates at MIC (μg/mL; cumulative %) | | | | | | | | | | | | | $MIC_{50}$ | $MIC_{90}$ |
|---|---|---|---|---|---|---|---|---|---|---|---|---|---|---|---|
| | 0.015 | 0.03 | 0.06 | 0.12 | 0.25 | 0.5 | 1 | 2 | 4 | 8 | 16 | 32 | > | | |
| KPC-producers (25) | | | | | | | | | | | | | | | |
| Ceftibuten | 0 (0.0) | 1 (4.0) | 0 (4.0) | 0 (4.0) | 0 (4.0) | 1 (8.0) | 0 (8.0) | 1 (12.0) | 3 (24.0) | 7 (52.0) | 6 (76.0) | 5 (96.0) | 1 (100.0) | 8 | 32 |
| Ceftibuten-clavulanate at fixed 2 μg/mL | | 0 (0.0) | 1 (4.0) | 0 (4.0) | 1 (8.0) | 0 (8.0) | 2 (16.0) | 1 (20.0) | 6 (44.0) | 7 (72.0) | 4 (88.0) | 3 (100.0) | | 8 | 32 |
| Ceftibuten-clavulanate at fixed 4 μg/mL | 0 (0.0) | 1 (4.0) | 0 (4.0) | 1 (8.0) | 0 (8.0) | 0 (8.0) | 2 (16.0) | 2 (24.0) | 5 (44.0) | 6 (68.0) | 4 (84.0) | 4 (100.0) | | 8 | 32 |
| Ceftibuten-clavulanate ratio 2:1 | | 0 (0.0) | 1 (4.0) | 0 (4.0) | 0 (4.0) | 1 (8.0) | 0 (8.0) | 1 (12.0) | 9 (48.0) | 5 (68.0) | 5 (88.0) | 3 (100.0) | | 8 | 32 |
| Isolates producing transferable AmpC (57) | | | | | | | | | | | | | | | |
| Ceftibuten | 0 (0.0) | 0 (0.0) | 1 (1.8) | 0 (1.8) | 0 (1.8) | 0 (1.8) | 0 (1.8) | 1 (3.5) | 2 (7.0) | 3 (12.3) | 1 (14.0) | 0 (14.0) | 49 (100.0) | >32 | >32 |
| Ceftibuten-clavulanate at fixed 2 μg/mL | | 2 (3.5) | 0 (3.5) | 1 (5.3) | 1 (7.0) | 1 (8.8) | 0 (8.8) | 0 (8.8) | 0 (8.8) | 1 (10.5) | 2 (14.0) | 0 (14.0) | 49 (100.0) | >32 | >32 |
| Ceftibuten-clavulanate at fixed 4 μg/mL | 0 (0.0) | 2 (3.5) | 0 (3.5) | 1 (5.3) | 2 (8.8) | 0 (8.8) | 0 (8.8) | 0 (8.8) | 1 (10.5) | 1 (12.3) | 1 (14.0) | 1 (15.8) | 48 (100.0) | >32 | >32 |
| Ceftibuten-clavulanate ratio 2:1 | | 0 (0.0) | 1 (1.8) | 1 (3.5) | 2 (7.0) | 0 (7.0) | 1 (8.8) | 0 (8.8) | 1 (10.5) | 1 (12.3) | 2 (15.8) | 33 (73.7) | 15 (100.0) | 32 | >32 |

TABLE 6c

Activity of ceftibuten, ceftibuten-clavulanate combinations and comparator antimicrobial agents tested against 511 isolates.

| Antimicrobial Agent | MIC$_{50}$ | MIC$_{90}$ | Range | CLSI[a] % S | % I | % R | EUCAST[a] % S | % I | % R |
|---|---|---|---|---|---|---|---|---|---|
| Ceftibuten | 8 | >32 | 0.03->32 | 56.0 | 16.0 | 28.0 | 18.6 | — | 81.4 |
| Ceftibuten-clavulanate at fixed 2 µg/mL | 0.25 | >32 | ≤0.015->32 | — | — | — | — | — | — |
| Ceftibuten-clavulanate at fixed 4 µg/mL | 0.25 | >32 | ≤0.015->32 | — | — | — | — | — | — |
| Ceftibuten-clavulanate 2:1 ratio | 0.5 | 32 | 0.03->32 | — | — | — | — | — | — |
| Amoxicillin-clavulanate | 16 | 32 | 1->32 | 35.2 | 32.1 | 32.7 | 35.2 | — | 64.8 |
| Piperacillin-tazobactam | 4 | >64 | ≤0.5->64 | 77.1 | 7.4 | 15.5 | 68.3 | 8.8 | 22.9 |
| Mecillinam | 2 | >32 | 0.12->32 | — | — | — | — | — | — |
| Ceftriaxone | >8 | >8 | 0.12->8 | 5.9 | 1.2 | 93.0 | 5.9 | 1.2 | 93.0 |
| Ceftazidime | 16 | >32 | 0.12->32 | 24.7 | 12.5 | 62.8 | 8.4 | 16.2 | 75.3 |
| Cefepime | >16 | >16 | ≤0.5->16 | 22.2 | 14.7 | 63.1[b] | 18.4 | 10.0 | 71.6 |
| Aztreonam | >16 | >16 | 0.25->16 | 17.2 | 10.2 | 72.6 | 3.3 | 13.9 | 82.8 |
| Imipenem | ≤0.12 | 0.5 | ≤0.12->8 | 93.3 | 0.6 | 6.1 | 93.9 | 2.7 | 3.3 |
| Meropenem | 0.03 | 0.12 | ≤0.015->32 | 92.2 | 0.8 | 7.0 | 93.0 | 3.3 | 3.7 |
| Nitrofurantoin | 16 | 256 | 2->256 | 74.8 | 8.8 | 16.4 | 83.6 | — | 16.4 |
| Ciprofloxacin | >4 | >4 | ≤0.03->4 | 21.5 | 2.5 | 75.9 | 20.5 | 1.0 | 78.5 |

[a]Criteria as published by CLSI [2016] and European Committee on Antimicrobial Susceptibility Testing (EUCAST) [2016]
[b]Intermediate interpreted as susceptible-dose dependent As shown in Tables 6b and 6c, ceftibuten alone (MIC$_{50/90}$, 8/>32 µg/mL) displayed limited activity against this collection of 511 Enterobacteriaceae isolates, and elevated MIC values were also observed for other cephalosporins and/or aztreonam against the collection. Ceftibuten inhibited only 56.0% and 18.6% of the isolates applying the CLSI and EUCAST breakpoints, respectively. In contrast, ceftibuten-clavulanate combinations displayed MIC$_{50}$ values that were 16- to 32-fold lower when compared to ceftibuten alone against all 511 isolates. Ceftibuten-clavulanate inhibited 76.5 and 81.4% of the isolates at ≤1 and ≤8 µg/mL when tested using fixed 2 µg/mL clavulanate, and 76.5 and 82.4% of the isolates at the same concentrations when clavulanate was tested at fixed 4 µg/mL. When testing ceftibuten-clavulanate at the 2:1 ratio, 73.8 and 82.0% of the isolates were inhibited at ≤1 and ≤8 µg/mL (CLSI and EUCAST breakpoints for ceftibuten alone used for comparison purposes).

The activity of ceftibuten-clavulanate combinations was limited against isolates producing KPC (25 isolates; MIC$_{50/90}$=8/32 µg/mL for all inhibitor concentrations) and transferrable AmpCs (57 isolates; MIC$_{50/90}$=≥32/>32 µg/mL for all inhibitor concentrations).

Ceftibuten-clavulanate combinations were very active against 365 isolates producing CTX-M enzymes (the most common beta-lactamase genes detected among the isolates tested). This set excluded isolates carrying genes encoding a transferrable AmpC and/or carbapenemases. MIC$_{50/90}$ values were 0.25/0.5, 0.25/0.5 and 0.5/1 µg/mL for fixed 2 µg/mL, fixed 4 µg/mL, and 2:1 ratio, respectively, and these combinations inhibited 92.9 to 96.2% of the isolates at ≤1 µg/mL and 97.5 to 97.8% of the isolates at ≤8 µg/mL. Ceftibuten alone (MIC$_{50/90}$, 8/32 µg/mL) had limited activity, inhibiting only 19.7% of isolates at ≤1 µg/mL and 64.4% at ≤8 µg/mL. Ceftibuten-clavulanate combinations also inhibited all 18 isolates carrying SHV ESBL enzymes (without a carbapenemase and transferable AmpC) at ≤0.5 µg/mL, regardless of the concentration of inhibitor. Overall, ceftibuten-clavulanate combinations (MIC$_{50}$ and MIC$_{90}$ ranges, 0.25-0.5 and 0.5-1 µg/mL) were active against a total of 387 isolates with confirmed ESBL enzymes and with no carbapenemases or transferable AmpC enzymes.

Figure 2:
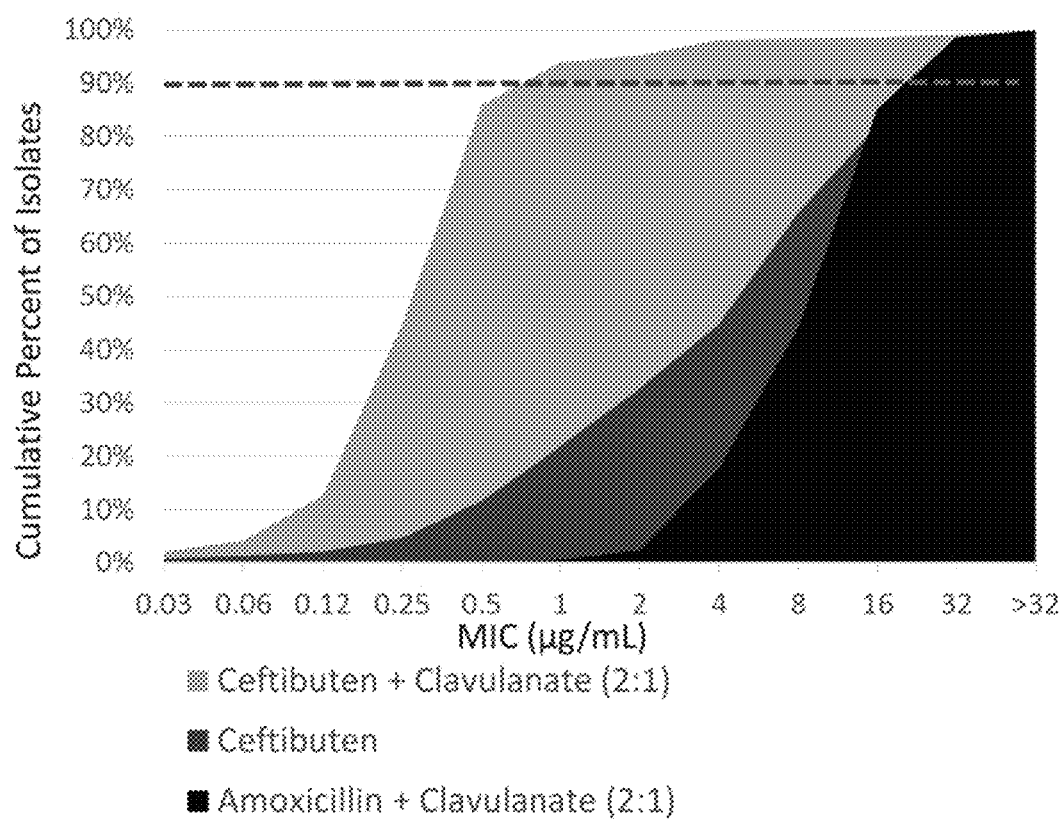
FIG. 2 shows the percent of isolates from a panel of 379 *E. coli* or *K. pneumoniae* isolates genotyped for CTX-M, TEM, or SHV ESBLs that are inhibited by ceftibuten alone, ceftibuten:clavulanate at a 2:1 ratio, and amoxicillin:clavulanate at a 2:1 ratio at each concentration.

For treatment with ceftibuten alone or ceftibuten+clavulanate at a 2:1 ratio, the MIC was measured for each of the 379 E. coli or K. pneumoniae isolates genotyped for CTX-M, TEM, or SHV ESBLS. The percent of these isolates inhibited at each MIC is shown in FIG. 2. The MIC$_{90}$ for ceftibuten:clavulanate, ceftibuten, and ammoxicillin:clavulanate are about 1, 32, and 16 µg/mL, respectively.

Twenty-three isolates demonstrating negative results for the screened β-lactamase genes displayed MIC values≥8 µg/mL for at least one of the ceftibuten-clavulanate combinations. All these isolates were E. coli from 21 hospitals located in six countries. Preliminary data from whole genome sequencing of these isolates indicated the presence of an inducible chromosomal AmpC.

Overall, the presence of clavulanate at a fixed 2 or 4 µg/mL or tested in a 2:1 ratio decreased ceftibuten MIC values for Enterobacteriaceae isolates collected from UTI or bloodstream infection associated to UTIs. This effect was noted regardless of the geographic region or bacterial species. Ceftibuten-clavulanate combinations displayed very good activity against isolates producing ESBLs (CTX-M and SHV ESBL enzymes) and the activity of these β-lactam/inhibitor combinations was at least 16-fold higher when compared to ceftibuten alone. Ceftibuten with and without clavulanate displayed limited activity against isolates carrying genes encoding carbapenemases and/or transferable AmpC enzymes.

B. MIC Evaluation of A/B Gram-Negative Biothreat Pathogens

The in vitro potency of ceftibuten and ceftibuten-clavulanate (2:1 ratio) against model strains of four category A/B Gram-negative biothreat pathogens was evaluated using standard MIC assay protocols. The strains were Yersinia pestis Colorado92, Francisella tularensis ShuS4, Burkholderia mallei China7, and Burkholderia pseudomallei 1026b. The MICs determined for both ceftibuten and ceftibuten-clavulanate were 0.03, 0.25, 1-2, and 8 µg/mL, respectively. The finding that the MICs of ceftibuten and the combination were substantially identical may be because these strains do not carry ESBL enzymes.

Example 5: Determining Feasibility of Cephalosporin Administration Based on MIC and Pharmacokinetics To determine feasibility for oral administration, MIC data was analyzed in the context of the pharmacokinetic properties of cephalosporins. The pharmacokinetic and pharmacodynamics (PK/PD) index is the free drug concentration in human plasma that exceeds the MIC for 40% of the total dosing interval (Clin Infect Dis 1998; 26:1-10), and is typically written as 40% fT>MIC.

The PK/PD index and target magnitude associated with the efficacy of cephalosporins against members of the Enterobacteriaceae family are well described in the literature for certain cephalosporins (see e.g. Table 7). Existing data show that cefditoren has suboptimal pharmacokinetic properties relative to other drugs in the class, specifically: a low bioavailability (14% for cefditoren (Spectracef® Package Insert. Purdue Pharmaceutical Products, Stamford, Conn.: 2005), compared to approximately 40-90% for ceftibuten, cefpodoxime and cefixime), a low maximum concentration (Cmax), a relatively short half-life, and a low free fraction (see Package Insert References in Table 7 and Pharmacotherapy 1997; 17:707-720). The $MIC_{90}$ for cefditoren in several series of Enterobacteriaceae isolates that do not produce ESBLs (ESBL$^-$) is reported to be 0.5 µg/mL (BMC Infect Dis 2012; 12:228 and Diagn Microbiol Infect Dis 2010; 67:251-260). Pharmacokinetic data for cefditoren shows that peak free drug concentrations rarely exceed 0.3 µg/mL (Table 7) with approved doses, and the half-life is under two hours. Therefore, even if higher doses of cefditoren are given more frequently (Rev Esp Quimioter 2007; 20:51-60), together with an ESBL-inhibitor, and despite MICs ranging from 0.12-2 µg/mL against ESBL+ isolates (See Table 3), it is unlikely that cefditoren would achieve systemic exposures that exceed 40% fT>MIC for ESBL-producing Enterobacteriaceae.

Whether the PK/PD target of 40% fT>MIC was achievable for contemporary ESBL-producing (ESBL$^+$) Enterobacteriaceae with any of the other cephalosporins in combination with an existing β-lactamase inhibitor was not known. In addition, it was not previously known which of the cephalosporins would show superior activity against contemporary ESBL-producing Enterobacteriaceae, either alone or in combination with a β-lactamase inhibitor.

Example 2 demonstrated that a combination of ceftibuten and clavulanate, tested at a 2:1 ratio, was able to achieve MICs≤2 µg/mL against a representative panel of Enterobacteriaceae that produce contemporary ESBLs.

In contrast, the combination of cefixime+clavulanate achieved an MIC=4 µg/mL for at least one non-AmpC expressing isolate in the panel, and cefpodoxime+clavulanate achieved an MIC=4 µg/mL for four non-AmpC expressing isolates in the panel. Thus, when combined with clavulanate, cefixime would likely need to achieve 40% fT>2 or 4 µg/mL, and cefpodoxime would likely need to achieve 40% fT>4 µg/mL. To evaluate if the PK/PD targets were feasible, the MIC data was evaluated in the context of the pharmacokinetic properties of cephalosporins set forth in Table 7.

The free maximum concentration (fCmax) following a single 400 mg oral dose of cefixime is 1.3 µg/mL, indicating that higher doses of cefixime, given multiple times a day, would be required to reliably achieve and maintain plasma concentrations>2 µg/mL. This is extremely challenging to achieve with feasible doses given that doses>400 mg of cefixime are associated with non-proportional increases in Cmax (Pediatr Infect Dis J 1987; 6:963-970). An oral dose of 2 g of cefixime would only achieve a fCmax of 2.7 µg/mL and would be unlikely to achieve 40% fT>MIC even if administered three times daily. Furthermore, these published pharmacokinetic data indicate that it would not be possible to achieve a fCmax>4 µg/mL with feasible oral doses of cefixime.

When cefpodoxime is dosed orally at 400 mg (a dose exceeding the approved regimen for uncomplicated urinary tract infection of 100 mg every 12 hours (Vantin® Package Insert. Pharmacia and Upjohn Company, New York, N.Y.: 2013)) the fCmax is approximately 3.1 µg/mL, i.e. under the likely target of 4 µg/mL. When 800 mg of cefpodoxime is given orally, a fCmax of approximately 5.4 µg/mL is achieved (J Antimicrob Chemother 1990; 26:e21-e28), but concentrations would decline to <4 µg/mL within one half-life (2.9 h at this dose). This indicates that doses of 800 mg would need to be given at least four times a day to achieve 40% fT>MIC, i.e. an unfeasible total daily dose of ≥2.4 g.

TABLE 7

Pharmacokinetic Parameters for Third-Generation Orally-Bioavailable Cephalosporins

|  | Ceftibuten[1] | Cefpodoxime[2] | Cefixime[3] | Cefditoren[4] |
|---|---|---|---|---|
| Protein binding (% bound) | 65 (plasma) | 22-33 (serum); 21-29 (plasma) | 65 (serum) | 88 (plasma) |
| Mean $C_{max}$ (µg/mL) with associated dose | 15  400 mg | 1.4  100 mg<br>2.3  200 mg<br>3.9  400 mg | 2  200 mg<br>3.7  400 mg | 1.8  200 mg |
| Mean $fC_{max}$ (µg/mL) with associated dose | 5.3  400 mg | 1.1  100 mg<br>1.8  200 mg<br>3.1  400 mg | 0.7  200 mg<br>1.3  400 mg | 0.22  200 mg |
| Mean unbound plasma concentration following one elimination half-life$^a$ (µg/mL) | 2.6 | 1.55 (400 mg) | 0.65 (400 mg) | 0.11 |
| Elimination half-life (h) | 2.4 | 2.1-2.8 | 3-4$^b$ | 1.6 |

$C_{max}$ maximum total drug concentration in plasma; $fC_{max}$ free/unbound maximum drug concentration in plasma |
[1] Cedax® Package Insert. Shionogi USA, Florham Park, NJ: 2009.
[2] Vantin® Package Insert. Pharmacia and Upjohn Company, New York, NY: 2013.
[3] Suprax® Package Insert. Lupin, Baltimore, MD: 2016.
[4] Spectracef® Package Insert. Purdue Pharmaceutical Products, Stamford, CT: 2005.
$^a$For highest plasma concentration from previous row;
$^b$May range up to 9 hours in some normal volunteers.

Figure 3:
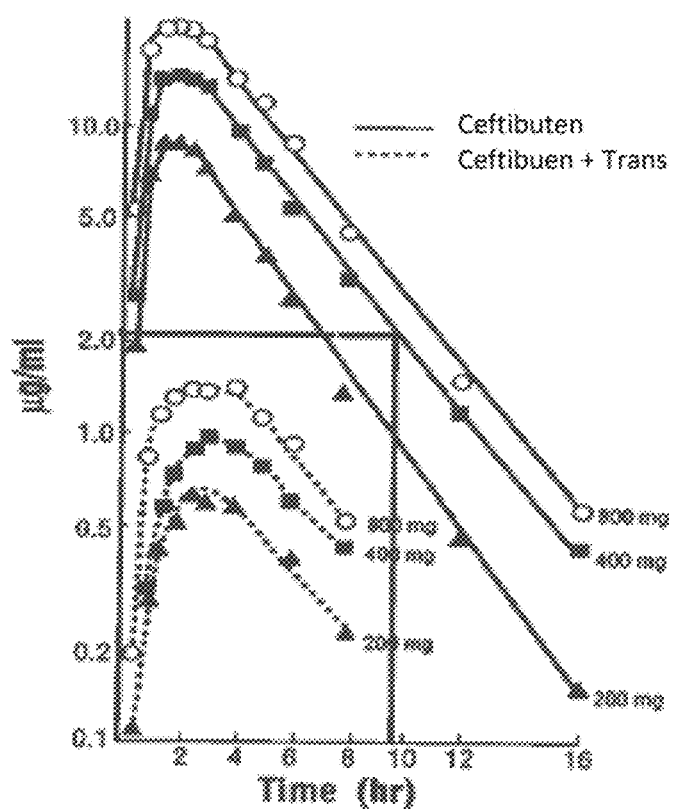
FIG. 3 illustrates the mean plasma concentration-time curves of ceftibuten and metabolite ceftibuten-trans in healthy male subjects following oral administration of single oral doses of 200, 400, and 800 mg of ceftibuten (n=12 healthy volunteers per dose level) (Antimicrob Agents Chemother 1995; 39:359-361).

In contrast, a 400 mg oral dose of ceftibuten achieves free drug concentrations of >2 µg/mL for at least 6 hours following drug administration. See Table 8 (adapted from Cedax® Package Insert. Shionogi USA, Florham Park, N.J.: 2009) and FIG. 3 (adapted from Lin et al. (1995) Antimicrobial Agents and Chemotherapy, 39:359-361). These data support 40% fT>MIC of 2 µg/mL with as few as two, or a maximum of three, daily doses of ceftibuten.

TABLE 8

Average Plasma Concentration (Total and Free) of Ceftibuten after a Single 400 mg Dose in a Cohort of 12 Healthy Male Volunteers[1]

| Time (h) | Total Drug Concentration (µg/mL) | Free Drug Concentration (µg/mL) |
|---|---|---|
| 1 | 6.1 | 2.14 |
| 1.5 | 9.9 | 3.47 |
| 2 | 11.3 | 3.96 |
| 3 | 13.3 | 4.66 |
| 4 | 11.2 | 3.92 |
| 6 | 5.8 | 2.03 |
| 8 | 3.2 | 1.12 |
| 12 | 1.1 | 0.39 |

[1]Cedax® Package Insert. Shionogi USA, Florham Park, NJ: 2009.

Importantly, while the pharmacokinetic data are published for these cephalosporins (Table 7), without understanding the MICs of the combination of these cephalosporins with clavulanate for contemporary ESBL-producing isolates, it would not have been obvious that only ceftibuten was likely to achieve 40% fT>MIC with a feasible dosing regimen.

Example 6: Determining Post-β-Lactamase Inhibitor Effect of Clavulanate+Ceftibuten Administration The post-β-Lactamase Inhibitor Effect (PBLIE) of the β-lactamase inhibitor clavulanate in combination with various β-lactams, either ceftibuten or other cephalosporins, was assessed. Certain β-lactamase inhibitors are known to have a Post-β-Lactamase Inhibitor Effect (PBLIE), wherein the inhibitor continues to assert an effect despite no longer being present. The PBLIE can vary widely for different β-lactams and β-lactamases, and for different pathogen isolates expressing different types and amounts of β-lactamases (Antimicrob Agents Chemother 1996; 40:2796-2801, J Antimicrob Chemother 2004; 53:616-619, Antimicrob Agents Chemother 2014; 58:2434-2437). While a PBLIE has been previously defined for cephalosporins+β-lactam inhibitors, such as sulbactam, tazobactam and avibactam (J Antimicrob Chemother 2004; 53:616-619, Antimicrob Agents Chemother 2014; 58:2434-2437, Lett Appl Microbiol 2016: doi: 10.1111/lam.12592), no-one has reported a PBLIE for a cephalosporin, such as ceftibuten, in combination with clavulanate. Therefore, it was unknown whether a PBLIE would be present for clavulanate when used in combination with ceftibuten against a contemporary common ESBL-producing isolate, such as an *E. coli* isolate expressing CTX-M-15 (AECO1078).

A. PBLIE for Ceftibuten with Clavulanate in *E. coli* Expressing CTX-M-15

To assess PBLIE, the isolate *E. coli* AECO1078 was grown with no antibiotic (abx), 2 µg/mL ceftibuten (CTB), or 2 µg/mL ceftibuten (CTB) and 1 µg/mL clavulanate (CLA). After 1 hour, the cells were washed and then diluted 1,000-fold into media containing no antibiotic (abx), CTB only, or CTB and CLA. The CFU/mL counts of samples spread on agar plates were measured at 1 hour time points, including pre- and post-wash at the 1 hour time point.

Figure 4A:
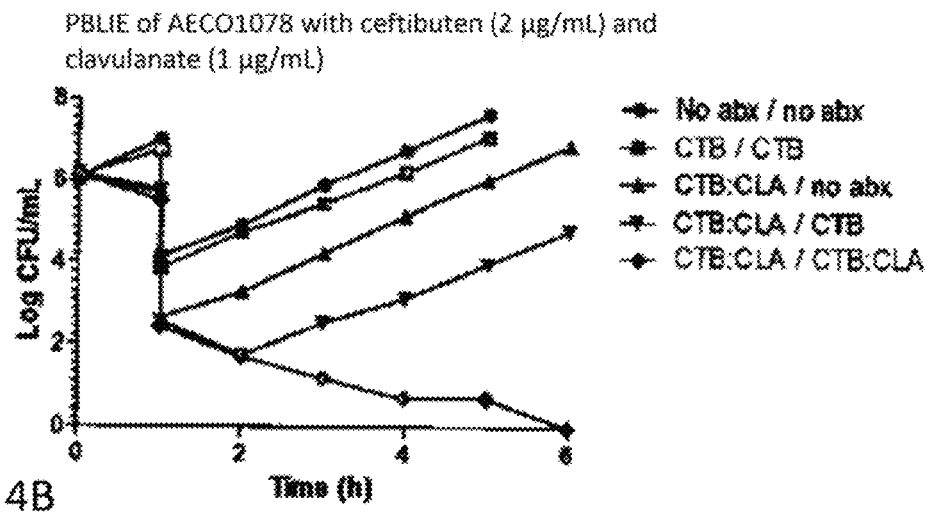
FIG. 4A-C illustrate the post-β-lactamase inhibitor effect (PBLIE) for ceftibuten+clavulanate (FIG. 4A), cefixime+clavulanate (FIG. 4B), and cefpodoxime+clavulanate (FIG. 4C) against the *Escherichia coli* isolate AECO1078, which has an MIC=32 µg/mL for ceftibuten alone and 1 µg/mL for ceftibuten+clavulanate (2:1). Plotted on the line graph are the change in the bacterial growth, illustrated as colony forming units (CFU) per mL on a log ordinate axis, against time on the abscissa. At one hour, the media were changed and replaced with fresh media. Four treatment groups are illustrated, with the contents of the media before/after the change at one hour illustrated in the legend. Abbreviations: abx, antibiotics; CTB, ceftibuten; CLA, clavulanate; CFM, cefixime; CPD, cefpodoxime.

The bactericidal activity under the tested conditions is shown in FIG. 4A. The results confirm the in vitro MIC data from Example 2, whereby the MIC for AECO1078 against ceftibuten alone was determined to be 32 µg/mL, and against ceftibuten+clavulanate (2:1) was 1 µg/mL, See Table 2a-b. Ceftibuten alone had a minimal effect on the in vitro growth of AECO1078 (compare the line with squares (ceftibuten alone pre- and post-wash) to the line with circles (no antibiotics pre- and post-wash) on FIG. 4A). The combination of clavulanate with ceftibuten resulted in rapid bactericidal activity (compare the line with diamonds (ceftibuten+clavulanate pre- and post-wash) to the line with circles (no antibiotics pre- and post-wash) on FIG. 4A).

Furthermore, clavulanate demonstrated a sustained PBLIE of 2.5 hours when used with ceftibuten against a contemporary CTX-M-15-producing *E. coli* isolate (compare the line with down-pointing triangles (ceftibuten+clavulanate pre-wash, ceftibuten only post-wash) to the line with circles (no antibiotics pre- and post-wash) on FIG. 4A). Not only was regrowth delayed, but bacterial kill continued for approximately one hour after clavulanate was removed and ceftibuten remained (compare the 1 and 2-hour timepoints on the line with down-pointing triangles (ceftibuten+clavulanate pre-wash, ceftibuten only post-wash), FIG. 4A).

PBLIE is the additional time needed to increase growth 1 $\log_{10}$ for a culture that was treated with the combination then recovered in media containing only the beta-lactam compared to a culture that was exposed to only the beta-lactam during both the treatment and recovery periods. PBLIE is distinct from the post-antibiotic effect (PAE). PAE is the additional time needed for a culture that was treated with an antibiotic to increase 1 $\log_{10}$ compared to an untreated control culture. As shown in FIG. 4A, the PBLIE was clearly differentiated from the post-antibiotic effect (PAE; persistent inhibition of bacterial growth after antimicrobial exposure has ceased) (compare the line with down-pointing triangles (ceftibuten+clavulanate pre-wash, ceftibuten only post-wash) to the line with up-pointing triangles (ceftibuten+clavulanate pre-wash, no antibiotics post wash) on FIG. 4A). The PAE was only about 0.10 hours (compare the line with squares (ceftibuten alone pre- and post-wash) to the line with up-pointing triangles (ceftibuten+clavulanate pre-wash, no antibiotics post wash) on FIG. 4A). There was no sustained bacterial kill after the removal of the ceftibuten+clavulanate.

B. PBLIE for Various Cephalosporins and Isolates

To determine whether the PBLIE seen with the combination of ceftibuten and clavulanate was applicable to other cephalosporins and to other isolates, the PBLIEs for cefixime+clavulanate, cefpodoxime+clavulanate, and ceftibuten+clavulanate were evaluated for *E. coli* expressing CTX-M-15 (AECO1078), *E. coli* expressing CTX-M-15 and TEM-OBSL (AECO1157), and *K. pneumoniae* expressing SHV-12 (AKPN1159). The PBLIE was assayed as described above with the mass ratio of cephalosporin:clavulanate constant at 2:1 and the concentration of cephalosporin listed in Table 9.

TABLE 9

PBLIE and PAE of Cephalosporin + Clavulanate for Different ESBL Isolates

| Cephalosporin | Cefpodoxime | | | Cefixime | | | Ceftibuten | | |
|---|---|---|---|---|---|---|---|---|---|
| Strain | AECO1078 | AECO1157 | AKPN1159 | AECO1078 | AECO1157 | AKPN1159 | AECO1078 | AECO1157 | AKPN1159 |
| PBLIE (h) | −0.5 | 0 | 0 | 0.8 | 2.2 | 1.0 | 2.5 | 3.9 | 1.8 |
| PAE (h) | −0.5 | 0.1 | −0.2 | 0.5 | 1.2 | 0.6 | 0.2 | 0.9 | 0.2 |
| [Cephalosporin] (μg/mL) | 2 | 4 | 1 | 2 | 2 | 0.5 | 2 | 1 | 0.12 |

AECO1078: CTX-M-15 *E. coli*; AECO1157: CTX-M-15 + TEM-OBSL *E. coli*; AKPN1159: SHV-12 *K. pneumoniae*

The duration of PBLIE and PAE for each condition is summarized in Table 9. For each strain tested, the clavulanate-induced PBLIE was longest for ceftibuten. The clavulanate-induced PBLIE was substantially shorter for cefixime, and cefpodoxime demonstrated no measurable clavulanate-induced PBLIE.

The large differences in PBLIE were surprising, because in Example 2, cefixime+clavulanate and cefpodoxime+clavulanate demonstrated a large reduction in MIC for almost all isolates tested (See Table 2a-b). Furthermore, cefixime+clavulanate had the second lowest MICs (after ceftibuten) of all cephalosporins tested for nearly all isolates (See Table 3). This demonstrates that the large reductions in MIC when combining a beta-lactamase inhibitor and a cephalosporin and PBLIE are not necessarily correlated.

Figure 4B:
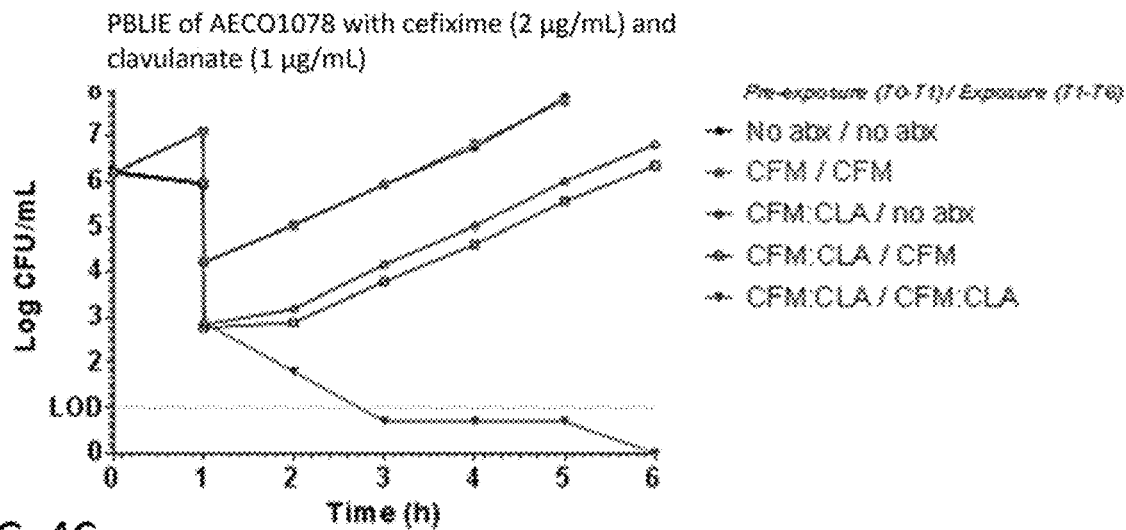
Figure 4C:
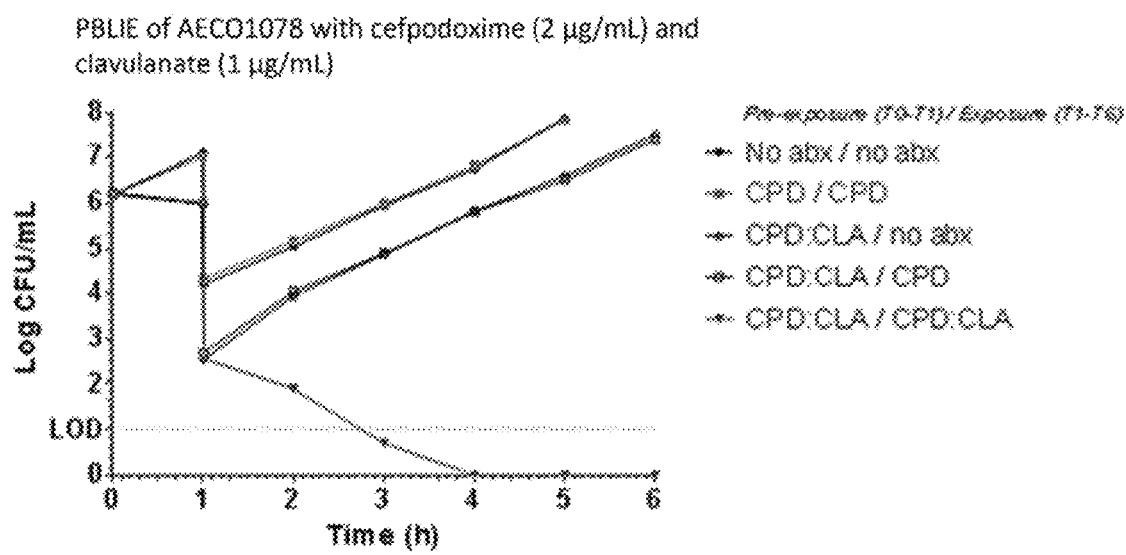

Representative PBLIE results for clavulanate in combination with alternative cephalosporins for *E. coli* expressing CTX-M-15 (AECO1078) are summarized in FIG. 4B (cefixime) and FIG. 4C (cefpodoxime). As shown in FIG. 4B, similar to the results described in the previous section for clavulanate with ceftibuten, the combination of clavulanate with cefixime resulted in rapid bactericidal activity (compare the line for cefixime+clavulanate to the line for no antibiotics on FIG. 4B). However, unlike the ceftibuten-clavulanate combination, clavulanate did not demonstrate a sustained PBLIE when used with cefixime against this CTX-M-15-producing *E. coli* isolate. Regrowth was only minimally delayed and the CFU/mL counts did not decrease after clavulanate was removed and cefixime remained (compare the 1 and 2-hour timepoints on the line for cefixime+clavulanate pre-wash, cefixime only post-wash, FIG. 4B). Similarly, as shown in FIG. 4C, the combination of cefpodoxime and clavulanate had no measurable PBLIE (Table 9, FIG. 4C).

Figure 5A:
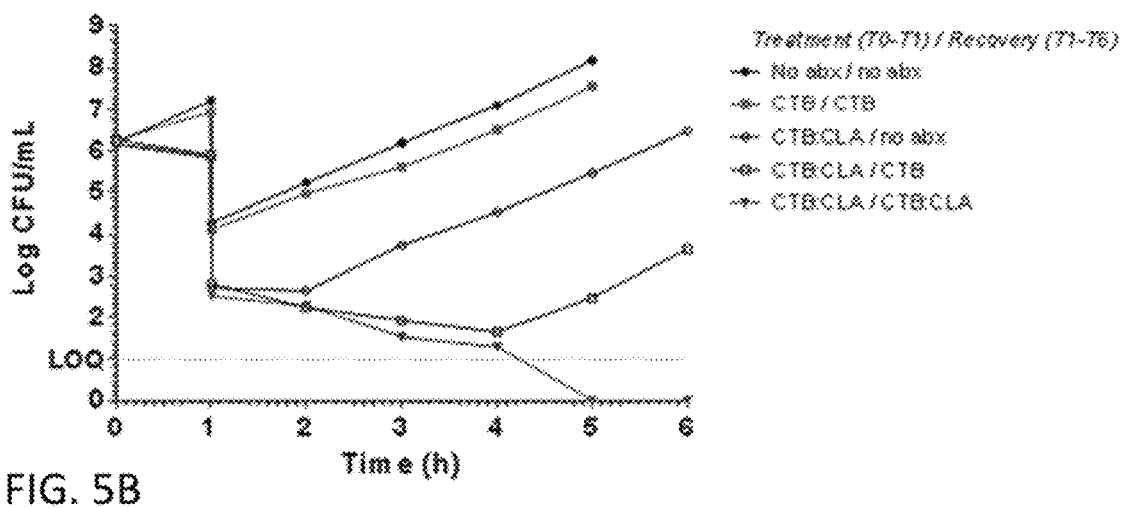
FIG. 5A-C illustrate the post-β-lactamase inhibitor effect (PBLIE) for ceftibuten+clavulanate (FIG. 5A), cefixime+clavulanate (FIG. 5B), and cefpodoxime+clavulanate (FIG. 5C) against the *Escherichia coli* isolate AECO1157. Plotted on the line graph are the change in the bacterial growth, illustrated as colony forming units (CFU) per mL on a log ordinate axis, against time on the abscissa. At one hour, the media were changed and replaced with fresh media. Four treatment groups are illustrated, with the contents of the media before/after the change at one hour illustrated in the legend. Abbreviations: abx, antibiotics; CTB, ceftibuten; CLA, clavulanate; CFM, cefixime; CPD, cefpodoxime.
Figure 5B:
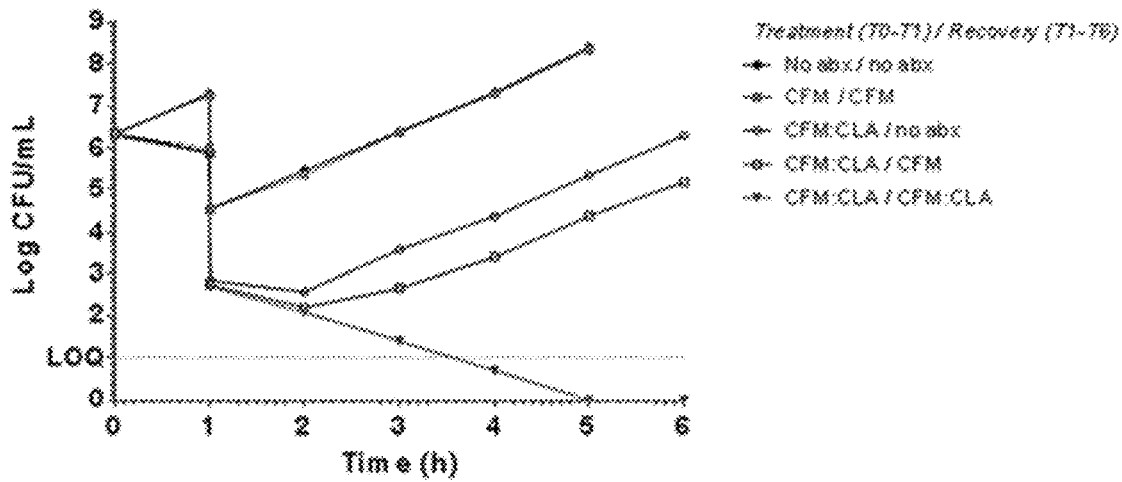
Figure 5C:
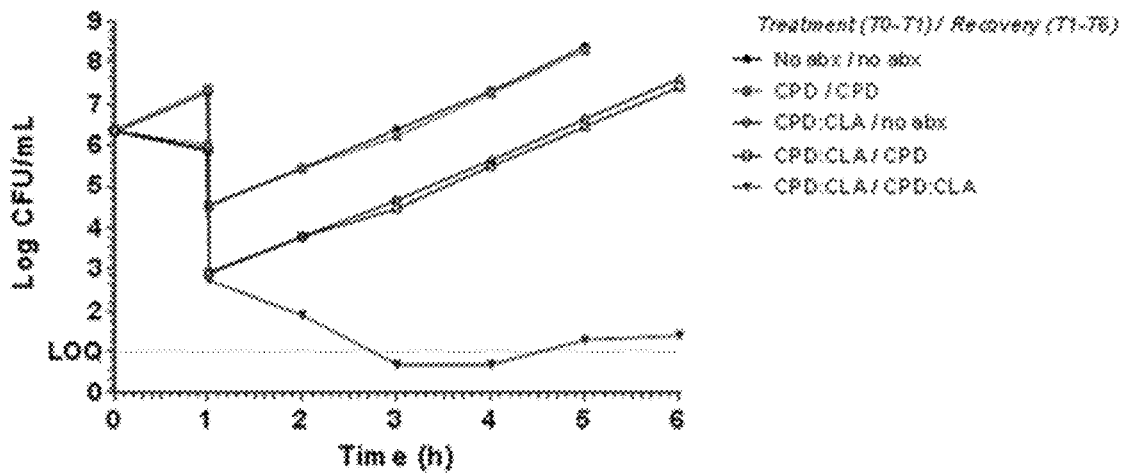

Representative PBLIE results for clavulanate in combination with alternative cephalosporins for an *E. coli* isolate expressing CTX-M-15 and TEM-OBSL (AECO1157) are summarized in FIG. 5A (clavulanate+/−ceftibuten), FIG. 5B (clavulanate+/−cefixime) and FIG. 5C (clavulanate+/−cefpodoxime). As shown in FIG. 5A, despite the minimal effect ceftibuten alone had, ceftibuten alone after removal of clavulanate continued to decrease the CFU/mL counts for at least 3 hours. For the same ESBL-producing Enterobacteriaceae, cefixime+clavulanate (FIG. 5B) and cefpodoxime+clavulanate (FIG. 5C) had significantly shorter or no PBLIE, respectively.

Figure 6A:
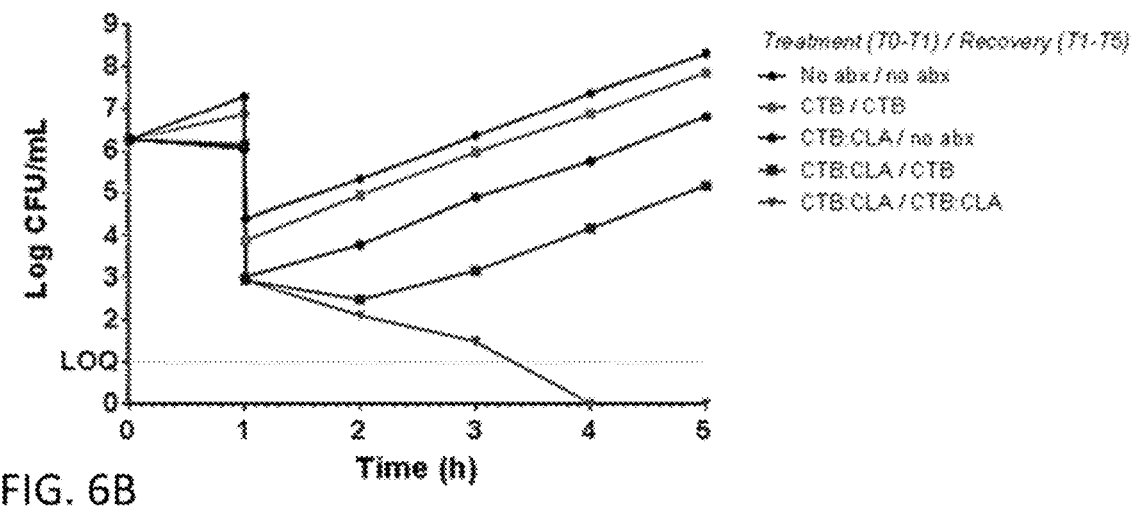
FIG. 6A-C illustrate the post-β-lactamase inhibitor effect (PBLIE) for ceftibuten+clavulanate (FIG. 6A), cefixime+clavulanate (FIG. 6B), and cefpodoxime+clavulanate (FIG. 6C) against the *Escherichia coli* isolate AKPN1159. Plotted on the line graph are the change in the bacterial growth, illustrated as colony forming units (CFU) per mL on a log ordinate axis, against time on the abscissa. At one hour, the media were changed and replaced with fresh media. Four treatment groups are illustrated, with the contents of the media before/after the change at one hour illustrated in the legend. Abbreviations: abx, antibiotics; CTB, ceftibuten; CLA, clavulanate; CFM, cefixime; CPD, cefpodoxime.
Figure 6B:
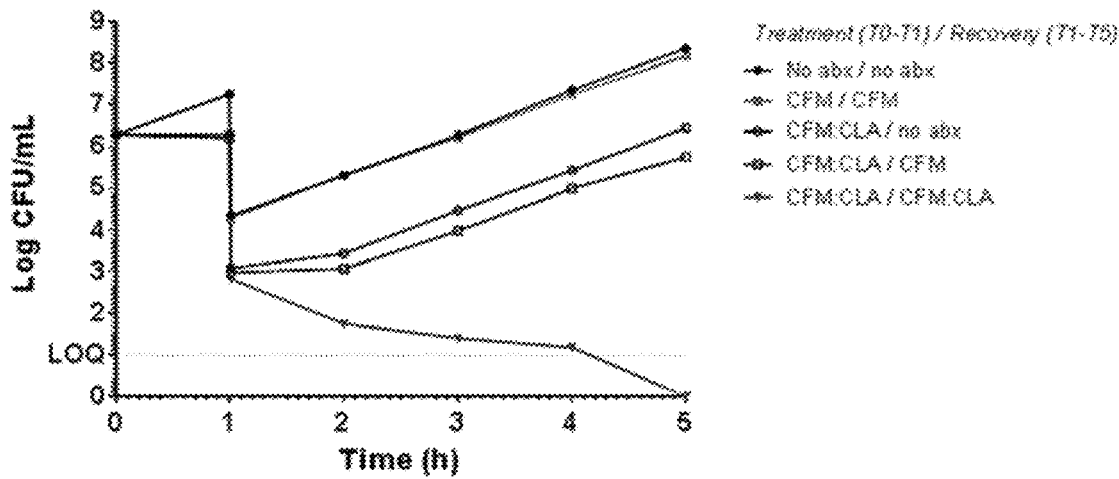
Figure 6C:
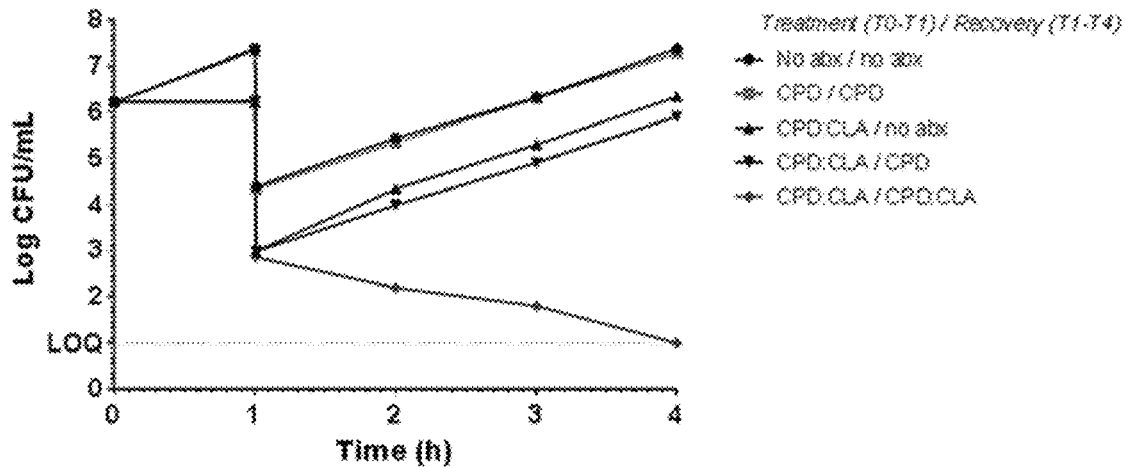

Representative PBLIE results for clavulanate in combination with alternative cephalosporins for a *K. pneumoniae* expressing SHV-12 (AKPN1159) are set forth in FIG. 6A (clavulanate+/−ceftibuten), FIG. 6B (clavulanate+/−cefixime) and FIG. 6C (clavulanate+/−cefpodoxime). As shown, the observed PBLIE effect following treatment of AKPN1159 showed similar effects to those described above for tested *E. coli* isolates.

C. Dosing Regimens

The above data support feasible dosing regimens of ceftibuten+clavulanate to effectively treat infections due to ESBL-producing Enterobacteriaceae. As discussed in Example 5, the pharmacokinetics of ceftibuten show that administration of ceftibuten alone is likely to exceed the PK/PD targets for efficacy at feasible human doses given two to three times daily allowing bacteria to be exposed to a sufficient concentration of ceftibuten throughout the dosing interval. However, the plasma half-life of clavulanate is shorter than that of ceftibuten (approximately 1 versus 2.4 h) (Excerpta Medica, International Congress Series 544; 1980, pages 117-121. Cedax® Package Insert. Shionogi USA, Florham Park, N.J.: 2009). Therefore, the pathogens will initially be exposed to high concentrations of both compounds, but the clavulanate concentration will fall below the PK/PD threshold concentration (desired amount) earlier than ceftibuten. If clavulanate is able to contribute to the inhibition of bacterial growth after its concentration drops below the target threshold as shown from the PBLIE results above, the combination of ceftibuten+clavulanate is more likely to demonstrate clinical efficacy. Such data may also be factored into the justification for the human dose regimen.

The observed MICs for ceftibuten+clavulanate support PK/PD target attainment against contemporary ESBL-producing Enterobacteriaceae. Using data from the MIC experiment and the pharmacokinetic analysis, potential human dosing ranges for ceftibuten and clavulanate in the final combination product were determined. The total daily dose of ceftibuten was determined to be in the range of 800 to 1800 mg (in two to three divided doses), and the total daily dose of clavulanate was determined to be in the range of 250 to 750 mg (in two to three divided doses), generating a ratio of ceftibuten:clavulanate of 1:1 to 7:1.

The observed MICs for cefixime+clavulanate and cefpodoxime+clavulanate do not support PK/PD target attainment based on the above described analysis of the known systemic exposures achieved by these cephalosporins relative to PK/PD targets required for efficacy.

Example 7: Pharmacodynamics and Dosing of Ceftibuten and Clavulanate

A. Assessment of Free Drug Concentration Above MIC Using Chemostat Model

1. Ceftibuten

A one-compartment in vitro chemostat infection model was used to determine whether for ceftibuten the amount of time (expressed as a percentage of the dosing interval) that free drug concentrations are above the MIC (% fT>MIC) correlates with CFU reduction. In addition, this model was also used to determine the magnitude of exposure of ceftibuten associated with stasis, 1-log, or 2-log reduction in bacterial growth.

a. Method

A 300 ml glass chemostat model was filled with Cation-Adjusted Mueller Hinton II Broth (CAMHB) (20 to 25 mg/L calcium, 10 to 12.5 mg/L magnesium; Becton, Dickinson and Company, Sparks, Md.) and placed in a water bath at 35° C. Magnetic stirrers were used for consistent mixing of the contents during the experiment. The chemostat model was inoculated with $10^6$ CFU/mL of the bacteria.

Once inoculated, the bacteria were allowed to enter log phase growth over 30 minutes before adding antibiotic exposures. For each drug exposure/bacteria combination, the experiment was conducted over 24 hours and consisted of a drug free control and two experimental (i.e., drug containing) replicate models. Data from the two replicate models were treated as independent exposures given there is some expected variability in obtained concentrations due to small inconsistencies in volume flows between the chemostat models.

A peristaltic pump (Masterflex L/S model 7524-40; Cole-Parmer, Vernon Hills, Ill.) was set to infuse CAMHB into the models at a desired elimination rate for the drug. Broth samples were collected from the model throughout the experiment to determine free drug concentrations and bacterial density. Antibiotic carryover was minimized by serial dilution of samples. Bacterial density was counted after 18-24 hours incubation at 37° C. The lower limit of detection of bacterial density was 1.7 $\log_{10}$ CFU/ml. Time-kill curves were constructed by plotting the $\log_{10}$ CFU/mL against time.

To test ceftibuten alone, E. coli (ATCC 25922) was used. Exposure targeting 10, 20, 40, 60, 80, and 100% fT>MIC over 24 hours was calculated and dosed into the chemostat model. The dosing was carried out to target a ceftibuten peak of 10 μg/mL, which is contemplated to simulate clinically achievable maximum ceftibuten concentrations in humans. The control models served to define 0% fT>MIC results. The bacterial density was assessed at 0, 1, 6, 12, and 24 hours. Drug concentrations were assessed at the peak and trough of each administered dose to achieve the desired exposure and at least one other midpoint concentration for each interval. This resulted in no less than 3 available ceftibuten concentrations in each dosing interval to calculate fT>MIC. The change in $\log_{10}$ CFU/ml at 24 hours was the primary endpoint for exposure response relationship. The magnitude of fT>MIC required for stasis, 1-log and 2-log reductions were estimated after fitting the data with an inhibitory sigmoidal Emax model in Phoenix WinNonlin (Pharsight Corp. Mountain View, Calif.).

b. Results

Figure 7A:
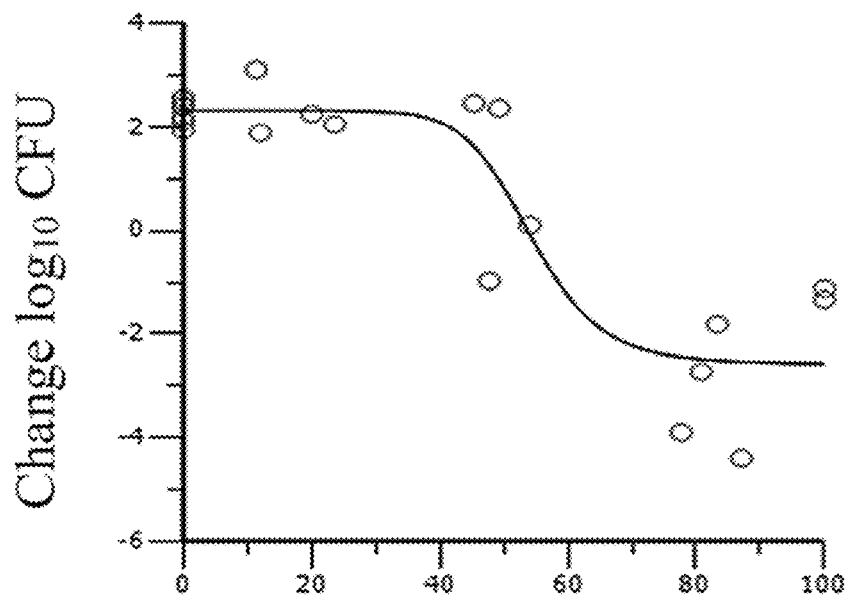
FIG. 7A shows $E_{max}$ exposure response model for fT>MIC (0.25 µg/mL) of ceftibuten against an *E. coli* ATCC 25922 in a chemostat model.

As shown in FIG. 7A, the % fT>MIC was associated with CFU reduction, confirming that % fT>MIC may be a PD driver for ceftibuten. The fT>MIC to achieve stasis, 1-log or 2-log CFU reductions are shown in Table 10, which demonstrate that approximately 50% to 60% fT>MIC was associated with net bacterial stasis to 1-log kill effects. These results are consistent with data for the cephalosporin class of antibiotics indicating that the amount of time that % fT>MIC is a PD driver for efficacy, with 40% fT>MIC associated with stasis and 60% to 70% associated with maximum bacterial killing (Craig W A, *Clin. Infect. Dis.* (1998) 26:1-10)

TABLE 10 fT > MIC exposure for ceftibuten associated with CFU reductions

| PD Target | fT > MIC |
|---|---|
| Stasis | 53.7 |
| 1-log CFU reduction | 58.5 |
| 2-log CFU reduction | 66.0 |

2 Ceftibuten+Clavulanate a. Methods

Using the in vitro chemostat model described above, dose fractionation studies of clavulanate were performed in the presence of fixed ceftibuten exposure at 50% to 60% fT>MIC against a CTX-M-55-producing E. coli strain. This isolate had a ceftibuten MIC of >64 μg/mL, clavulanate MIC>32 μg/mL, and ceftibuten+clavulanate MIC of 1 μg/mL. In vitro model infusion rates were fixed to achieve ceftibuten exposures of about 60% fT>MIC at a MIC of 1 μg/mL, with a ceftibuten peak of 10 μg/mL and each ceftibuten dose administered every 8 hours. Clavulanate was added to the models every 24, 12, or 6 hours to achieve a range of free maximum concentration (fCmax), free area under the curve (fAUC$_{0-24}$), and percent of time free concentration remain above a threshold (% fT>threshold) exposures.

Experiments with the ceftibuten alone served as the zero exposure for the clavulanate. Bacterial density was collected at 0, 1, 6, 12, 18 and 24 hours for each experiment and both ceftibuten and clavulanate concentrations were confirmed with no fewer than 3 sampling points during each interval. For each cryovial used for PK sample collection, 30 μl of tazobactam was pre-filled to prevent post-collection degradation of ceftibuten. A precise volume of 300 μl of analyte (ceftibuten and clavulanate) containing broth were obtained from the chemostat model and mixed with the tazobactam before freezing at −80° C. The change in $\log_{10}$ CFU/ml at 24 hours was plotted against PD exposures and analyzed using an inhibitory sigmoidal Emax model in Phoenix WinNonlin. The following PD exposure relationships were assessed: fCmax, fAUC$_{0-24}$, fCmax/threshold, fAUC$_{0-24}$/threshold, and % fT>threshold, where the threshold applied for separation of the PD index was equal to the isolate ceftibuten+clavulanate MIC. The final PD index was selected based on $R^2$, AIC, and visual inspection of plots.

Once a PD index for clavulanate was determined, varied clavulanate exposures were combined with the fixed ceftibuten exposure that provided ~1-log CFU reduction against the ceftibuten+clavulanate MIC of 4 beta-lactamase producing Enterobacteriaceae (ESBL phenotypes shown in Table 11). Experiments with ceftibuten alone served as the zero exposure for clavulanate. Ceftibuten peaks were targeted at 10 μg/ml. Bacterial density was again collected at 0, 1, 6, 12, 18 and 24 hours for each experiment and both ceftibuten and clavulanate concentrations were confirmed with no fewer than 3 sampling points during each interval. For each cryovial used for PK sample collection, 30 μl of avibactam was pre-filled to prevent post-collection degradation of ceftibuten. A precise volume of 300 μl of analyte (ceftibuten and clavulanate) containing broth were obtained from the chemostat model and mixed with the avibactam before freezing at −80° C.

The change in $\log_{10}$ CFU/ml at 24 hours was plotted against the PD index and analyzed using an inhibitory sigmoidal Emax model in Phoenix WinNonlin. For each isolate, exposures that resulted in stasis, 1-log, and 2-log CFU reductions were calculated. Thresholds were varied in 1-2 dilutions above and below the ceftibuten+clavulanate MIC of each isolate. The final PD index was selected based on $R^2$, AIC, and visual inspection of plots.

b. Results

Figure 7B:
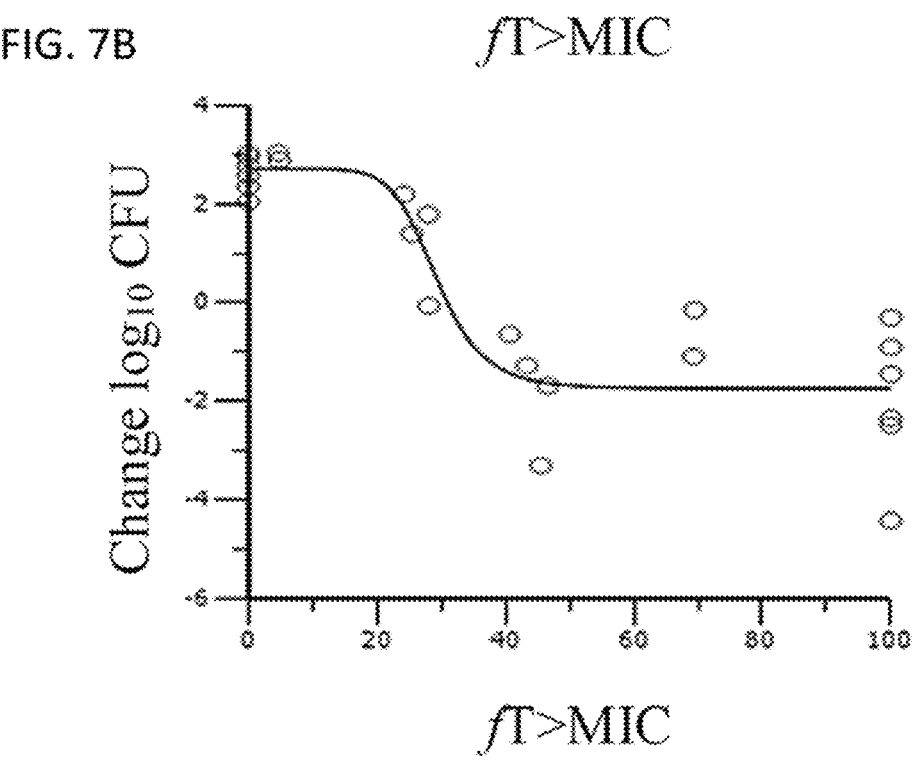
FIG. 7B shows Emax exposure response model for fT>MIC (1 µg/mL) of ceftibuten+clavulanate against an *E. coli* clinical isolate in a chemostat model.

As shown in FIG. 7B and Table 11, approximately 30% to 40% clavulanate fT>$C_T$ for a $C_T$ of 0.25 to 1 μg/mL achieved net bacterial stasis in combination with ceftibuten. Further, the results support that the amount of time that free drug concentrations are above a threshold concentration (fT>$C_T$) is a factor associated with PD for clavulanate (FIG. 7B).

Consistent with the PBLIE findings above against ESBL-producing Enterobacteriaceae, the duration of clavulanate exposures (30% to 40% fT>CT) do not need to match the full duration of ceftibuten exposures (50% fT>MIC) to afford protection against β-lactamases.

TABLE 11

Inter-isolate Comparative Summary Pharmacodynamic Fits Along with Stasis and 1-log CFU Reduction Exposure Requirements by Clavulanate Threshold

| Organism | CTB + CLAV MIC | CTB MIC | ESBLs | fT > threshold | Stasis | 1-Log Reduction |
|---|---|---|---|---|---|---|
| E. coli | 1/0.5 | >64 | CTX-M-55 | fT > 2 | 24.9 | 27.7 |
| | | | | fT > 1 | 31.0 | 35.9 |
| | | | | fT > 0.5 | 36.3 | 41.0 |
| | | | | fT > 0.25 | 42.4 | 47.9 |
| | | | | fT > 0.125 | 48.6 | 54.9 |
| E. coli | 0.5/0.25 | >64 | CTX-M-15, TEM-OSBL | fT > 1 | 8.1 | 21.5 |
| | | | | fT > 0.5 | 22.7 | 44.0 |
| | | | | fT > 0.25 | 32.0 | 54.4 |
| | | | | fT > 0.125 | 40.2 | 63.7 |
| K. pneumoniae | 0.25/0.125 | >64 | CTX-M-15, SHV-12 | fT > 1 | 23.5 | N/A |
| | | | | fT > 0.5 | 66.1 | 85.7 |
| | | | | fT > 0.25 | 74.6 | 91.0 |
| | | | | fT > 0.125 | 80.2 | 96.7 |
| | | | | fT > 0.06 | 85.0 | 100.0 |
| K. pneumoniae | 0.25/0.125 | 16 | CTX-M-14, SHV-12 | fT > 1 | 5.0 | N/A |
| | | | | fT > 0.5 | 19.4 | 30.9 |
| | | | | fT > 0.25 | 29.4 | 47.7 |
| | | | | fT > 0.125 | 39.4 | 66.0 |
| | | | | fT > 0.06 | 49.9 | 84.4 |

Note:
CTB = ceftibuten, CLAV = clavulanate, N/A = data not available. MIC = Minimum Inhibitory Concentration, ESBL = Extended Spectrum β-lactamase B. Pharmacokinetic Modeling for Ceftibuten and Clavulanate PK models for ceftibuten and clavulanate were constructed by digitizing existing PK data from the literature to serve as the modeling dataset. A one-compartment PK model with first-order elimination for ceftibuten and a two-compartment PK model with first-order elimination for clavulanate were developed. The relationship between clearance (CL) and creatine clearance (CLcr) was determined for both ceftibuten and clavulanate and was applied as a continuous covariate in the respective PK models. Monte Carlo simulations were performed to estimate the likelihood of jointly achieving the PD targets associated with efficacy (i.e., ceftibuten exposures of ≥50% fT>MIC and clavulanate exposures of ≥30% to 40% fT>CT for a threshold concentration ($C_T$) of 0.25 to 1 μg/mL) determined above across a range of dosing regimens (ceftibuten 300 or 400 mg TID in combination with clavulanate 125 or 187.5 mg TID) (Tables 12-15) in patients with normal renal function using uniform distribution across CLcr of 85 to 145 mL/min. 1000 simulations were performed and the probability of target attainment was assessed for each of the scenarios.

Using the PK/PD targets for cephalosporins and clavulanate and the ceftibuten PK data, an exemplary human dose that would likely be effective against Enterobacteriaceae with a MIC≤2 μg/mL for ceftibuten was determined. The analysis indicated that ceftibuten could achieve this efficacy target at an exemplary total daily dose of 900 to 1200 mg, such as given as 300-400 mg TID when given in combination with clavulanate (e.g. to protect ceftibuten from degradation by target β-lactamase) at an exemplary total daily dose of 375 to 562.5 mg, such as given as 125-187.5 mg TID. Results from this work demonstrated that there were a variety of target scenarios that achieved >90% probability of target attainment (PTA) (Tables 12-15).

TABLE 12

Percentage of cases where free-drug plasma concentrations exceed MIC and $C_T$ in normal renal function (CrCL: > 80 mL/min) following ceftibuten (400 mg, TID) clavulanic acid (125 mg, TID) administration.

| Ceft MIC \| Clav $C_T$ | % Time above MIC or $C_T$ | | | | | | | |
|---|---|---|---|---|---|---|---|---|
| | 50 \| 20 | 60 \| 20 | 50 \| 30 | 60 \| 30 | 50 \| 40 | 60 \| 40 | 50 \| 50 | 60 \| 50 |
| 1 \| 0.125 | 100 | 99.5 | 100 | 99.5 | 100 | 99.5 | 98 | 97.5 |
| 2 \| 0.125 | 96.6 | 79.8 | 96.6 | 79.8 | 96.6 | 79.8 | 94.6 | 78.3 |
| 1 \| 0.25 | 100 | 99.5 | 100 | 99.5 | 97.9 | 97.4 | 77.3 | 77 |
| 2 \| 0.25 | 96.6 | 79.8 | 96.6 | 79.8 | 94.5 | 78.2 | 74.4 | 60.7 |
| 1 \| 0.5 | 100 | 99.5 | 97.6 | 97.1 | 67.2 | 66.9 | 29.3 | 29.3 |
| 2 \| 0.5 | 96.6 | 79.8 | 94.2 | 77.9 | 64.5 | 52.4 | 28.2 | 22.4 |
| 1 \| 1 | 91.2 | 90.7 | 39.5 | 39.3 | 9.3 | 9.3 | 2.3 | 2.3 |
| 2 \| 1 | 87.8 | 72.4 | 37.7 | 30.9 | 8.9 | 7.1 | 2.3 | 2.1 |

Ceft = ceftibuten; Clav = clavulanic acid; CrCL = creatinine clearance; MIC = minimum inhibitory concentration; $C_T$ = threshold concentration; TID = three times per day.

TABLE 13

Percentage of cases where free-drug plasma concentrations exceed MIC and $C_T$ in normal renal function (CrCL: > 80 mL/min) following ceftibuten (400 mg, TID) clavulanic acid (187.5 mg, TID) administration

| Ceft MIC \| Clav $C_T$ | % Time above MIC or $C_T$ | | | | | | | |
|---|---|---|---|---|---|---|---|---|
| | 50 \| 20 | 60 \| 20 | 50 \| 30 | 60 \| 30 | 50 \| 40 | 60 \| 40 | 50 \| 50 | 60 \| 50 |
| 1 \| 0.125 | 100 | 99.6 | 100 | 99.6 | 100 | 99.6 | 100 | 99.6 |
| 2 \| 0.125 | 97.5 | 79.9 | 97.5 | 79.9 | 97.5 | 79.9 | 97.5 | 79.9 |
| 1 \| 0.25 | 100 | 99.6 | 100 | 99.6 | 100 | 99.6 | 94.2 | 93.8 |
| 2 \| 0.25 | 97.5 | 79.9 | 97.5 | 79.9 | 97.5 | 79.9 | 91.8 | 75.5 |
| 1 \| 0.5 | 100 | 99.6 | 100 | 99.6 | 91.4 | 91 | 54.9 | 54.7 |
| 2 \| 0.5 | 97.5 | 79.9 | 97.5 | 79.9 | 89.1 | 73.4 | 53.3 | 44.1 |
| 1 \| 1 | 100 | 99.6 | 85.4 | 85.1 | 36.5 | 36.5 | 13.4 | 13.4 |
| 2 \| 1 | 97.5 | 79.9 | 83.6 | 68.4 | 35.5 | 29.1 | 13.2 | 10.8 |

Ceft = ceftibuten; Clav = clavulanic acid; CrCL = creatinine clearance; MIC = minimum inhibitory concentration; $C_T$ = threshold concentration; TID = three times per day.

TABLE 14

Percentage of cases where free-drug plasma concentrations exceed MIC and $C_T$ in normal renal function (CrCL: > 80 mL/min) following ceftibuten (300 mg, TID) clavulanic acid (125 mg, TID) administration

| Ceft MIC \| Clav $C_T$ | % Time above MIC or $C_T$ | | | | | | | |
|---|---|---|---|---|---|---|---|---|
| | 50 \| 20 | 60 \| 20 | 50 \| 30 | 60 \| 30 | 50 \| 40 | 60 \| 40 | 50 \| 50 | 60 \| 50 |
| 1 \| 0.125 | 100 | 97.5 | 100 | 97.5 | 100 | 97.5 | 98.6 | 96.1 |
| 2 \| 0.125 | 75.1 | 35.5 | 75.1 | 35.5 | 75.1 | 35.5 | 74 | 34.9 |
| 1 \| 0.25 | 100 | 97.5 | 100 | 97.5 | 98.5 | 96 | 74.4 | 72.4 |
| 2 \| 0.25 | 75.1 | 35.5 | 75.1 | 35.5 | 74 | 35 | 56.3 | 27 |
| 1 \| 0.5 | 100 | 97.5 | 97.6 | 95.1 | 62.5 | 60.8 | 28.6 | 28 |
| 2 \| 0.5 | 75.1 | 35.5 | 73.4 | 34.5 | 46.6 | 22 | 20.6 | 9.1 |
| 1 \| 1 | 89.1 | 86.7 | 36.9 | 35.7 | 7.7 | 7.6 | 2.2 | 2.2 |
| 2 \| 1 | 66.8 | 31.6 | 27.6 | 12.5 | 5.3 | 3.1 | 1.6 | 0.9 |

Ceft = ceftibuten;
Clav = clavulanic acid;
CrCL = creatinine clearance;
MIC = minimum inhibitory concentration;
$C_T$ = threshold concentration;
TID = three times per day.

TABLE 15

Percentage of cases where free-drug plasma concentrations exceed MIC and $C_T$ in normal renal function (CrCL: > 80 mL/min) following ceftibuten (300 mg, TID) clavulanic acid (187.5 mg, TID) administration

| Ceft MIC \| Clav $C_T$ | % Time above MIC or $C_T$ | | | | | | | |
|---|---|---|---|---|---|---|---|---|
| | 50 \| 20 | 60 \| 20 | 50 \| 30 | 60 \| 30 | 50 \| 40 | 60 \| 40 | 50 \| 50 | 60 \| 50 |
| 1 \| 0.125 | 100 | 98.1 | 100 | 98.1 | 100 | 98.1 | 100 | 98.1 |
| 2 \| 0.125 | 73.1 | 34.4 | 73.1 | 34.4 | 73.1 | 34.4 | 73.1 | 34.4 |
| 1 \| 0.25 | 100 | 98.1 | 100 | 98.1 | 100 | 98.1 | 93 | 91.2 |
| 2 \| 0.25 | 73.1 | 34.4 | 73.1 | 34.4 | 73.1 | 34.4 | 68.8 | 32.1 |
| 1 \| 0.5 | 100 | 98.1 | 100 | 98.1 | 90.4 | 88.6 | 57.3 | 56.2 |
| 2 \| 0.5 | 73.1 | 34.4 | 73.1 | 34.4 | 66.4 | 30.9 | 42.3 | 20.3 |
| 1 \| 1 | 100 | 98.1 | 83.7 | 82.4 | 37.1 | 36.4 | 12 | 11.6 |
| 2 \| 1 | 73.1 | 34.4 | 61.9 | 28.9 | 27.6 | 12.7 | 8.9 | 4.3 |

Ceft = ceftibuten;
Clav = clavulanic acid;
CrCL = creatinine clearance;
MIC = minimum inhibitory concentration;
TC = threshold concentration;
TID = three times per day.

Example 8: Interaction of Cephalosporins and CTX-M-15

To assess why ceftibuten had a better clavulanate-induced PBLIE than other cephalosporins tested, a series of degradation assays were performed. It was hypothesized that ceftibuten may not be degraded by ESBLs such as CTX-M-15 as quickly as other cephalosporins such as cefotaxime, cefpodoxime, or cefixime.

A direct-turnover assay was performed to determine the kinetics of CTX-M-15-mediated degradation (hydrolysis) of four cephalosporins: ceftibuten, cefotaxime, cefpodoxime, or cefixime by direct measurement of cephalosporin ring opening. Approximately 100 mM Tris, pH 7, 0.02% Triton X-100, with varying concentrations of cephalosporin. Reactions were initiated by addition of CTX-M15 in a 96 well, UV compatible plate. Hydrolysis was determined by measuring the absorbance at 260 nm over time using an Envision plate reader. GraphPad was used to fit the linear progression of cephalosporin turnover. A linear fit was used to find the slopes (rates) of the cephalosporin turnover. The observed rates were plotted against the cephalosporin concentration in order to determine the kinetic parameters of interest.

Degradation was assumed to follow the model:

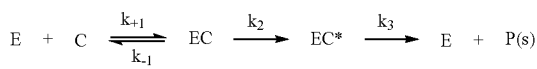

wherein E is CTX-M-15 and C is the cephalosporin.

$K_m = (k_{+3} \cdot K')/(k_{+2} + k_{+3})$ $K' = (k_{-1} + k_{+2})/k_{+1}$.

The $IC_{50}$ of each cephalosporin was also determined by using a competition assay with nitrocefin. Approximately 0.01 nM CTX-M-15, 10 μM nitrocefin, and a 2-fold dilution series of the cephalosporin ranging from 0-500 μM where added to a 96 well plate. Nitrocefin turnover was determined by measuring absorbance at 486 nm over time using a VersaMax plate reader. GraphPad was used to fit the linear progression of nitrocefin turnover as a function of cephalosporin concentration. Data was fit to a three-parameter inhibition curve to generate $IC_{50}$ values for each cephalosporin. Results from both assays are shown in Table 16.

TABLE 16

CTX-M-15 kinetic parameters measured for Cephalosporins

| Compound | $k_{cat}$ ($s^{-1}$) | $k_{cat}/K_M$ ($M^{-1}s^{-1}$) | $K_M$ (μM) (95% CI) | $IC_{50}$ (μM) (95% CI) | MIC (μg/mL) AECO001 | CTX-M-15 Strain − CLV | CTX-M-15 Strain + CLV |
|---|---|---|---|---|---|---|---|
| cefotaxime | 92 | 4.0E+06 | 23 (20-26) | 31 (18-54) | 0.125 | — | — |
| cefpodoxime | 50 | 3.8E+06 | 13 (10-16) | 24 (19-30) | 0.5 | >64 | 4 |
| cefixime | 2 | 1.4E+05 | 14 (11-18) | 20 (15-28) | 1 | >64 | 2 |
| ceftibuten | n.d. | 5.7E+04 | >100 | >1000 | 0.5 | 16 | 1 |

Ceftibuten did not saturate CTX-M-15 activity and did not compete with nitrocefin up to 1 mM. By contrast, cefixime saturated CTX-M-15 activity at 14 μM and competed with nitrocefin at $IC_{50}$=20 μM.

Figure 8:
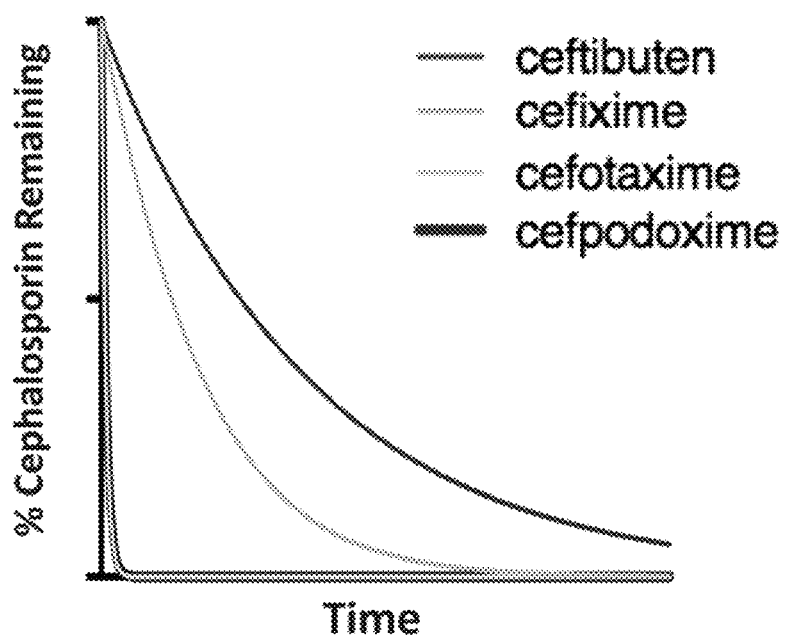
FIG. 8 shows a simulated graph of the percent cephalosporin remaining over time generated from measured kinetic constants.

The measured kinetic constants were then used to generate a simulated graph of the percent cephalosporin remaining over time (FIG. 8). Under sub-saturating conditions, ceftibuten was degraded by CTX-M-15 about 2.5, 67, and 70-fold slower than cefixime, cefpodoxime, and cefotaxime, respectively.

Since the PBLIE experiments described in Example 6 were performed with cephalosporin concentrations at MIC, e.g. 2 μg/mL (~5 μM) for ceftibuten, ceftibuten's concentration in this Example was sub-saturating.

Example 9: In Vivo Drug-Drug Interaction

Although both ceftibuten and clavulanate are known to be well tolerated, it was unknown whether administering the combination of two drugs would cause a drug-drug interaction (DDI). To determine the potential for DDI, Sprague-Dawley rats (n=6 per cohort) were administered an oral bolus of 34.5 mg/kg ceftibuten, 10.8 mg/kg clavulanic acid (clavulanate), or 34.5 mg/kg ceftibuten and 10.8 mg/kg clavulanic acid (clavulanate). These doses were estimated to be equivalent to human ceftibuten-clavulanate combination doses of 400 and 125 mg, respectively, based on a 70-kg human body weight and the FDA Guidance for Industry: Estimating the Maximum Safe Starting Dose in Initial Clinical Trials for Therapeutics in Adult Healthy Volunteers (FDA 2005).

Figure 9A:
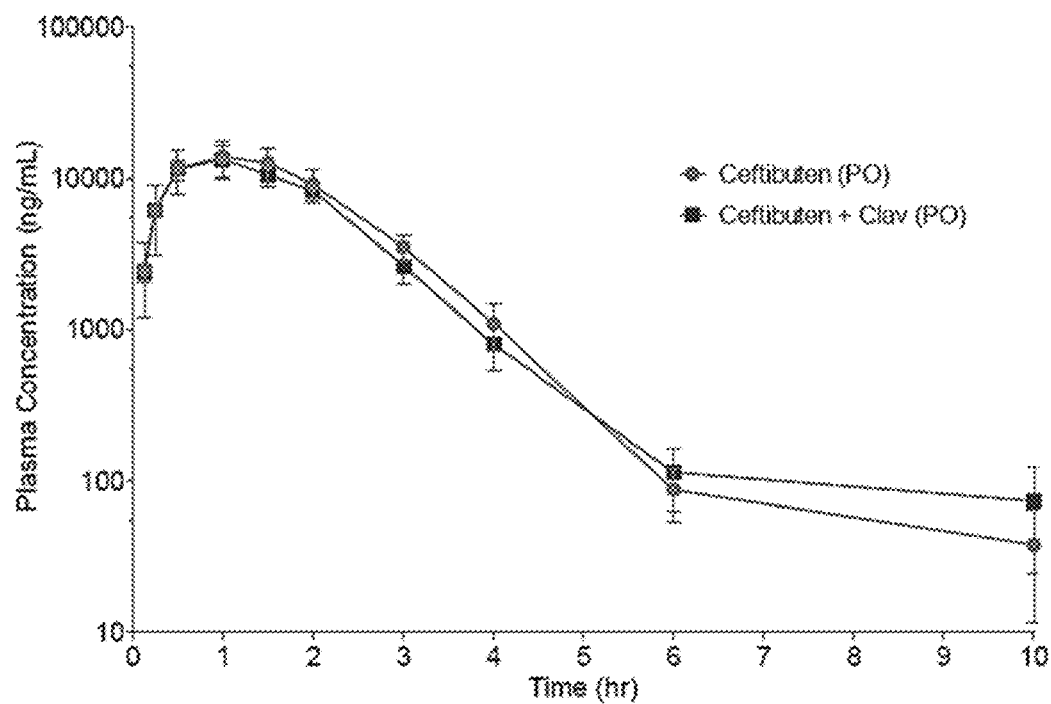
FIG. 9A shows plasma concentrations of ceftibuten at various timepoints following oral administration of 34.5 mg/kg ceftibuten alone or 34.5 mg/kg ceftibuten+10.8 mg/kg clavulanate.
Figure 9B:
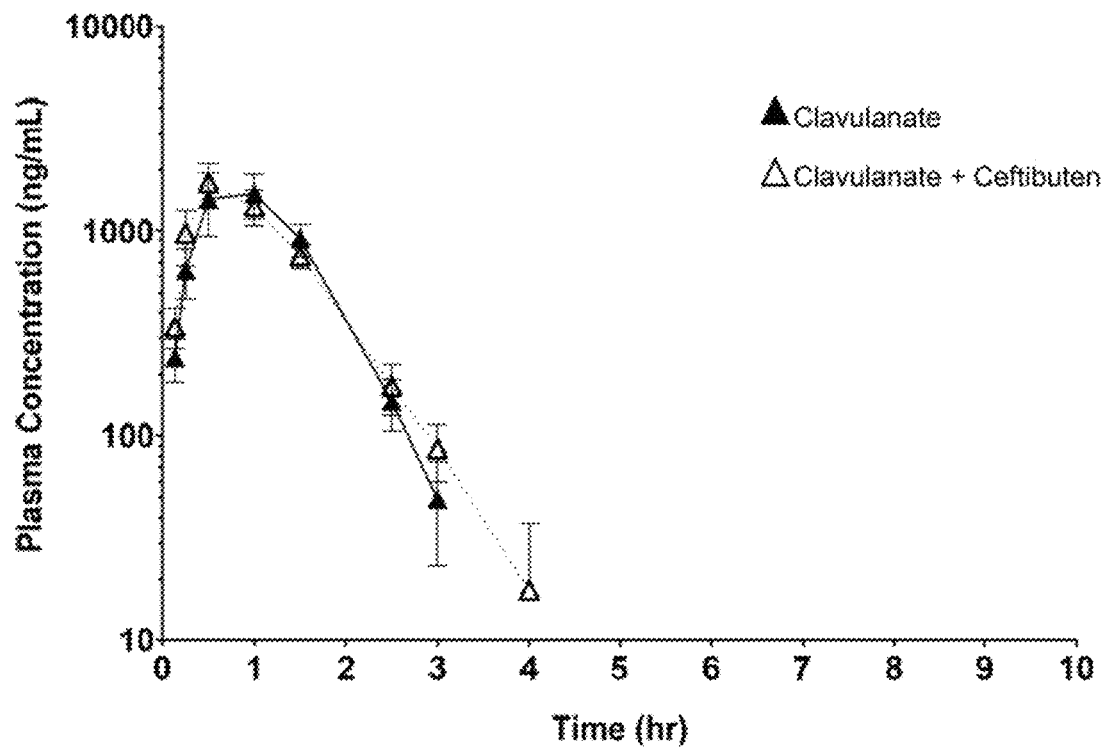
FIG. 9B shows plasma concentrations of clavulanic acid at various timepoints following oral administration of 10.8 mg/kg clavulanate alone or 34.5 mg/kg ceftibuten+10.8 mg/kg clavulanate. n=6 for each treatment group.

Plasma concentrations of ceftibuten or clavulanate at various timepoints were determined using standard methods and the results are shown in FIGS. 9A-9B, respectively. As shown in FIG. 9A, administering the ceftibuten and clavulanic acid combination did not markedly alter the plasma concentration of ceftibuten compared to administering ceftibuten alone. As shown in FIG. 9B, administering ceftibuten and clavulanic acid combination did not markedly alter the plasma concentration of clavulanic acid compared to administering clavulanaic acid alone.

Pharmacokinetic parameters were calculated and are presented below in Table 17. Comparison of the parameters for the test articles between the single and combined doses using a two-tailed t-test showed statistically significant differences for some of the parameters. Given that the maximum concentration did not change for either of the analytes and that the exposure of ceftibuten was decreased by less than 17%, these data are consistent with limited potential for drug-drug-interactions between the two components.

TABLE 17

| Analyte | Dose | Terminal Half-Life, H | Tmax, h | Cmax, μg/mL | $AUC_\infty$, μg × h/mL |
|---|---|---|---|---|---|
| Ceftibuten | Ceftibuten | 1.44 ± 0.232 | 0.915 ± 0.49 | 10.0 ± 2.18 | 21.5 ± 1.67 |
|  | Ceftibuten + Clavulanic Acid | 2.05 ± 0.964 | 0.670 ± 0.419 | 8.51 ± 0.76 | 18.0 ± 1.3[a] |
| Clavulanic Acid | Clavulanic Acid | 0.361 ± 0.0255 | 0.833 ± 0.258 | 1.61 ± 0.432 | 2.28 ± 0.471 |
|  | Ceftibuten + Clavulanic Acid | 0.593 ± 0.191[a] | 0.499 ± 0.00183[a] | 1.73 ± 0.416 | 2.30 ± 02.97 |

[a]Value following combined dose differs versus individual dose (P < 0.05)

Figure 10A:
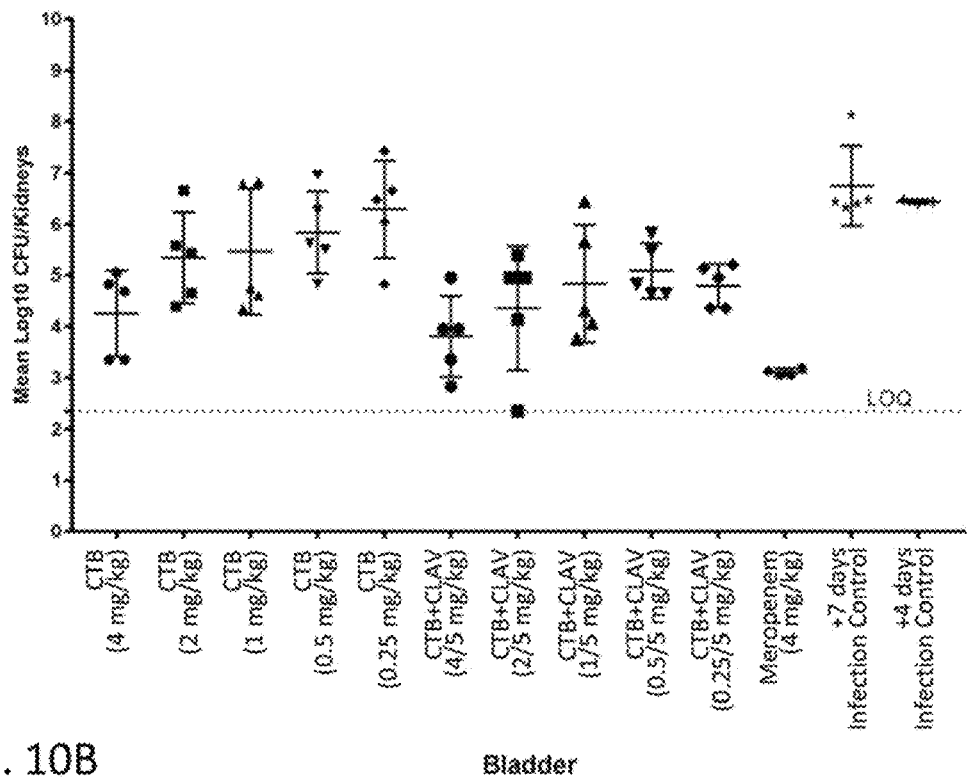
FIGS. 10A-10C show mean $\log_{10}$ CFU counts from the kidney (FIG. 10A), bladder (FIG. 10B), and urine (FIG. 10C) of mice treated with ceftibuten or ceftibuten+clavulanate in a murine UTI model of infection using an *E. coli* CTX-M-15-expressing isolate.
Figure 10B:
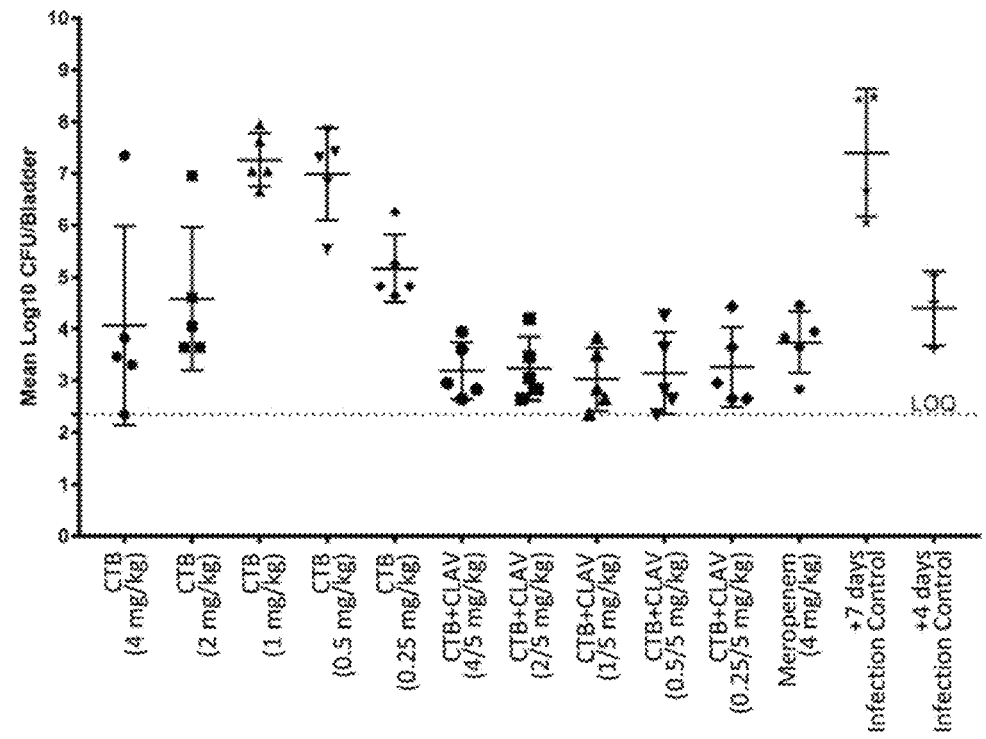
Figure 10C:
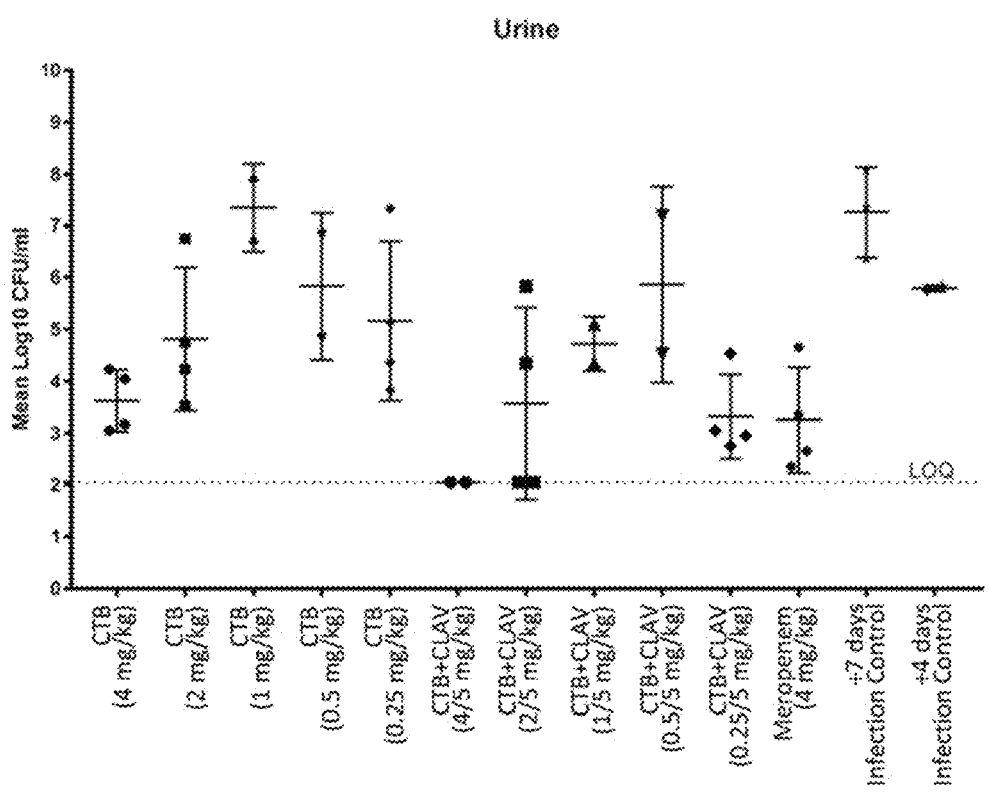

Example 10: Efficacy of Ceftibuten and Clavulanate in a Mouse Complicated Urinary Tract Infection (cUTI) Model The efficacy of ceftibuten+clavulanate was evaluated in a mouse complicated urinary tract infection (cUTI) model against an *E. coli* clinical isolate expressing the ESBL CTX-M-15. Mice were infected by trans-urethral injection of the inoculum. Treatment was initiated at 4 days post-infection using a q4 h (every 4 hours) regimen where mice were dosed subcutaneously with ceftibuten alone, ceftibuten+clavulanate, or a meropenem control. Ceftibuten doses ranged from 0.25-4 mg/kg, and a fixed dose of 5 mg/kg clavulanate was used to assess the ceftibuten+clavulanate combination. Mice were euthanized 4 and 7 days post-infection. Urine, kidney, and bladder were collected to assess bacterial loads as determined by CFU counts. Results are shown in FIGS. 10A-10C.

Ceftibuten alone administered from 0.25-4 mg/kg (q4 hr) for 3 days, exhibited a dose response in this model. Relative to the untreated control group, a ceftibuten dose from 0.5-4 mg/kg reduced bacterial titers by 0.6-2.17 $\log_{10}$ CFU in kidneys (4.26-5.83 $\log_{10}$ CFU) (FIG. 10A), 2.8-3.35 $\log_{10}$ CFU in the bladder (4.06-4.58 $\log_{10}$ CFU) (FIG. 10B), and 2.46-3.65 $\log_{10}$ CFU in urine (3.62-4.81 $\log_{10}$ CFU) (FIG. 10C). As shown in FIGS. 10A-10C, the addition of clavulanate to these doses of ceftibuten further reduced the CFU in kidneys, bladder and urine, respectively. Bacterial titers in kidneys were 0.45-1.46 $\log_{10}$ CFU lower for the combination at doses at 0.25/5 and 4/5 mg/kg as compared to the same doses of ceftibuten alone (FIG. 10A). Bacterial titers for the combination at doses 0.25/5 and 4/5 mg/kg were 0.86-1.89 $\log_{10}$ CFU lower in bladder (FIG. 10B) and 1.57-1.85 $\log_{10}$ lower CFU in urine (FIG. 10C). Meropenem (4 mg/kg, q4 hr) reduced bacterial CFU to 3.11, 3.75, and 3.25 $\log_{10}$ CFU in kidneys, bladder and urine, respectively.

Addition of clavulanate reduced bacterial titers in the kidneys, bladder, and urine when compared to ceftibuten alone. These data show that the combination of ceftibuten with the β-lactamase inhibitor clavulanate enhances efficacy against ESBL-producing Enterobacteriaceae in vivo.

Example 11 Safety, Tolerability and Pharmacokinetics (PK) of Ceftibuten and Clavulanate Combination in Healthy Adults To assess safety, tolerability and pharmacokinetics (PK) of ceftibuten and clavulanate, a single dose (SD) and multiple doses (MD) study of ceftibuten and clavulanate or placebo in healthy subjects was carried out by oral administration as separate capsules, alone and concurrently.

In an initial cohort of subjects receiving 400 mg ceftibuten/125 mg clavulanate twice daily, six subjects were randomized to receive active drug and two were randomized to receive placebo. Per their randomization, subjects received a single dose (SD) of 125 mg clavulanate or placebo (day 1), followed by a 48-hour washout, followed by a SD of 400 mg ceftibuten or placebo (day 3), followed by a 48-hour washout, followed by a combination SD of 400 mg ceftibuten+125 mg clavulanate or placebo (day 5). The subjects then received a combination of 400 mg ceftibuten+125 mg clavulanate or placebo, twice daily, for 14 days (days 6-19). For each dose, subjects received two 200 mg capsules of ceftibuten and one 125 mg capsule of clavulanate. The twice daily divided dose of study drug was administered approximately 12 hours apart. All subjects randomized to placebo received placebo oral capsules that were identical to study drug capsules and given according to the same dosing schedule and same quantity of capsules as subjects randomized to receive ceftibuten and clavulanate concurrently.

All SDs, as well as the first daily dose of the MD period on day 19 were given while the subject was fasted. Fasted was defined as an overnight fast of at least 10 hours prior to dose and at least 4 hours post SD. All other doses during the MD period were administered on an empty stomach (at least 1 hour before eating or 2 hours after eating), except on Day 6 of the MD period, when the first dose of the day was administered 30 minutes after a high-fat, high-calorie meal.

Safety and tolerability of ceftibuten and clavulanate were monitored throughout the course of the study by clinical assessments of adverse effects (AEs) and repeated measurements of clinical evaluations including: vital signs (temperature, blood pressure (BP), heart rate, respiratory rate), physical examinations, electrocardiograms, laboratory assessments including complete blood count (CBC) with differential, serum chemistry, liver function tests and urinalysis.

For PK assessments, blood and urine samples were collected from subjects for the analysis of concentrations of ceftibuten, clavulanate, and, in some aspects, corresponding metabolites. Blood sample for plasma PK were collected pre-dose and at various times post-dose following the SDs on days 1, 3, and 5 and the first daily dose on study day 6 and day 9. In addition, blood samples for assessment of trough (pre-dose) concentrations were collected on day 7, day 8, day 9, and alternate days thereafter through study day 17. At various intervals (~4 to 12 hour intervals), urine was collected and pooled following the SDs on days 1, 3, and 5 and following the first dose on day 19.

Preliminary PK data of ceftibuten, clavulanate and the amino ketone metabolite of clavulanate following dosing on Study Day 1, Study Day 3, and Study Day 5 were assessed. PK parameters were estimated from individual plasma concentration-time profiles using a noncompartmental analysis (NCA) within Phoenix (Pharsight, Mountain View, Calif.) and are summarized for ceftibuten and clavulanate in Table 18 and Table 19, respectively. Peak concentration ($C_{max}$), time at which $C_{max}$ was observed ($T_{max}$), area under the concentration-time curve to infinity ($AUC_{inf}$), percent coefficient of variation (% CV), elimination half-life ($T_{1/2}$), apparent total clearance of the drug from plasma after oral administration (CL/F), and apparent volume of distribution during terminal phase after non-intravenous administration (Vz/F) were determined. No major drug-drug interaction (DDI) was observed following co-administration of a single oral dose of ceftibuten (2×200 mg) and clavulanate (1×125 mg) capsules.

PK parameters for ceftibuten were generally similar when ceftibuten was administered alone and in combination with clavulanate. Geometric mean $C_{max}$ was slightly decreased, geometric mean $T_{max}$ (time at which $C_{max}$ was observed) was slightly delayed, however $AUC_{inf}$ was slightly increased when administered alone and in combination with clavulanate, respectively (Table 18). Ceftibuten exhibited low variability in exposure ($C_{max}$ and $AUC_{inf}$), as assessed by the geometric mean % CV values ranging from 11 to 16% when ceftibuten was administered alone and 15 to 31% when ceftibuten was administered in combination.

PK parameters for clavulanate were comparable when administered alone and in combination with ceftibuten (Table 19). Exposure to clavulanate was highly variable, with the geometric mean % CV for $C_{max}$ and $AUC_{inf}$ of approximately 80%, when given alone or in combination with ceftibuten. The amino ketone metabolite of clavulanate accounted for approximately 8.5% and 6.5% of parent exposure when clavulanate was administered alone and in combination with ceftibuten, respectively.

Overall, these preliminary data demonstrate there was no apparent drug-drug interaction (DDI) between ceftibuten and clavulanate following administration of a single oral dose. Variability in clavulanate PK parameters may be driven by one subject with unusually low exposure.

TABLE 18

Summary of PK Parameters for Ceftibuten Following a Single Dose

|  | Subject | $T_{max}$ (hr) | $C_{max}$ (μg/mL) | $AUC_{inf}$ (hr*μg/mL) | $T\frac{1}{2}$ (hr) | CL/F (mL/min) | Vz/F (L) |
|---|---|---|---|---|---|---|---|
| Ceftibuten (400 mg) | 1 | 1.00 | 19.5 | 89.3 | 3.32 | 74.6 | 21.5 |
|  | 2 | 1.50 | 19.7 | 90.7 | 2.79 | 73.5 | 17.8 |
|  | 3 | 3.00 | 17.7 | 102 | 3.24 | 65.7 | 18.4 |
|  | 4 | 1.25 | 25.8 | 100 | 2.96 | 66.5 | 17 |
|  | 5 | 2.00 | 17.9 | 93.0 | 3.11 | 71.7 | 19.3 |
|  | 6 | 3.00 | 16.3 | 119 | 3.4 | 56.1 | 16.5 |
|  | Mean | 1.96 | 19.5 | 98.9 | 3.14 | 68.0 | 18.4 |
|  | SD | 0.872 | 3.34 | 10.9 | 0.232 | 6.88 | 1.79 |
|  | CV % | 44.5 | 17.1 | 11.1 | 7.39 | 10.1 | 9.7 |
|  | Geometric Mean | 1.80 | 19.3 | 98.4 | 3.13 | 67.7 | 18.3 |
|  | CV % GeoMean | 48.2 | 16.0 | 10.6 | 7.52 | 10.6 | 9.46 |
| Ceftibuten-clavulanate (400 mg/ 125 mg) |  |  |  |  |  |  |  |
|  | 1 | 4.00 | 17.7 | 126 | 3.36 | 53.0 | 15.4 |
|  | 2 | 3.00 | 17.9 | 107 | 2.78 | 62.2 | 15.0 |
|  | 3 | 6.00 | 11.0 | 88.5 | 3.57 | 75.3 | 23.3 |
|  | 4 | 1.50 | 28.3 | 124 | 2.87 | 53.7 | 13.3 |
|  | 5 | 4.00 | 15.7 | 90.9 | 3.11 | 73.4 | 19.8 |
|  | 6 | 4.00 | 15.5 | 113 | 3.42 | 59.0 | 17.5 |
|  | Mean | 3.75 | 17.7 | 108 | 3.19 | 62.8 | 17.4 |
|  | SD | 1.47 | 5.76 | 16.0 | 0.318 | 9.62 | 3.65 |
|  | CV % | 39.3 | 32.6 | 14.8 | 9.97 | 15.3 | 21 |
|  | Geometric Mean | 3.46 | 17.0 | 107 | 3.17 | 62.2 | 17.1 |
|  | CV % GeoMean | 49.2 | 31.3 | 15.2 | 10.1 | 15.2 | 20.5 |

TABLE 19

Summary of PK Parameters for Clavulanate Following a Single Dose

|  | Subject | $T_{max}$ (hr) | $C_{max}$ (μg/mL) | $AUC_{inf}$ (hr*μg/mL) | $T\frac{1}{2}$ (hr) | CL/F (mL/min) | Vz/F (L) |
|---|---|---|---|---|---|---|---|
| Clavulanate (125 mg) | 1 | 1.25 | 2.26 | 5.28 | 1.10 | 395 | 37.7 |
|  | 2 | 1.00 | 2.40 | 5.37 | 1.09 | 388 | 36.7 |
|  | 3 | 1.00 | 1.68 | 3.60 | 1.06 | 579 | 52.8 |
|  | 4 | 1.00 | 2.06 | 3.97 | 0.996 | 524 | 45.2 |
|  | 5 | 1.00 | 0.400 | 0.79 | 0.775 | 2640 | 177 |
|  | 6 | 2.00 | 1.99 | 5.17 | 1.33 | 403 | 46.2 |
|  | Mean | 1.21 | 1.80 | 4.03 | 1.06 | 821 | 65.9 |
|  | SD | 0.401 | 0.728 | 1.75 | 0.178 | 893 | 54.7 |
|  | CV % | 33.1 | 40.5 | 43.5 | 16.8 | 109 | 83 |
|  | Geometric Mean | 1.16 | 1.57 | 3.44 | 1.05 | 606 | 54.8 |
|  | CV % GeoMean | 28.5 | 76.8 | 85.3 | 17.6 | 85.3 | 64.5 |
| Ceftibuten-clavulanate (400 mg/ 125 mg) |  |  |  |  |  |  |  |
|  | 1 | 2.00 | 1.34 | 3.70 | 1.45 | 563 | 70.7 |
|  | 2 | 1.00 | 2.78 | 5.66 | 1.05 | 368 | 33.4 |
|  | 3 | 1.00 | 1.44 | 3.03 | 1.02 | 688 | 60.7 |
|  | 4 | 1.00 | 4.73 | 8.84 | 1.06 | 236 | 21.7 |
|  | 5 | 1.25 | 1.05 | 1.95 | 0.868 | 1070 | 80.1 |
|  | 6 | 1.50 | 0.572 | 1.20 | 1.07 | 1730 | 161 |
|  | Mean | 1.29 | 1.99 | 4.06 | 1.09 | 775 | 71.2 |
|  | SD | 0.401 | 1.53 | 2.80 | 0.193 | 549 | 49.2 |
|  | CV % | 31.0 | 77.2 | 68.9 | 17.7 | 70.8 | 69.0 |
|  | Geometric Mean | 1.25 | 1.57 | 3.31 | 1.07 | 629 | 58.5 |
|  | CV % GeoMean | 29.0 | 85.8 | 82.1 | 16.8 | 82.1 | 79.6 |

An additional group of healthy subjects were orally administered ceftibuten and clavulanate or placebo, alone or concurrently as separate capsules, in a single dose (SD) and multiple dose (MD) regimen similar to above, except following an alternative dosing regimen involving administration of 400 mg ceftibuten/125 mg clavulanate three times daily (TID). Similar to above, six subjects were randomized to receive active drug and two were randomized to receive placebo. In this additional group, subjects received a single dose (SD) of 125 mg clavulanate or placebo (day 1), followed by a 48-hour washout, followed by a SD of 400 mg ceftibuten or placebo (day 3), followed by a 48-hour washout, followed by a combination SD of 400 mg ceftibuten+125 mg clavulanate or placebo (day 5), and then a combination of 400 mg ceftibuten+125 mg clavulanate or placebo, three times daily (TID), for 14 days (days 6-19). Safety, tolerability and PK were assessed as described above.

One or more additional cohort(s) of healthy subjects are evaluated for safety, tolerability and PK as described above following administration of alternative dosing regimens of ceftibuten and clavulanate up to a maximum total daily dose of 1.8 grams of ceftibuten and 750 mg of clavulanate. In each additional cohort, six subjects are randomized to receive active drug and two are randomized to receive placebo similar to above in a SD and MD study period. Exemplary dosing regimens are set forth as follows:

300 mg ceftibuten/187.5 mg clavulanate three times daily: subjects receive a single dose (SD) of 187.5 mg clavulanate or placebo (day 1), followed by a 48-hour washout, followed by a SD of 300 mg ceftibuten or placebo (day 3), followed by a 48-hour washout, followed by a combination SD of 300 mg ceftibuten+187.5 mg clavulanate or placebo (day 5), and then a combination of 300 mg ceftibuten+187.5 mg clavulanate or placebo, three times daily (TID), for 14 days (days 6-19).

400 mg ceftibuten/187.5 mg clavulanate three times daily: subjects receive a single dose (SD) of 187.5 mg clavulanate or placebo (day 1), followed by a 48-hour washout, followed by a SD of 400 mg ceftibuten or placebo (day 3), followed by a 48-hour washout, followed by a combination SD of 400 mg ceftibuten+187.5 mg clavulanate or placebo (day 5), and then a combination of 400 mg ceftibuten+187.5 mg clavulanate or placebo, three times daily (TID), for 14 days (days 6-19).

Example 12 Safety, Tolerability and Pharmacokinetics (PK) of Ceftibuten and Clavulanate Combination in Patients with Renal Impairment To assess safety, tolerability and pharmacokinetics (PK) in patients with renal impairment, single doses (SD) of ceftibuten and clavulanate is given concurrently, to subjects with moderate or severe renal impairment. Subjects with moderate renal impairment have a creatine clearance (CLcr) as estimated by the Cockcroft-Gault equation and most recent serum creatinine collected within the screening period of ≥30 mL/min to <60 mL/min. Subjects with severe renal impairment have a CLcr as estimated by the Cockcroft-Gault equation and most recent serum creatinine collected within the screening period of ≥15 mL/min to <30 mL/min. For both groups of subjects, subjects are administered a SD of 400 mg ceftibuten and 125 mg clavulanate via separate oral capsules given concurrently.

Safety and pharmacokinetic analysis is carried out. Safety and tolerability of ceftibuten and clavulanate are monitored by clinical assessments of AEs and repeated measurements of clinical evaluations including: vital signs (temperature, blood pressure [BP], heart rate, and respiratory rate), physical examinations, electrocardiograms, laboratory assessments including complete blood count (CBC) with differential, serum chemistry, liver function tests and urinalysis. Blood for CBC with differential and serum chemistry and urine for PK analysis and urinalysis is collected pre-SD and approximately seven days post-SD on day 8. CBC includes hemoglobin, hematocrit, platelet count, red blood cell (RBC) count, white blood cell (WBC) count, and percent or absolute differential count (neutrophils, lymphocytes, and other cells). Serum chemistry includes sodium, potassium, chloride, magnesium, bicarbonate, glucose, blood urea nitrogen (BUN), creatinine, uric acid, and albumin. Urinalysis includes color, clarity/turbidity, pH, specific gravity, glucose, ketones, nitrites, leukocyte esterase, protein, RBCs, WBCs, epithelial cells, casts, and crystals. Liver function also is performed pre-SD and post-SD within 2 hours of dosing on day 1 and once on day 8. Liver function tests include aspartate aminotransferase (AST), alanine aminotransferase (ALT), alkaline phosphatase, total bilirubin, and direct bilirubin.

Blood and urine sample are collected for analysis of concentrations of ceftibuten, clavulanate and, in some cases, corresponding metabolites. Plasma for PK analysis is collected for analysis up to 10 minutes pre-dose and at various time points through 96 hours pose-SD of single combination dose. At various intervals (~4 to 12 hour intervals), urine is collected and pooled after oral drug administration through 96 hours pose-SD of single combination dose. In some cases, for a PK comparison, each subject with moderate and severe renal impairment is matched with respect to age (±10 years), BMI (±15%), race, and gender to a subject from Example 11 that also received a dose of 400 mg ceftibuten and 125 mg clavulanate.

Example 13 Combination Treatment with Ceftibuten and Clavulanate in Patients with Complicated Urinary Tract Infection (cUTI), Including Acute Pyelonephritis (AP)

The combination of ceftibuten and clavulanate are administered orally to adult patients with complicated urinary tract infection (cUTI), including acute pyelonephritis (AP). In some embodiments, the criteria for cUTI or AP diagnosis are generally consistent with the FDA Guidance for cUTI. Patients have at least 2 signs and/or symptoms of infection and patients with cUTI have at least 1 complicating factor (e.g., males with a history of urinary retention, urinary catheterization, structural or anatomical abnormality of the urinary tract, or neurological deficiencies resulting in residual urine of at least 100 mL).

Ceftibuten and clavulanate are administered as oral capsules in BID or TID divided daily dose amounts, such as described in Example 11, for a treatment duration of 7 to 10 days. Safety and efficacy is evaluated during treatment and at the end-of-treatment (EOT) visit. Patients also are assessed for safety and efficacy at later times post-treatment, such as approximately at Day 17 and/or at approximately Day 28.

The primary efficacy endpoint is the composite clinical and microbiological cure rate, such as at Day 17, in patients in the microbiologically modified intent-to-treat (mMITT)

population. Clinical and microbiological endpoints are assessed at the end of treatment (EOT) as secondary endpoints.

Safety and efficacy are compared with a currently approved IV therapy also given for a treatment duration of 7 to 10 days. Examples of IV comparators include IV carbapenems (e.g., ertapenem, meropenem or imipenem/cilastatin) and β-lactam/β-lactamase inhibitor combinations (e.g., ceftolozane/tazobactam or piperacillin/tazobactam). The use of an IV comparator is necessary as no oral antibiotic is available for use against ESBL-producing Enterobacteriaceae that will provide a clinically meaningful comparison to establish the efficacy of ceftibuten+clavulanate in patients with cUTI, including those due to ESBL-producing or fluoroquinolone-resistant Enterobacteriaceae.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. A method of treating an Enterobacteriaceae bacterial infection, the method comprising orally administering to a human individual (a) ceftibuten or a pharmaceutically acceptable salt thereof, or a hydrate of the foregoing; and (b) clavulanic acid, or a pharmaceutically acceptable salt thereof, wherein:
   the bacterial infection is caused by an Enterobacteriaceae that expresses an extended-spectrum beta-lactamase (ESBL); and
   component (a) and component (b) are administered in three divided doses per day, wherein the divided dose of component (a) is about 300-400 mg of component (a) and the divided dose of component (b) is about 100-250 mg of component (b).

2. The method of claim 1, wherein the bacterial infection is a complicated urinary tract infection (cUTI), acute pyelonephritis, uncomplicated UTI (uUTI), complicated intra-abdominal infection (cIAI) or community acquired pneumonia (CAP).

3. The method of claim 1, wherein the bacterial infection is complicated urinary tract infection (cUTI) or acute pyelonephritis.

4. The method of claim 1, wherein component (a) and component (b) are administered simultaneously.

5. The method of claim 1, wherein component (a) and component (b) are administered sequentially.

6. The method of claim 1, wherein the divided dose of component (b) is about 125-187.5 mg.

7. The method of claim 1, wherein component (a) is ceftibuten dihydrate.

8. The method of claim 1, wherein component (b) is potassium clavulanate.

9. The method of claim 1, wherein component (a) and component (b) are administered for 7-10 days.

10. The method of claim 1, wherein component (a) and component (b) are formulated as a capsule or a tablet.

11. The method of claim 1, wherein the Enterobacteriaceae is a C. freundii, E. aerogenes, E. cloacae, E. coli, K. pneumoniae, or K. oxytoca.

12. The method of claim 1, wherein the ESBL is a CTX-M.

13. A method of treating an Enterobacteriaceae bacterial infection, the method comprising orally administering to a human individual (a) ceftibuten, a pharmaceutically acceptable salt thereof, or a hydrate of the foregoing, wherein:
   the bacterial infection is caused by an Enterobacteriaceae that expresses an extended-spectrum beta-lactamase (ESBL);
   component (a) is administered in three divided doses per day, wherein the divided dose is about 300-400 mg; and
   component (a) is administered with (b) clavulanic acid or a pharmaceutically acceptable salt thereof, wherein component (b) is orally administered in three divided doses per day and the divided dose of component (b) is about 100-250 mg.

14. The method of claim 13, wherein the bacterial infection is a complicated urinary tract infection (cUTI), acute pyelonephritis, uncomplicated UTI (uUTI), complicated intra-abdominal infection (cIAI) or community acquired pneumonia (CAP).

15. The method of claim 13, wherein the bacterial infection is complicated urinary tract infection (cUTI) or acute pyelonephritis.

16. The method of claim 13, wherein component (a) is administered simultaneously with component (b).

17. The method of claim 13, wherein component (a) is administered sequentially with component (b).

18. The method of claim 13, wherein component (a) is ceftibuten dihydrate.

19. The method of claim 13, wherein component (b) is potassium clavulanate.

20. A method of treating an Enterobacteriaceae bacterial infection, the method comprising orally administering to a human individual (b) clavulanic acid or a pharmaceutically acceptable salt thereof, wherein:
   the bacterial infection is caused by an Enterobacteriaceae that expresses an extended-spectrum beta-lactamase (ESBL);
   component (b) is administered in three divided doses per day, wherein the divided dose of component (b) is about 100-250 mg; and
   component (b) is administered with (a) ceftibuten, a pharmaceutically acceptable salt thereof, or a hydrate of the foregoing, wherein component (a) is orally administered in three divided doses per day and the divided dose of component (a) is about 300-400 mg.

21. The method of claim 20, wherein the divided dose of component (b) is about 125-187.5 mg.

22. The method of claim 20, wherein the bacterial infection is a complicated urinary tract infection (cUTI), acute pyelonephritis, uncomplicated UTI (uUTI), complicated intra-abdominal infection (cIAI) or community acquired pneumonia (CAP).

23. The method of claim 20, wherein the bacterial infection is complicated urinary tract infection (cUTI) or acute pyelonephritis.

24. The method of claim 20, wherein component (b) is administered simultaneously with component (a).

25. The method of claim 20, wherein component (b) is administered sequentially with component (a).

26. The method of claim 20, wherein component (a) is ceftibuten dihydrate.

27. The method of claim 20, wherein component (b) is potassium clavulanate.

28. The method of claim 13, wherein component (a) and component (b) are administered for 7-10 days.

29. The method of claim 13, wherein the ESBL is a CTX-M.

30. The method of claim 20, wherein the ESBL is a CTX-M.

* * * * *